United States Patent
Yasunaga et al.

[11] Patent Number: 5,825,536
[45] Date of Patent: Oct. 20, 1998

[54] SURGICAL MICROSCOPE UNIT

[75] Inventors: Koji Yasunaga, Hino; Takashi Fukaya, Sagamihara, both of Japan

[73] Assignee: Olympus Optical Co., Ltd., Tokyo, Japan

[21] Appl. No.: 525,907

[22] Filed: Sep. 8, 1995

[30] Foreign Application Priority Data

Sep. 12, 1994 [JP] Japan ................................... 6-217511
Mar. 31, 1995 [JP] Japan ................................... 7-075209

[51] Int. Cl.⁶ .............................. G02B 21/00; F16L 3/00
[52] U.S. Cl. .......................... 359/384; 359/368; 359/382; 248/123.11; 248/281.11
[58] Field of Search .......................... 359/368, 382–384, 359/430; 248/123.11, 123.2, 124.1, 280.11, 281.11, 325.1

[56] References Cited

U.S. PATENT DOCUMENTS

| | | | |
|---|---|---|---|
| 4,344,595 | 8/1982 | Heller et al. | 248/542 |
| 4,437,635 | 3/1984 | Pham | 248/124.1 |
| 4,684,088 | 8/1987 | Heller | 248/123.2 |
| 4,741,607 | 5/1988 | Heller | 248/123.2 |
| 4,815,832 | 3/1989 | Nagano et al. | 359/389 |
| 4,867,405 | 9/1989 | Nakamura | 248/281.11 |
| 5,173,802 | 12/1992 | Heller | 359/389 |
| 5,186,422 | 2/1993 | Nakamura | 359/382 |
| 5,205,522 | 4/1993 | Nakamura | 248/123.11 |
| 5,345,334 | 9/1994 | Heller | 359/303 |
| 5,528,417 | 6/1996 | Nakamura | 359/384 |

FOREIGN PATENT DOCUMENTS

| | | |
|---|---|---|
| 0023003 | 1/1981 | European Pat. Off. . |
| 0476551 A1 | 3/1992 | European Pat. Off. . |
| 5-168648 | 7/1993 | Japan . |
| 5-215972 | 8/1993 | Japan . |

*Primary Examiner*—Thong Nguyen
*Attorney, Agent, or Firm*—Frishauf, Holtz, Goodman, Langer & Chick

[57] ABSTRACT

A surgical microscope unit which is compact and operated lightly at high stability has first and second parallelogrammic linkages, interlocking mechanisms for interlocking the first and second parallelogrammic linkages, a counterweight connected to an arm of the second parallelogrammic linkage, flexible movement transmitting members for transmitting tilting movements of the microscope body around pivot axes directly to a tilting rod as tilting movements around pivot axes at the same ratio, and a movement controlling mechanism for limiting a moving locus of the tilting rod to a corresponding location at which the microscope unit is set. The pivot axes are arranged so that a triangle formed by connecting the pivot axes is similar to a triangle formed by connecting the pivot axes in a plane parallel with a plane including a vertical axis. Auxiliary counterweights are provided on members interlocking with either the first interlocking mechanism or the second interlocking mechanism. When the microscope body is moved, the balancing weight does not project from the microscope body.

12 Claims, 26 Drawing Sheets

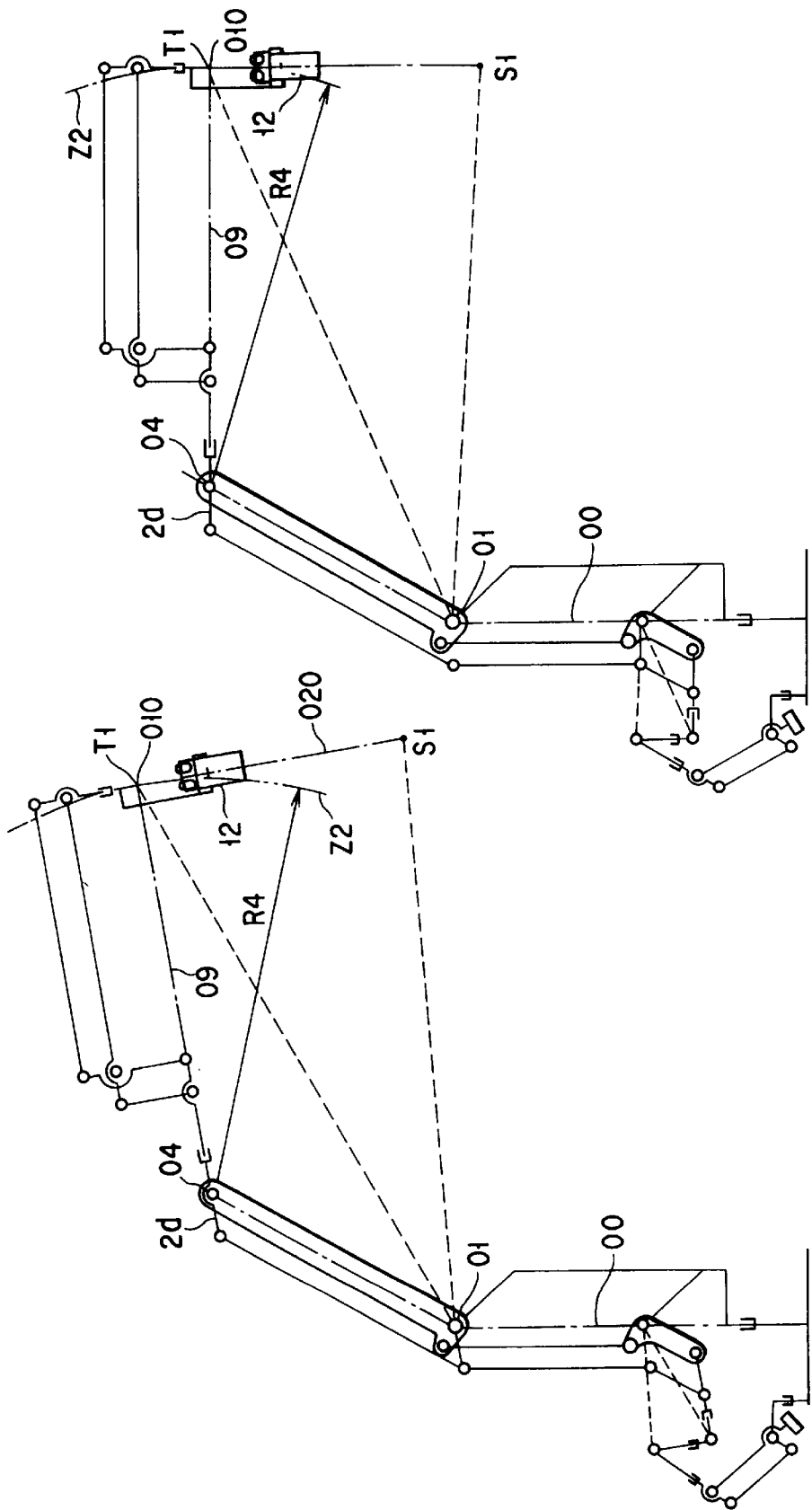

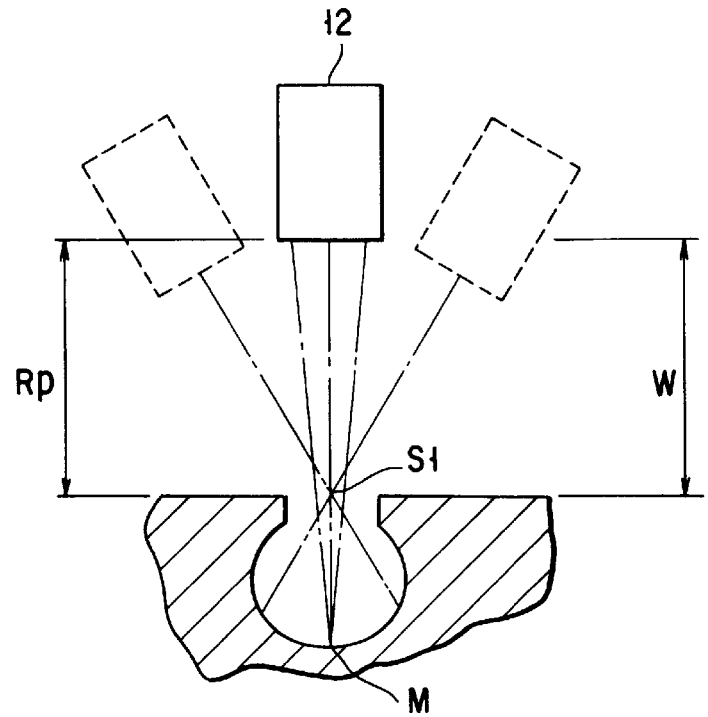
F I G. 11
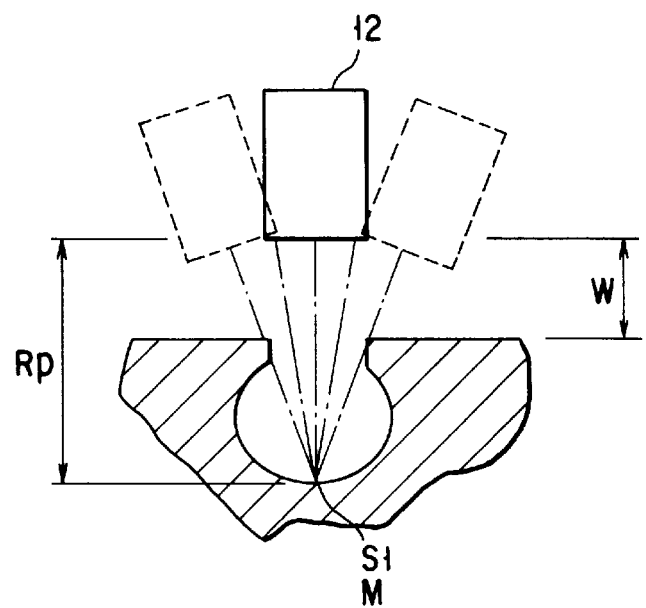
F I G. 12

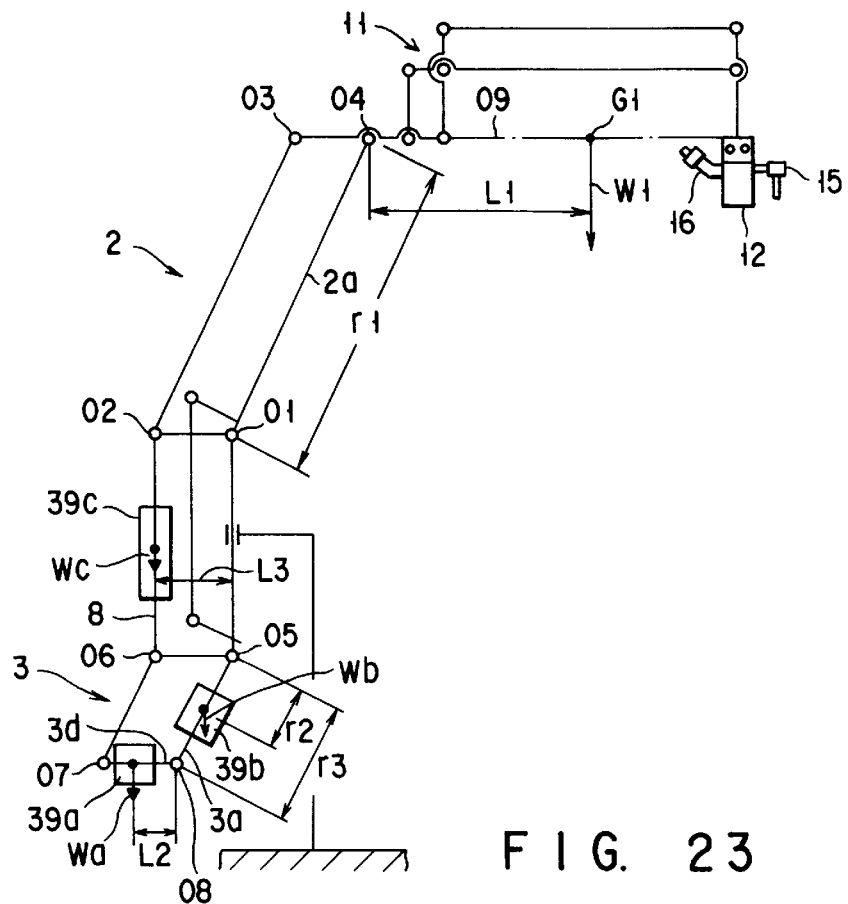
F I G. 23
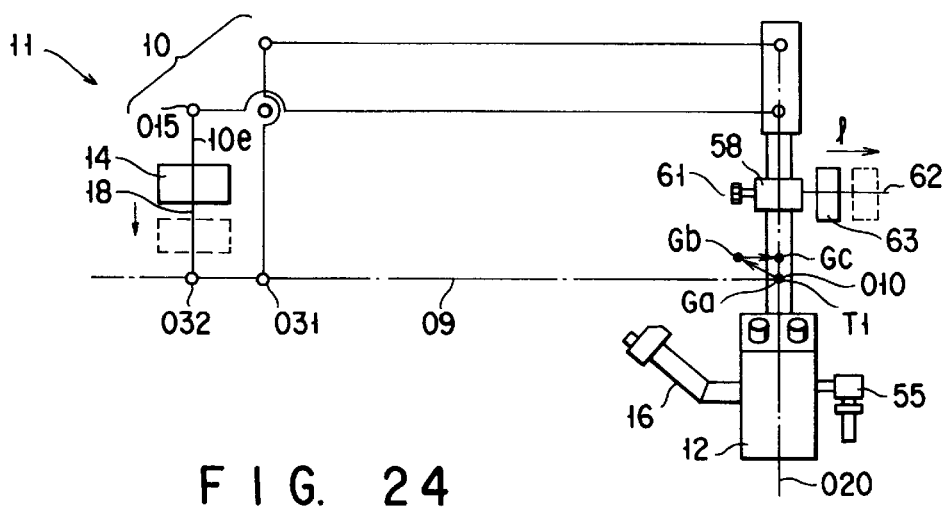
F I G. 24

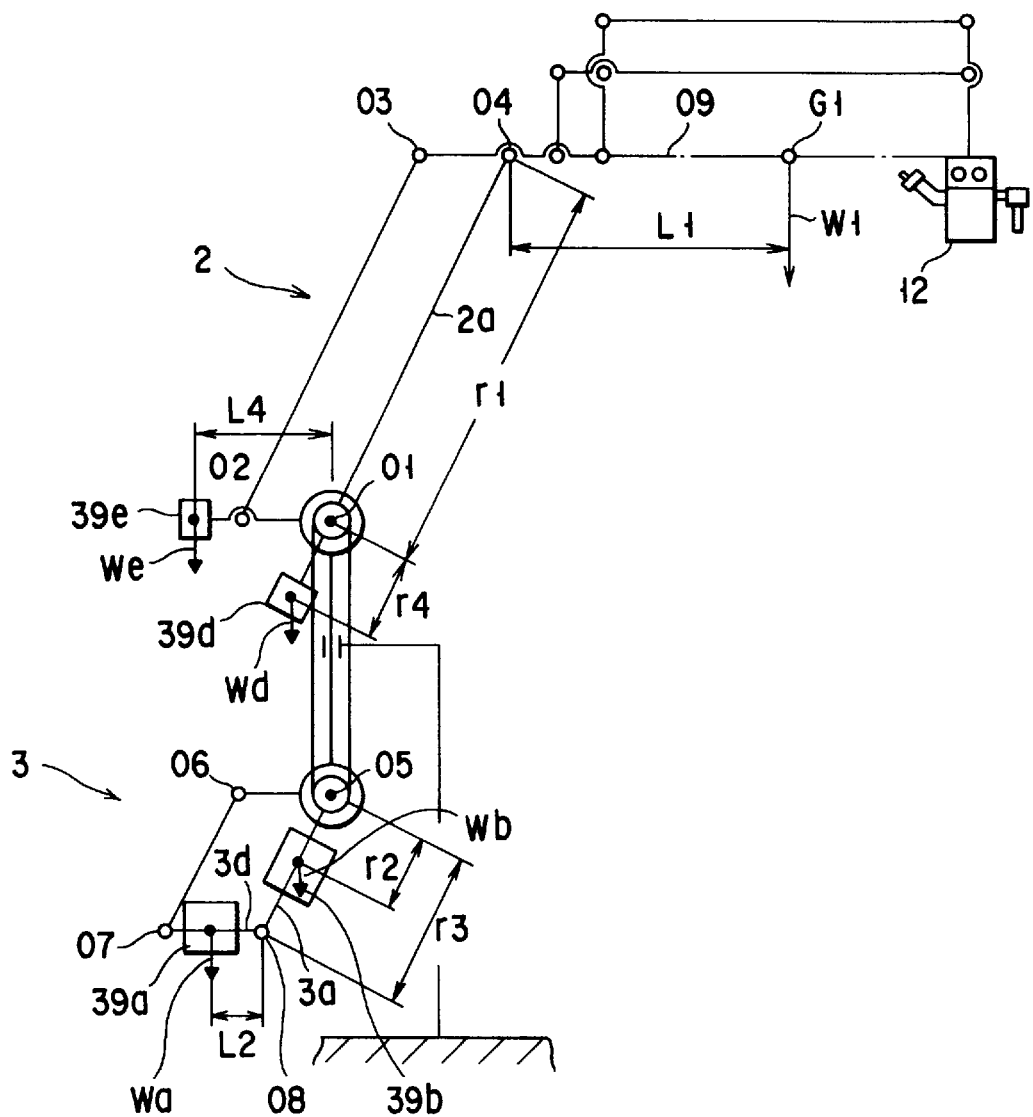
F I G. 29

SURGICAL MICROSCOPE UNIT

BACKGROUND OF THE INVENTION

1. Field of the Invention

The present invention relates to a surgical microscope unit used for microsurgery in the field of neurosurgery, for example, and more particularly to a surgical microscope unit having a microscope for observing portions to be surgically operated in a large scale and a supporting unit for moving the microscope to a position where a surgeon wants and changing the posture of the microscope as he wants.

2. Description of the Related Art

As surgical methods and surgical instruments have been developed, microsurgery has been performed frequently. In microsurgery, a surgical microscope unit of the above-mentioned type is used.

In neurosurgical operations, the positions and the angles (postures) of the microscope need to be changed frequently to observe the portions to be operated from various directions. Various supporting units have been proposed which move the microscopes to a required position quickly and accurately, allow the microscopes to take any necessary postures and can define the moving trajectories or loci of the microscopes.

Jpn. Pat. Appln. KOKAI Publication No. 5-168648 and Jpn. Pat. Appln. KOKAI Publication No. 5-215972 propose supporting units which can cause microscope bodies to tilt without moving observation points.

Jpn. Pat. Appln. KOKOKU Publication No. 63-36481 and U.S. Pat. No. 5,173,802 also disclose supporting units of this kind.

With the supporting unit disclosed in Jpn. Pat. Appln. KOKAI Publication No. 5-168648, however, the longitudinal frame of a front parallel linkage which is set to rotate the microscope body around its focal position when the microscope body is tilted is elongated and then the front parallel linkage projects largely to obstruct its operation. The tilting movement of the microscope body caused by the front parallel linkage is transmitted by another linkage to a rear parallel linkage disposed under the front parallel linkages. The provision of these extra linkage makes the structure of the supporting unit very complicated and limits its tilting range. When the field of vision is moved by tilting the microscope body not around the focal position but around a vicinity of the microscope body slightly, not only all of the linkages but also the counterweight are moved together. Thus, the supporting unit must be moved against a large inertia, thereby enlarging the operation force, resulting in greater difficulty of movement of the supporting unit.

Similarly, with the supporting unit disclosed in Jpn. Pat. Appln. KOKAI Publication No. 5-215972, the tilting movement of the microscope body is transmitted by a linkage. The structure is similarly complicated, the tilting range of the microscope body is small and a large operation force is required. Further, a weight for realizing horizontal balance is positioned at a place at which the weight largely projects toward the opposite side to the microscope body when the microscope is moved and obstructs the operation of the microscope body during surgery.

In t he supporting unit disclosed in Jpn. Pat. Appln. KOKOKU Publication No. 63-36481, a lower swing system and an upper swing system which comprise parallel linkages are supported on a support and at least one weight is carried on the lower swing system by a rod to maintain equilibrium of both swing systems. This supporting unit has a problem in that the balance weight and the rod for supporting the balance weight project rearward largely as the microscope body is moved, and they interfere with other instruments used during surgery and greatly obstruct the work of the surgeon and his assistants. The supporting unit has a further problem in that stability is not good because an axis for supporting the lower swing system on the support is positioned at a high level and thus the position of the center of gravity is high.

It is assumed that an arm portion extending from the portion of the axis to the portion of the rod is made short in order to reduce the amount of projection of the balance weight at the axis. With this arrangement, however, the balance weight projects upward as the swing system rotates downward. Thus, this movement greatly hinders the work of the surgeon and his assistants.

It is necessary to make the swing arm long to provide the microscope body with an ample tilting range when the position of the axis is lowered. In this case, however, the balance weight must be made large or a rod and an arm member for supporting the balance weight must be made large to maintain the balance of the swing system. In both cases, the amount of the projection of the balance weight is large. In any case, the amount of the projection of the balance weight cannot be made small.

The supporting device disclosed in U. S. Pat. No. 5,173, 802 differs from that disclosed in Jpn. Pat. Appln. KOKOKU Publication No. 63-36481 only in that the balance weight is directly connected to the arm member of the swing system.

With the supporting unit disclosed in Jpn. Pat. Appln. KOKAI Publication No. 5-168648, a lower swing system and an upper swing system which comprise parallel linkages are supported on a support and the tilting movement of the front parallel linkage, i.e., the microscope is transmitted to the axis of the parallel linkage of the lower swing system. This supporting unit has the same problems as those of the supporting unit of Jpn. Pat. Appln. KOKOKU Publication No. 63-36481 in that the counterweight largely projects at the axis of the parallel linkage and creates obstruction and in that stability is lowered because the axis is at a high level. In other words, the counterweight largely projects rearward as the microscope body is moved. Thus, the counterweight interferes with other instruments in the surgical operation room, a surgeon and his assistants, and the stability of the supporting unit is lowered.

It is desirable that the weight for maintaining the balance in a counterbalance type structure be disposed close to the pivot axis in order to reduce the inertia. However, the weight cannot effectively approach the pivot axis in the structures disclosed in Jpn. Pat. Appln. KOKOKU Publication No. 63-36481, U. S. Pat. No. 5,173,802 and Jpn. Pat. Appln. KOKAI Publication No. 5-168648, because the weight must be increased in order to cause the weight to approach the pivot axis in a balancing state. For this purpose, it is necessary that the weight be made of a material having a large specific gravity or that the weight itself be large. However, a large weight cannot solve the conventional problem in that it hinders the work of the surgeon and his assistants. Further, a weight having a large specific gravity is not ideal because such weights are expensive.

Although the conventional microscope unit can perform tilting movement around the observation points, its operation portion interferes with other instruments and obstructs the work of the surgeon and his assistants during surgery. Further, the microscope body requires a large operation force to be moved and is very difficult to operate.

SUMMARY OF THE INVENTION

The present invention was made under the above-mentioned circumstances and the object thereof is to provide a surgical microscope unit in which a balancing weight does not project even when the microscope unit is moved, and which is compact, has a small inertia and high stability and is operated by a small operation force.

The surgical microscope unit according to the present invention has a moving mechanism which supports a microscope body and which can move the microscope body three-dimensionally so that the microscope body is capable of tilting around three axes.

When the microscope body is moved three-dimensionally with the surgical microscope unit, the movement is transmitted from a first parallelogrammic linkage to a second parallelogrammic linkage through a first movement interlocking mechanism and a second movement interlocking mechanism. A counterweight provided on the second parallelogrammic linkage is moved in cooperation with the movement of the microscope body and the angular moments due to the movements of the microscope body are always canceled out. It is thus possible to make the second parallelogrammic linkage smaller than the first parallelogrammic linkage. Therefore, a small counterweight is sufficient.

According to the surgical microscope unit of the present invention the balancing weight does not project and a small operating region is provided even when the microscope body is moved, the inertia and operation force are small, and stability is high. In other words, the microscope body does not interfere with other instruments or obstruct the surgeon and his assistant during the surgical operation. This can greatly reduce fatigue of the surgeon.

A movement control mechanism may be provided to limit the moving locus of an tilting rod, whereby the microscope body can be moved along a predetermined path.

The movement control mechanism may be structured so that the moving path of the tilting rod, i.e., the moving path of the microscope body can be controlled easily and the control of the microscope body can also be achieved with ease.

In addition, the movement transmitting mechanism may be provided with a simple structure and may be used in an inexpensive surgical microscope unit.

An interlocking member and auxiliary counterweight may also be provided so that the counterweight can be made small to reduce inertia.

Still further, the mechanism for supporting the microscope body may be made compact although the microscope unit is provided with a mechanism for tilting the microscope body around observation point, and the microscope unit can be moved by a small force. In other words, the microscope body does not interfere with other instruments or obstruct the surgeon and his assistant during the surgical operation. This can greatly reduce fatigue of the surgeon.

The microscope body may also be permitted to rotate around a point corresponding to a pivotal point of the tilting rod and this point may be set on the optical axis of an objective lens so as to be disposed at or in the vicinity of the focal position.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWING

The accompanying drawings, which are incorporated in and constitute a part of the specification, illustrate presently preferred embodiments of the invention and, together with the general description given above and the detailed description of the preferred embodiments given below, serve to explain the principles of the invention.

FIGS. 7A and 7B are illustrative views showing the substantially vertical movement of the microscope body according to the first embodiment;

FIGS. 11 and 12 are views showing the relationship between the center of the rotating microscope body upon observing the deep portion of an object through an opening and the distance between the microscope body and the surface of the body of a patient to be observed;

FIG. 23 is a modeled view illustrating how to balance the first and second parallelogrammic linkages of the surgical microscope unit according to the third embodiment;

FIG. 24 is a modeled view illustrating how to balance inclination of the microscope body of the surgical microscope unit according to the third embodiment;

FIG. 29 is a modeled view how to balance the first and second parallelogrammic linkages of the surgical microscope unit.

DETAILED DESCRIPTION OF THE PREFERRED EMBODIMENTS

A first embodiment of the present invention will be described with reference to FIGS. 1 to 10. (Structure)

Figure 1:
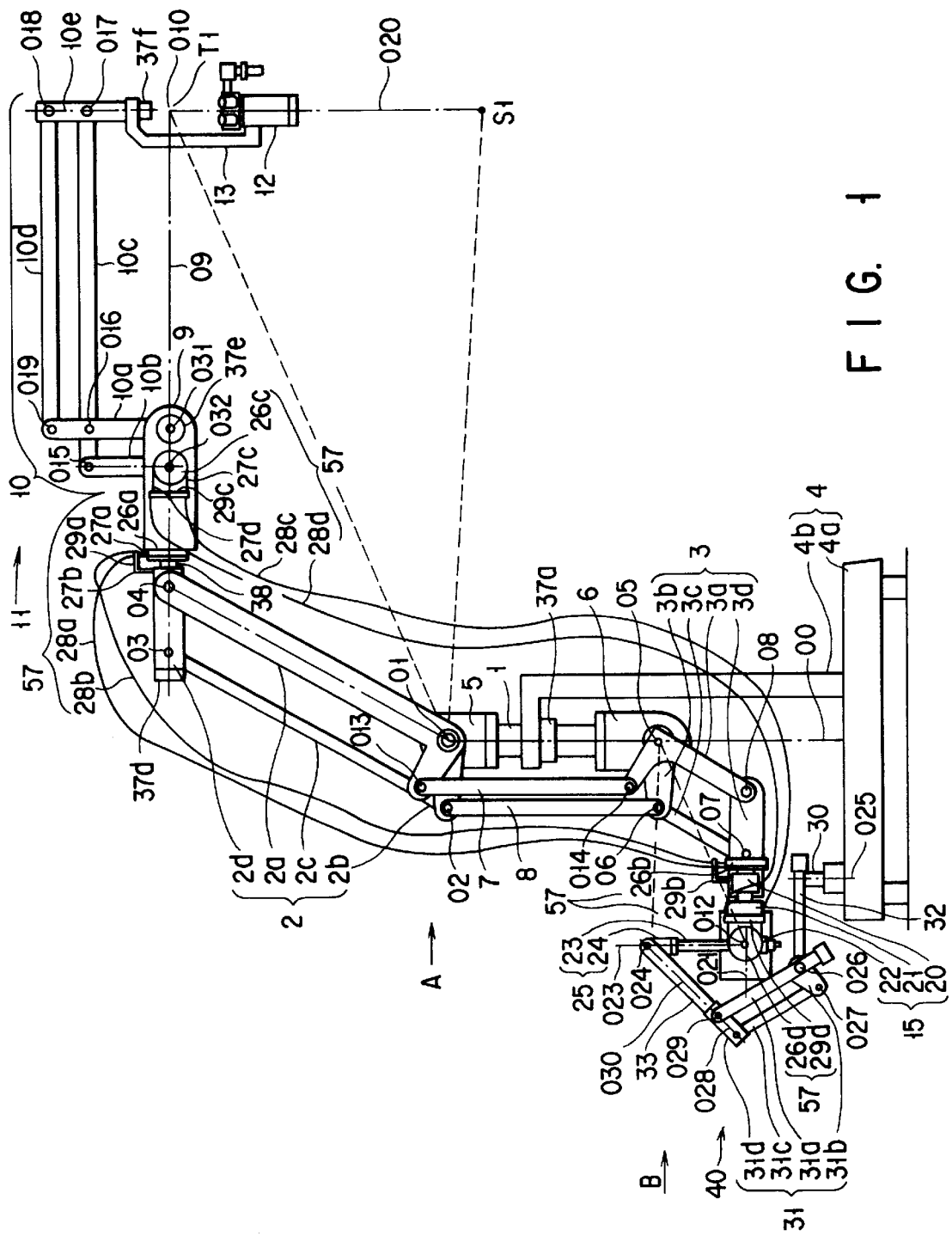
FIG. 1 is a general side view of the whole of a surgical microscope unit according to a first embodiment of the present invention.

FIG. 1 shows a general structure of the whole of a surgical microscope unit according to the first embodiment of the present invention. A supporting unit of the microscope unit has a support 1 supported on a supporting base 4 which comprises a bottom plate 4a having casters on its bottom surface and a stand 4b. The support 1 is provided on the upper end portion of the stand 4b so as to be rotatable around a vertical axis O0. A first parallelogrammic linkage 2 is connected to the upper portion of the support 1, and a second parallelogrammic linkage 3 is connected to the lower portion of the support 1.

The first parallelogrammic linkage 2 comprises arms 2a to 2d arranged to form a parallelogram and connected together so as to be rotatable around pivot axes O1 to O4 arranged parallel with each other. The linkage 2 is connected to the upper end portion of the support 1 by an upper supporting member 5 so as to be rotatable around the pivot axis O1. The pivot axis O1 is perpendicular to the vertical axis O0. The second parallelogrammic linkage 3 comprises arms 3a to 3d arranged to form a parallelogram and connected together so as to be rotatable around pivot axes O5 to O8 arranged parallel with each other. The linkage 3 is connected to the lower end portion of the support 1 by a lower supporting member 6 so as to be rotatable around the pivot axis O5. The pivot axis O5 is perpendicular to the vertical axis O0 and is parallel with the pivot axis O1. The first parallelogrammic linkage 2 and the second parallelogrammic linkage 3 are separately provided on the upper and lower portions of the support 1, respectively, and arranged in a similarly corresponding relationship and perform similarly interlocking deforming movement through a first interlocking mechanism and a second interlocking mechanism both being described later.

The arm 2a of the first parallelogrammic linkage 2 has an arm part bent at the lower end of the arm 2a through which the pivot axis O1 passes and projecting laterally from the arm 2a so that the body of the arm 2a and the arm part assume a generally L shape. The upper end of a first transmitting rod 7 is connected to the front end portion of the projecting arm part having a pivot axis O13 parallel with the pivot axis O1 so as to be rotatable around the pivot axis O13. In a plane parallel with the paper surface of FIG. 1, a line connecting the pivot axis O1 and the pivot axis O4 is perpendicular to a line connecting the pivot axis O1 and the pivot axis O13 in this embodiment. However, these lines are not limited to be arranged orthogonally. The arm 3a of the second parallelogrammic linkage 3 similarly has an L shape. The lower end of the first transmitting rod 7 is connected to the front end portion of its projection arm part so as to be rotatable around a pivot axis O14 parallel with the pivot axis O5. In a plane parallel with the paper surface of FIG. 1, a line connecting the pivot axis O5 and the pivot axis O8 is similarly perpendicular to a line connecting the pivot axis O5 and the pivot axis O14 in this embodiment. When, however, these lines are parallel with the arm part bent and projecting from the arm 2a of the first parallelogrammic linkage 2, the arrangement of the lines is not limited thereto.

In a plane parallel with the paper surface of FIG. 1, the line connecting the pivot axis O1 and the pivot axis O4 is always parallel with the line connecting the pivot axis O5 and the pivot axis O8, and lines connecting the pivot axes O1, O5, O14 and O13 in turn form a parallelogram.

In the embodiment, the arms 2a and 3a and the first transmitting rod 7 constitute a first interlocking mechanism for transmitting a rotational force and effecting interlocking movement.

Similarly, the pivot axis O2 of the arm 2b of the first parallelogrammic linkage 2 is rotatably connected to the pivot axis O6 of the arm 3b of the second parallelogrammic linkage 3 by a second transmitting rod 8. In a plane parallel with the paper surface of FIG. 1, a line connecting the pivot axis O1 and the pivot axis O2 is arranged to be always parallel with a line connecting the pivot axis O5 and the pivot axis O6. In this embodiment, the arms 2b and 3b and the second transmitting rod 8 constitute a second interlocking mechanism for transmitting a rotational force and effecting interlocking movement.

On an end of the arm 2d of the first parallelogrammic linkage 2 is provided a connecting block 9 which is supported rotatable around a pivot axis O9 arranged on a line which intersects with the vertical axis O0 and connects the pivot axis O2 and the pivot axis O4 in a plane parallel with the paper surface of FIG. 1. A third parallelogrammic linkage 10 is connected to the connecting block 9. In this arrangement, arms 10a to 10e and the connecting block 9 are connected together so as to be rotatable around pivot axes O15 to O19, O31 and O32, thereby to form a double parallelogrammic linkage. In this embodiment, the connecting block 9 and the third parallelogrammic line mechanism 10 form a first tilting arm 11 as an tilting mechanism which can tilt around two orthogonal pivot axes O9 and O10.

An observing optical axis of the microscope body 12 coincides with a pivot axis O20 on a line connecting the pivot axis O17 with the pivot axis O18 in a plane parallel with the paper surface of FIG. 1. The microscope body 12 is supported by a microscope body supporting arm 13 mounted on a downward projecting portion of the arm 10e so as to be rotatable around the pivot axis O20. The microscope body 12 is rotatable around the three axes - the pivot axis O9, the pivot axis O20 and an imaginary pivot axis O10 perpendicular to the paper surface of FIG. 1 and passing an intersection T1 of the pivot axis O9 and the pivot axis O20. The weight of the surgical microscope unit of this embodiment is distributed in such a manner that the angular moments due to the own weight of the microscope unit around the pivot axis O9, the pivot axis O10 and the pivot axis O20 are always zero.

To a fixing base 20 fixed to the arm 3d of the second parallelogrammic linkage 3 is connected a rotary block 21 which is supported rotatably around a pivot axis O21 which is in a plane parallel with the paper surface of FIG. 1, intersects with the vertical axis O0 and is parallel with the pivot axis O9. To the rotary block 21 is provided a seat 22 which is connected rotatably around the pivot axis O12 which is parallel with the pivot axis O10 and perpendicular to the pivot axis O21. In this embodiment, the fixing base 20, the rotary block 21 and the seat 22 constitute a second tilting arm 15 as an tilting mechanism.

One end of a slide rod 23 is connected to the seat 22. To the other end of the slide rod 23 is connected a joint 24 rotatable around a pivot axis O23 perpendicular to the pivot axis O12 in a plane parallel with the paper surface of FIG. 1. In this embodiment, the slide rod 23 and the joint 24 constitute an tilting rod 25 as an tilting mechanism. The weight is distributed so that angular moments due to the own weight around the pivot axis O21, the pivot axis O12 and the pivot axis O23 are always zero.

A flexible movement transmitting member is provided for directly transmitting a tilting movement of the microscope body 12 around the pivot axes O9 and O10 to the tilting rod 25 as a tilting movement around the pivot axes O21 and O12 at the same ratio. A pulley 26a as a rotary member coaxial with the pivot axis O9 is provided on the connecting block 9 of the first tilting arm 11. Ends of wires 27a and 27b are wound on the pulley 26a at its opposite sides and are fixed to the pulley 26a. The leading ends of the wires 27a and 27b are slidably inserted into flexible outer tubes 28a and 28b and guided thereby. One end portion of each of the outer tubes 28a and 28b is fixed to the arm 2d by a fixture 29a. The connecting block 9 is rotated by turning of the pulley 26a.

Similarly, the rotary block 21 of the second tilting arm 15 has a pulley 26b as a rotary member provided coaxially with the pivot axis O21. The other ends of the wires 27a and 27b extending through the outer tubes 28a and 28b are wound on the pulley 26b from the opposite sides thereof and fixed to the pulley 26b. The other ends of the outer tubes 28a and 28b are fixed to the fixing base 20 by a fixture 29b. The rotary block 21 is rotated by turning of the pulley 26b.

On the connecting block 9 and an arm 10b of the first tilting arm 11 is similarly provided a pulley 26c as a rotary member so as to be rotatable around a pivot axis O32. Wires 27c and 27d are wound at their end portions on the pulley 26c from its opposite sides and the front ends of the wires 27c and 27d are fixed to the pulley 26c. The wires 27c and 27d are inserted into other flexible outer tubes 28c and 28d and guided thereby. The end portions of the outer tubes 28c and 28d are fixed to the connecting block 9 by a fixture 29c. The connecting block 9 is rotated together with the pulley 26c.

Similarly, a pulley 26d as a rotary member is provided coaxially with the pivot axis O12 on a seat 22 of the second tilting arm 15. The wires 27c and 27d are wound at their other ends from the opposite sides and their front ends are fixed to the pulley 26d. The end portions of the outer tubes 28c and 28d are fixed to the rotary block 21 by a fixture 29d. The seat 22 of the second tilting arm 15 is rotated together with the pulley 26d.

The wires 27a and 27b are wound on the respective pulleys 26a and 26b in such a way that, when either one of the pulleys 26a and 26b is rotated, the other pulley is rotated in the same direction as said one pulley. The diameters of the pulleys 26a and 26b are equal to each other so as to provide the same rotation of angle.

Similarly, the wires 27c and 27d are wound on the respective pulleys 26c and 26d in such a way that, when either one of the pulleys 26c and 26d is rotated, the other pulley is rotated in the same direction as said one pulley. The diameters of the pulleys 26c and 26d are equal to each other so as to provide the same rotation of angle.

In this embodiment, the pulleys 26a to 26d, the wires 27a to 27d, the outer tubes 28a to 28d and the fixtures 29a to 29d constitute a movement transmitting mechanism 57. Each of the wires 27a to 27d is a single flexible elongated transmitting member extending through the respective one of the outer tubes 28a to 28d as guide means and is guided so as to reciprocate axially without occurring buckling and/or flexure. Each of the wires 27a to 27d may be a single wire or a strand with or without a core.

A vertical shaft 30 is supported on the base portion 4a of the supporting base 4 so as to be rotatable around a vertical axis O25. A fixing parallelogrammic linkage 31 comprises arms 31a to 31d which are connected together so as to be rotatable around parallel pivot axes O26 to O29 and connected to the vertical shaft 30 by a swing lever 32 provided rotatably around the pivot axis O26. The pivot axis O26 is perpendicular to the vertical axis O25. The vertical shaft 30 is provided with an electromagnetic brake for controlling (braking) its rotation around the vertical axis O25. A further electromagnetic brake which controls the rotation around the pivot axis O26 and will be described later is provided on the arms 31a and 31b.

One end of a rod 33 is connected to the upper end of the joint 24 of the tilting rod 25. The other end of the rod 33 is connected to an end of the arm 31d of the fixing parallelogrammic linkage 31. The tilting rod 25 is in a plane parallel with the paper surface of FIG. 1 and is connected to the respective portions on a line connecting the pivot axis O28 and the pivot axis O29.

One end of the rod 33 is connected to the joint 24 of the tilting rod 25 so as to be rotatable around the pivot axis O24 perpendicular to the pivot axis O23. In this embodiment, the vertical shaft 30, the fixing parallelogrammic linkage 31, the swing lever 32, the rod 33 and the electromagnetic brake which will be described later constitute a movement controlling mechanism 40. The weight of the movement controlling mechanism 40 is distributed so that the angular moments due to the own weight of the mechanism 40 around the pivot axes O25, O26 and O30 are always zero.

As shown in FIG. 1, pivot axes O1, O4, O5, O8, O10 and O12 are arranged in such a manner that a triangle formed by the pivot axes O1, O4 and O10 is similar to a triangle formed by the pivot axes O5, O8 and O12 in a plane parallel with the paper surface of FIG. 1 and including the vertical axis O0. The ratio of similarity is:

$$(\triangle O1, O4, O10)/(\triangle O5, O8, O12)=C$$

where C is a constant.

The structure will be described in detail. In FIG. 1, an electromagnetic brake 37a for electrically controlling the rotation of the support 1 with respect to the supporting base 4 is provided on the supporting base 4.

A first rotary rod 38 projecting from the connecting block 9 of the first tilting arm 11 is provided on a connecting portion between the first tilting arm 11 and the arm 2d of the first parallelogrammic linkage 2. The first rotary rod 38 is inserted in a bearing provided in the arm 2d and is rotatable around the pivot axis O9. An electromagnetic brake 37d is provided on the arm 2d and electrically controls the rotation of the first rotary rod 38 with respect to the arm 2d An electromagnetic brake 37e is provided on the connecting block 9, and electrically controls the rotation of the arm 10a with respect the connecting block 9.

An electromagnetic brake 37f is provided on the microscope supporting arm 13 and controls the rotation of the microscope supporting arm 13 with respect to the arm 10e.

Figure 2:
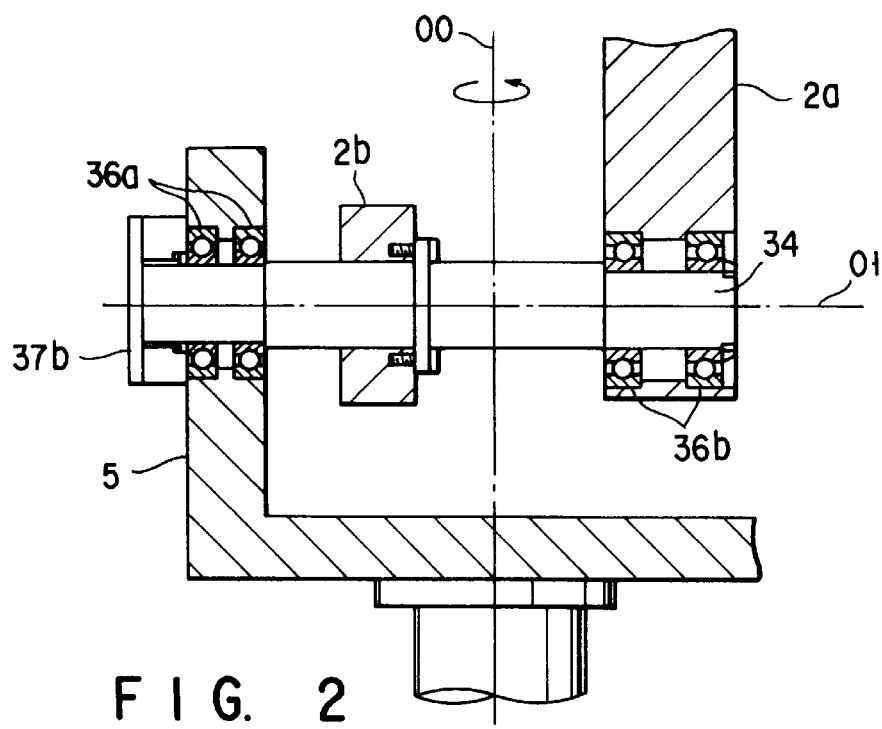
FIG. 2 is a cross-sectional view of a part of the microscope unit including a pivot axis O1 as viewed in the direction of an arrow a in FIG. 1.

Referring to FIG. 2, a portion of the upper supporting member 5 will be described in detail. FIG. 2 shows a cross section of a portion of the upper supporting member 5 including the pivot axis O1, as viewed in the direction A in FIG. 1.

An upper shaft 34 is supported on the upper supporting member 5 via a bearing 36a so as to be rotatable around the pivot axis O1. The upper shaft 34 can be electrically controlled by the electromagnetic brake 37b provided on the upper supporting member 5. The arm 2a is supported on the outer periphery of the upper shaft 34 by a bearing 36b so as to be rotatable around the pivot axis O1. The arm 2b is fixed to a flange portion formed on the upper shaft 34 by a set screw.

Figure 3:
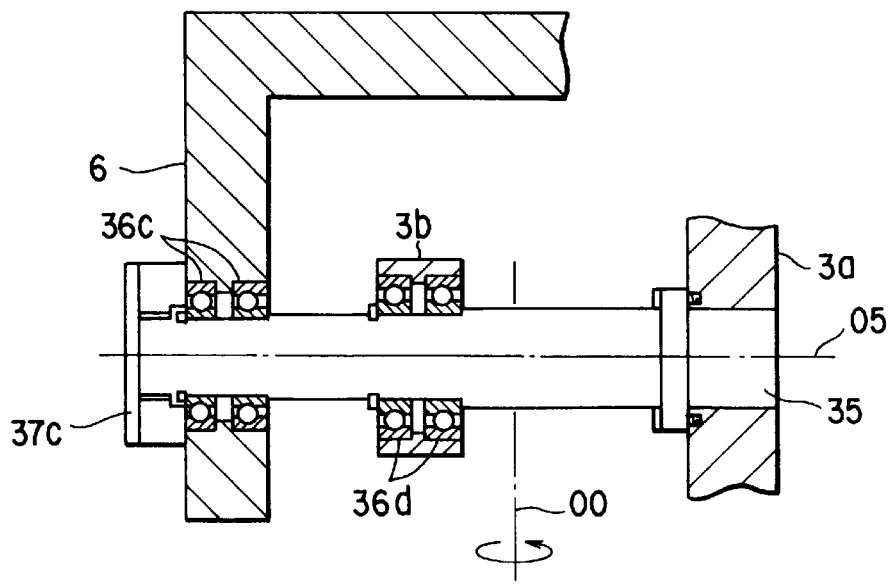
FIG. 3 is a cross-sectional view of a part of the microscope unit including a pivot axis O5 as viewed in the direction of an arrow b in FIG. 1.

With reference to FIG. 3, a part of the lower supporting member 6 will be described in detail. FIG. 3 is a cross-sectional view of a part including a pivot axis O5 as viewed in the direction of an arrow B of FIG. 1.

A lower shaft 35 is supported on the lower supporting member 6 by bearings 36c so as to be rotatable around the pivot axis O5. The lower shaft 35 is electrically controlled by an electromagnetic brake 37c provided on the lower supporting member 6. The arm 3a is fixed to the flange portion of the lower shaft 35 by a set screw. The arm 3b is supported on the outer periphery of the lower shaft 35 by bearings 36d so as to be rotatable around the pivot axis O5.

Figure 4:
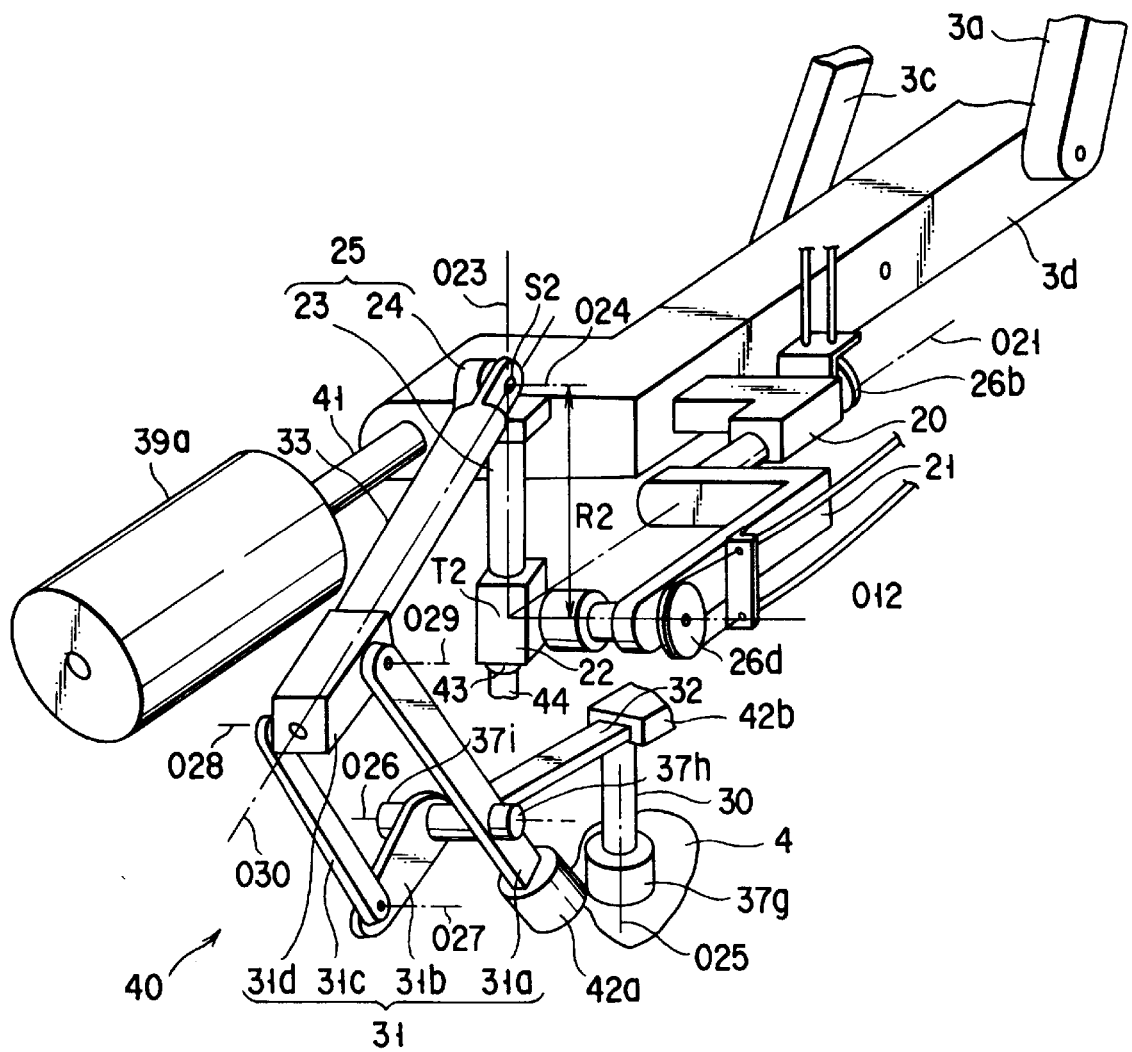
FIG. 4 is a detailed perspective view of a second parallel linkage, a second tilting arm, an tilting rod and a movement control mechanism of the surgical microscope unit according to the first embodiment.

With reference to FIG. 4, the structures of the second parallelogrammic linkage 3, the second tilting arm 15, the tilting rod 25 and the movement controlling mechanism 40 will be described in detail.

In FIG. 4, T2 is an intersection of the pivot axes O12 and O21, and S2 is an intersection of the pivot axes O23, O24 and O30. A screw shaft 41 is fixed to the arm 3d of the second parallelogrammic linkage 3. A counterweight 39a is supported on the screw shaft 41 so as to be movable in the axial direction. When the first parallelogrammic linkage 2 cooperates with the second parallelogrammic linkage 3, the counterweight 39a acts to distribute the weight so that angular moments around the pivot axes O0 and O1 are always zero.

In the figure, a tilting rod driving portion 43 is provided on the seat 22 and can electrically move the slide rod 23 of the tilting rod 25 in the direction of the pivot axis O23. 44 indicates a tilting rod position detecting portion which calculates a linear distance R2 between T2 and S2 by detecting the amount of drive of the tilting rod driving portion 43 connected to the tilting rod driving portions 43.

On the supporting base 4 is provided an electromagnetic brake 37g for electrically controlling the rotation of the vertical shaft 30 around the pivot axis O25 with respect to the supporting base 4. The arms 31a and 31b constituting the fixing parallelogrammic linkage 31 are respectively provided with electromagnetic brakes 37h and 37i for electrically controlling the arms 31a and 31b around the pivot axis O26 with respect to the swing lever 32.

To the arm 31a and the swing lever 32 are fixed auxiliary weights 42a and 42b for canceling out angular moments around the pivot axes O26 and O25.

Figure 5:
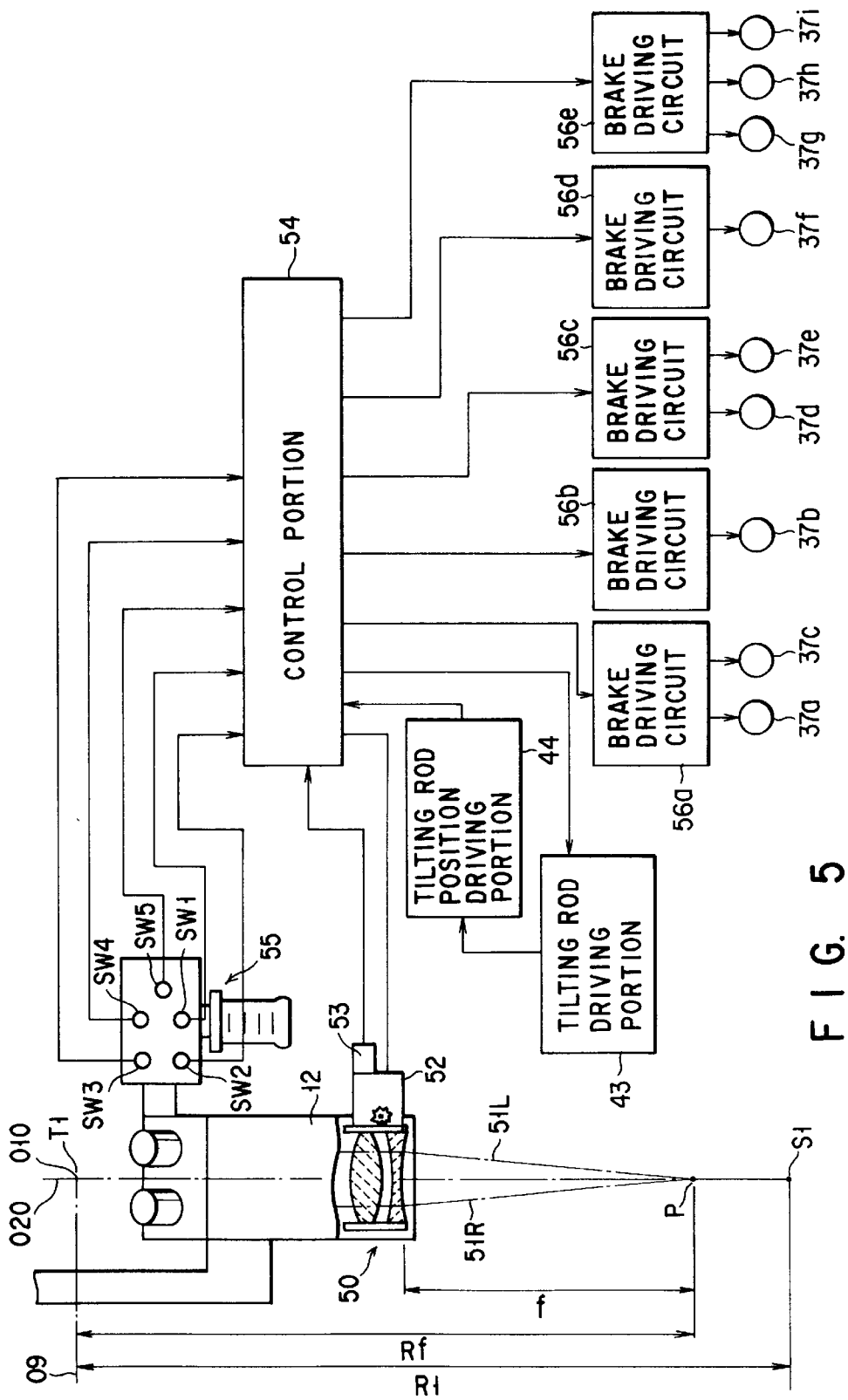
FIG. 5 is an illustrative view of a microscope body of the microscope unit and an electrical circuit of the surgical microscope unit according to the first embodiment.

With reference to FIG. 5, the structures of the microscope body 12 and the electric circuit will be described. An objective lens 50 is provided on right and left observation optical paths 51R and 51L comprising a zoom lens, a focusing lens and an ocular, not shown. The objective side focal length can be changed by varying the lens distances. The objective lens 50 is mechanically connected to an objective lens driving portion 52 and adjusts the focal distance. Objective lens position detecting means 53 such as an encoder is mechanically connected to the objective lens 50. T1 shows an intersection of the pivot axes O9, O10 and O20 and P designates an intersection of the observation optical axis (i.e., the pivot axis O20) and the focal plane of the microscope body 12, Rf indicates a linear distance between the points T1 and P, and f depicts a focal distance of the objective lens 50.

The objective lens driving portion 52 and the objective lens position detecting means 53 are connected to a control portion 54. The microscope body 12 is provided with a grip 55 which has a horizontal free switch SW1, a vertical free switch SW2, an all direction free switch SW3, a microscope body spherical surface tilting switch SW4, and a tilting center setting switch SW5 and the like. These switches are connected to the control portion 54. To the control portion 54 are connected the tilting rod driving portion 43 and a tilting rod position detecting portion 44.

Connected to the control portion 54 are the electromagnetic brakes 37a and 37c through a horizontal movement electromagnetic brake driving circuit 56a, the electromagnetic brake 37b through a vertical movement electromagnetic brake driving circuit 56b, the electromagnetic brakes 37d and 37e through a tilt electromagnetic brake driving circuit 56c, the electromagnetic brake 37f through an optical axis rotating electromagnetic brake driving circuit 56d, and the electromagnetic brakes 37g, 37h and 37i through a movement controlling mechanism electromagnetic brake driving circuit 56e.

(Operation)

The operation of the surgical microscope unit of the first embodiment will be described. With this surgical microscope unit, the three dimensional movements and tilting around the three orthogonal axes of the microscope body 12 (hereinafter referred to as the movements of six degrees of freedom), the movement in a substantially horizontal plane and the movement of a substantially vertical plane can be selected according to the types of surgery. The selection of them will be described in turn.

[Movements of six degrees of freedom]

When the all direction free switch SW3 of the grip 55 is depressed, the corresponding signal is inputted to the control portion 54. Signals are outputted from the control portion 54 to the horizontal movement electromagnetic brake driving circuit 56a, the vertical movement electromagnetic brake driving circuit 56b, the tilt electromagnetic brake driving circuit 56c, the movement controlling mechanism electromagnetic brake driving circuit 56e and the optical axis rotation electromagnetic driving circuit 56d, thereby to release the brake actions of all the electromagnetic brakes 37a, 37b, 37c, 37d, 37e, 37f, 39g, 37h and 37i.

When the brake action of the electromagnetic brake 37a is released, the support 1 becomes rotatable around the vertical axis O0 with respect to the support base 4. Thus, the microscope body 12 becomes rotatable around the vertical axis O0 with respect to the supporting base 4 through the first parallelogrammic linkage 2 and the first tilting arm 11.

Upon releasing the electromagnetic brake 37b as shown in FIG. 2, the arm 2b becomes rotatable around the pivot axis O1 with respect to the upper supporting member 5 in such a manner that the arm 2d becomes rotatable around the pivot axis O4 with respect to the arm 2a by maintaining the arm 2d parallel with the arm 2bAs a result, the microscope body 12 becomes rotatable around the pivot axis O4 with respect to the arm 2a through the first tilting arm 11.

When an electromagnetic brake 37c as shown in FIG. 3 is released, the arm 3a becomes rotatable around the pivot axis O5 with respect to the lower supporting member 6, and the arm 2a connected by the first transmitting rod 7 becomes rotatable around the pivot axis O1 with respect to the upper supporting member 5. Then, the microscope body 12 becomes rotatable around the pivot axis O1 with respect to the upper supporting member 5 through the first parallelogrammic linkage 2 and the first tilting arm 11.

Combination of rotations in the three directions of the microscope body 12 allows the microscope body 12 to move three-dimensionally.

Release of the electromagnetic brake 37d permits the first tilting arm 11 to rotate around the pivot axis O9 with respect to the arm 22d When the electromagnetic brake 37e is released, the arm 10a of the parallelogrammic linkage 10 becomes rotatable around the pivot axis O31 with respect to the connecting block 9, and the arm 10e connected by the arms 10b to 10d can tilt around the pivot axis O10 in a state in which the arm 10e is parallel with the arm 10a. When the electromagnetic brake 37f is released, the microscope body 12 becomes rotatable around the pivotal axis O20 of the arm 10e through the microscope supporting member 13. Thus, the microscope body 12 becomes rotatable around the intersection T1 of the pivot axis O9 and the pivot axis O10.

Since the brake actions of the electromagnetic brakes 37g, 37h and 37i of the movement control mechanism 40 are released, the vertical shaft 30 can be rotated around the pivot axis O25 with respect to support base 4 and the arms 31a and 31b of the fixing parallelogrammic linkage 31 can be rotated around the pivot axis O26 with respect to the swing bar 32. The rotation of the arm 31b around the pivot axis O26 with respect to the swing lever 32 is transmitted by the arm 31c to the arm 31d as its rotation around the pivot axis O29 with respect to the arm 31a. As a result, the rod 33 is rotated around respect to the arm 31th respect to the arm 31a and around the pivot axis O30 with respect to the arm 31d. In this state, no elements control the movement of the microscope body 12.

In other words, the movements of the microscope body 12 have six degrees of freedom which are given by the three dimensional movements and tilting movements around the three axes.

The action in corporation with the six degrees of freedom of the microscope body 12 will be described. As the arm 2b is rotated around the pivot axis O1 with respect to the upper supporting member 5, the arm 3b connected to the second transmitting rod 8 is rotated around the pivot axis O5 with respect to the lower supporting member 6 in a state in which the arm 2b is always parallel with the arm 2bThe arm 3d connected by the arm 3c to the arm 3b always in a parallel state is rotated around the pivot axis O8 with respect to the arm 3aIn this condition, the arm 3d is always kept parallel with the arm 2d As the arm 3a is rotated around the pivot axis O5 with respect to the lower supporting member 6, the arm 3d is rotated around the pivot axis O5 with respect to the lower supporting member 6. The tilting rod 25 is moved together with the arm 3d through the second tilting arm 15.

The arms 2a and 3a and the arms 2d and 3d are moved in a state in which the arms 2a and 3a are always kept parallel with the arms 2d and 3d. A triangle formed by connecting the pivot axes O1, O4 and O10 in a plane parallel with the paper surface of the drawing including the vertical axis O0 remains similar to a triangle formed by connecting pivot axes O5, O8 and O12. In this condition, the counterweight 39a supported by the arm 3d is moved to a position at which angular moments are always canceled out as the microscope 12 is moved.

The movements of the related parts allow the microscope body 12 to move at six degrees of freedom in a state in which the angular moments are always canceled out.

[Movements of a substantially horizontal plane]

Operation of the surgical microscope unit will described when the surgeon or the operator wants to move the microscope body 12 very often merely in the horizontal directions in the surgical operation of vertebra or the like. As the operator or the surgeon holds the grip 55 and pushes the horizontal free switch SW1, a signal is inputted to the control portion 54. Signals are outputted from the control portion 54 merely to the horizontal movement electromagnetic brake circuit 56a, the movement controlling mechanism electromagnetic brake driving circuit 56e and the optical axis rotating electromagnetic brake driving circuit 56d, and the brake actions of mere electromagnetic brakes 37a, 37c, 37f, 37g, 37g, 37h and 37i are released.

When the electromagnetic brake 37a is released, the support 1 becomes rotatable around the vertical axis O0 with respect to the supporting base 4, and the microscope body 12 becomes rotatable around the vertical axis O0 with respect to the floor through the first parallelogrammic linkage 2 and the first tilting arm 11.

Upon releasing the electromagnetic brake 37c, the arm 3a becomes rotatable around the pivot axis O5 with respect to the lower supporting member 6, and the arm 2a connected by the first transmitting rod 7 becomes rotatable around the pivot axis O1 with respect to the upper supporting member 5. Thus, the microscope body 12 becomes rotatable around the pivot axis O1 with respect to the upper supporting member 5 through the first parallelogrammic linkage 2 and the first tilting arm 11.

With the electromagnetic brake 37f released, the microscope body 12 becomes rotatable around the pivot axis O20 with respect to the arm 10e through the microscope body supporting arm 13.

Since the electromagnetic brakes 37g to 37i are also released, the movement controlling mechanism 40 does not control the movement of the microscope body 12.

In this condition, the electromagnetic brake 37b is fixed, and the rotation of the arm 2b of the first parallelogrammic linkage 2 about the pivot axis O1 with respect to the upper supporting member 5 is controlled so that the arm 2d always keeps a constant angle in a plane parallel to the paper surface of the drawing.

Figures 6A, 6B:
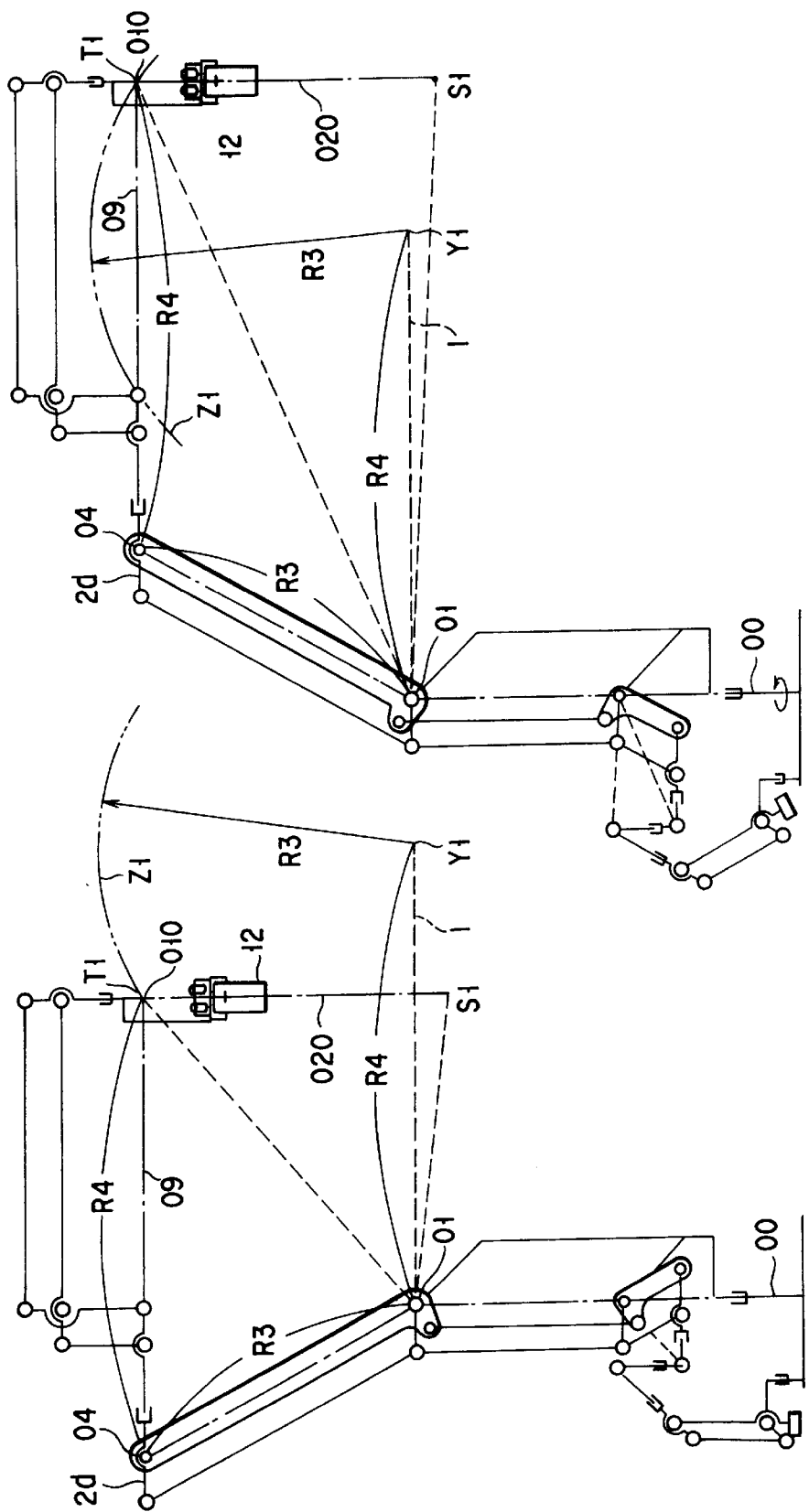
FIGS. 6A and 6B are illustrative views showing the substantially horizontal movement of the microscope body according to the first embodiment.

As shown in FIG. 6A, the arm 2d keeps its parallel state and is moved on an arc having a radius whose center is the pivot axis O1 and which is equal to a distance R3 between the pivot axis O1 and the pivot axis O4.

The intersection T1 of the pivot axis O9 and the pivot axis O10 moves on an arc Z1 having a radius equal to the distance R3 between the pivot axes O1 and O4 and having a center Y1 on a straight line I passing the pivot axis O1, parallel with the pivot axis O9 and separated by a distance between the pivot axis O4 and the pivot axis O10 from the pivot axis O1 toward the microscope body 12 in a plane parallel with the paper surface of the drawing.

As the brake action of the electromagnetic brakes 37d and 37e the first tilting arm 11 is fixed, the tilting movement of the microscope body 12 around the pivot axis O9 and the pivot axis O10 is controlled. Thus, the microscope body 12 is moved on an arcuated locus without being tilted.

Combination of this movement with rotation of the support 1 around the vertical axis O0 with respect to the supporting base 4 of the support 1 allows for the substantially horizontal movement. FIG. 6B shows the state of the microscope body 12 moved rightward from the state in FIG. 6A.

The microscope body 12 of this invention is moved on an arc in a substantially horizontal plane on the paper surface of the drawing, and thus the microscope body 12 is moved up and down along the observation optical axis. Since, however, the distance of the horizontal movement is very small, this vertical movement can be neglected.

[Substantial vertical movements]

In case of surgical operation of a deep portion through an opening in neurosurgery or the like, the microscope body 12 is sometimes wanted to move quickly in the directions of the observation optical axis without displacing the field of vision in order to watch a portion of the surgeon's side and a deeper portion. In this case, the operator or the surgeon pushes the vertical movement free switch SW2 of the grip 55. Then, a signal is inputted to the control portion 54 and signals are outputted merely to the vertical movement electromagnetic brake driving circuit 56b, the movement controlling brake driving circuit 56e and the optical axis rotating electromagnetic brake driving circuit 56d. The braking action of merely the electromagnetic brakes 37b, 37g, 37h, 37i and 37f is released.

When the electromagnetic brake 37b is released, the arm 2b becomes rotatable around the pivot axis O1 with respective to the upper supporting member 5, and the arm 2d becomes rotatable around the pivot axis O4 with respect to the arm 2a through the arm 2c in a state in which the arm 2d remains parallel with the arm 2bTherefore, the microscope body 12 becomes rotatable around the pivot axis O4 with respect to the arm 2a through the first tilting arm 11.

When the electromagnetic brake 37f is released, the microscope body 12 is made rotatable around the pivot axis O20 with respect to the arm 10e through the microscope body supporting member 13.

Because the electromagnetic brakes 37g to 37i are also released, the movement controlling mechanism 40 can follow any movement of S caused by the movement and the tilting of the tilting rod 25.

In this condition, the tilting of the microscope body 12 around the pivot axis O9 and the pivot axis O10 is controlled similarly to the movement in the substantially horizontal plane. The electromagnetic brake 37c is in a fixed state, and the rotation of the arm 3a of the second parallelogrammic linkage 3 around the pivot axis O1 is controlled. The rotation of the arm 2a of the first parallelogrammic linkage 2 connected to the first transmitting rod 7 around the pivot axis O5 is also fixed.

As shown in FIG. 7A, therefore, the arm 2d can be rotated merely around the pivot axis O4 in a plane parallel with the paper surface of the drawing. The intersection T1 of the pivot axis O9 and the pivot axis O10 can be moved merely on an arc Z2 whose center is on the pivot axis O4 and which has a radius equal to the distance R4 between the pivot axis O4 and the pivot axis O10. FIG. 7B shows the state of the microscope body 12 moved downward from the state in FIG. 6A.

The microscope body 12 of this invention is moved on an arc in the upward and downward directions, and thus the observation field of vision is displaced due to tilting of the observation optical axis. Since, however, the distance of the vertical movement required in surgical operation is very small, this displacement of the field of vision can be neglected.

[Tilting around a point on the observation optical axis]

When the microscope body spherical surface tilting free switch SW4 on of the grip 55 is pushed, a signal from the switch SW4 is inputted to the control portion 54, and signals are outputted merely horizontal movement electromagnetic brake driving circuit 56a, the vertical movement electromagnetic brake driving circuit 56b, the tilt electromagnetic brake driving circuit 56c and the optical axis rotating electromagnetic brake driving circuit 56d, whereby merely the brake action of the electromagnetic brakes 37a, 37b, 37c, 37d, 37e and 37f is released. From the standpoint of the six degrees of freedom as mentioned above, only the electromagnetic brake 37g, 37h and 37i are in a fixed state.

Figures 8A, 8B:
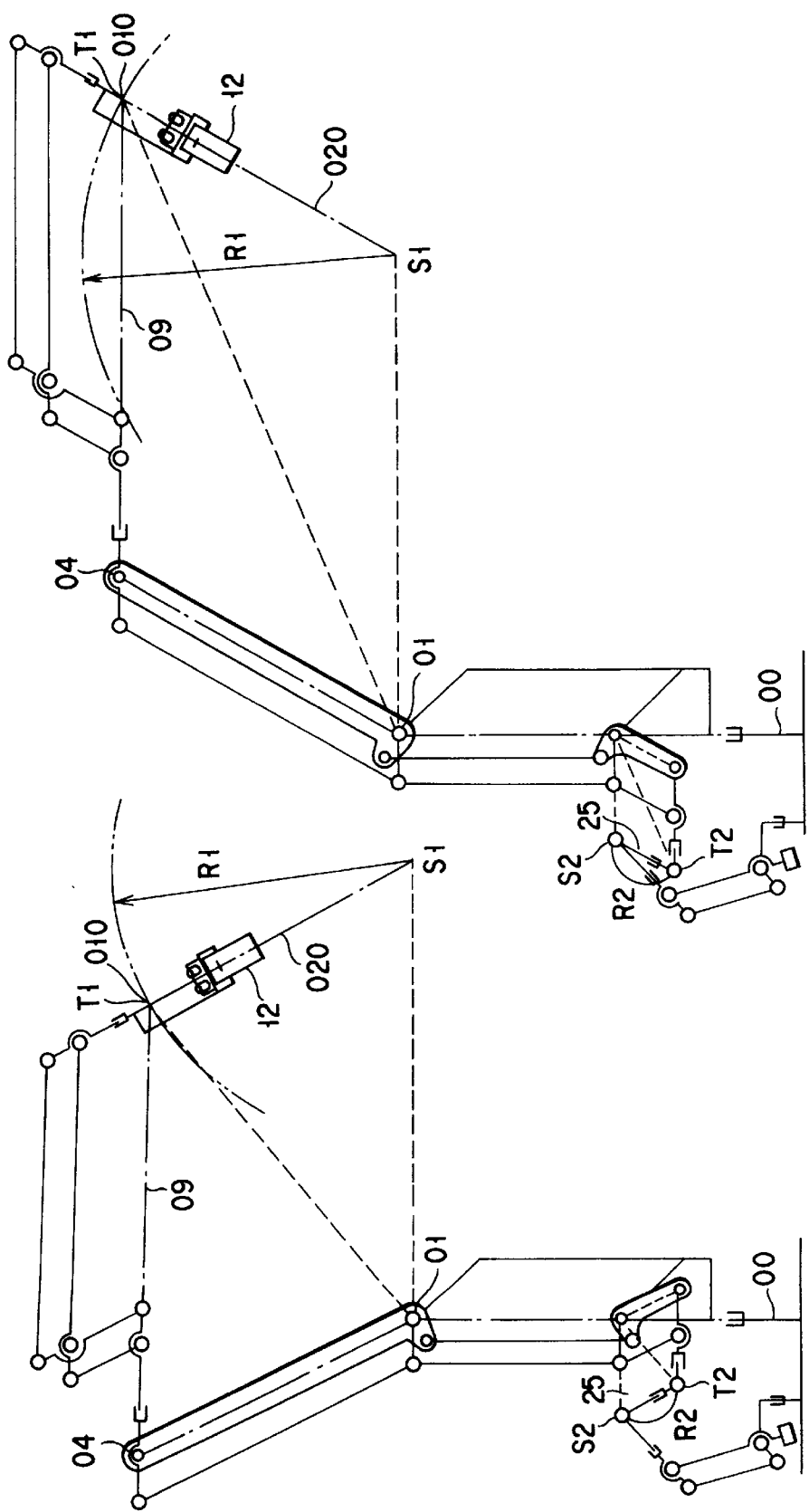
FIG. 8A and 8B are illustrative views showing the tilting movement of the microscope body according to the first embodiment around a point on the observation optical axis.
Figure 9:
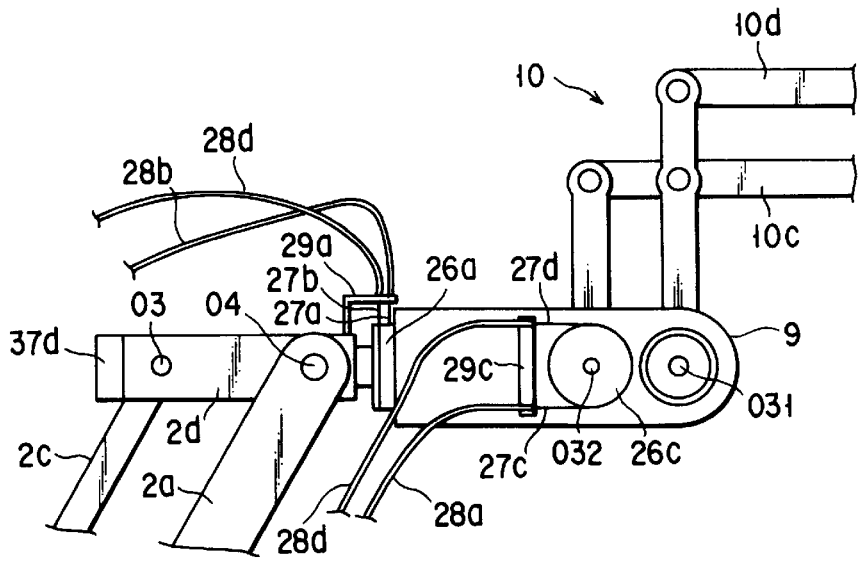
FIG. 9 is an enlarged view of a movement transmitting mechanism of the surgical microscope unit according to the first embodiment.
Figure 10:
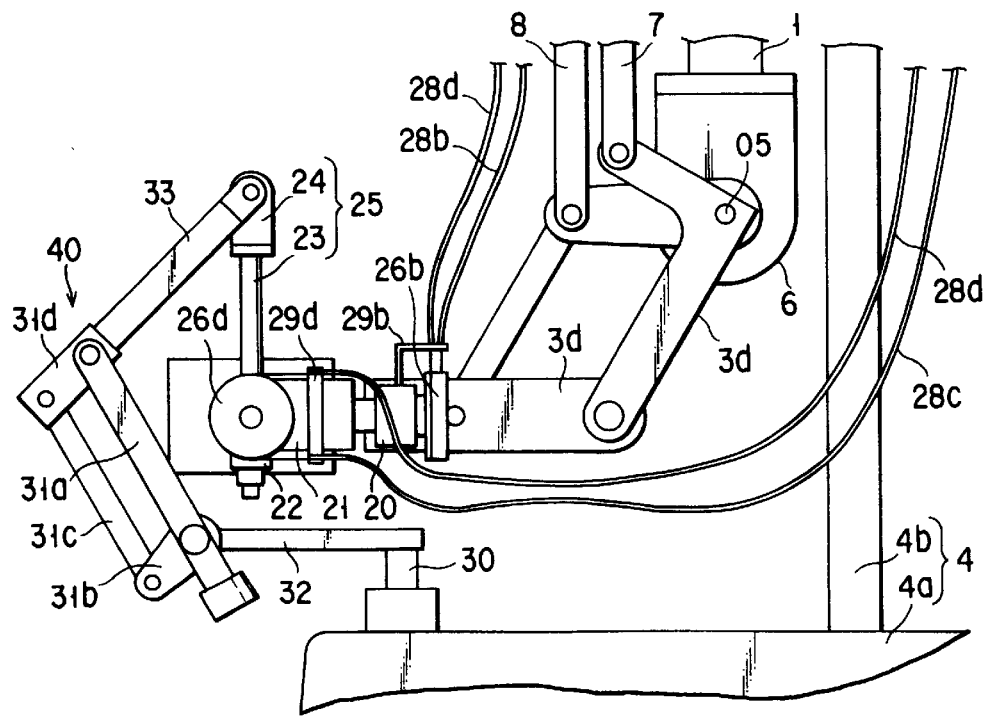
FIG. 10 is an enlarged view of a movement transmitting mechanism of the surgical microscope unit according to the first embodiment.

As shown in FIG. 8A, the movement of the point S2 of the tilting rod 25 is restricted, and the tilting rod 25 can tilt merely around S2. The point T2 moves on a spherical surface having a radius equal to a distance R2 between S2 and T2. The movement of the point T2 is transmitted in the similar manner as in the case of the arm action described before, and the intersection T1 of the pivot axes O9 and O10 is moved in the opposite direction by a distance equal to the moving distance of the intersection T2 multiplied by C which is the constant of the ratio between the above-mentioned similar triangles.

The tilting movement of the tilting rod 25 is transmitted to the microscope body 12 by the movement transmitting mechanism 57 employing the flexible wires 27a to 27d, thereby causing a relative movement of the microscope body 12. The operation will be described with reference to FIGS. 1 and 4.

As the tilting rod 25 is rotated around the pivot axis O12, the pulley 26d provided integrally with the seat 22 of the second tilting arm 15 is rotated integrally therewith. As a result, either one of the wires 27c and 27d is pulled in accordance with the rotational direction of the pulley 26d. The pulled wire has both ends fixed to the rotary block 21d and the connecting block 9 respectively by the fixture 29d and the fixture 29c, and slides in either one of the outer tube 28c and the outer tube 28d whose movement in the direction along the wire is restricted so that the pulled wire rotates the pulley 26c provided integrally with the arm 10b of the first tilting arm 11 in the same direction at the same angular speed as the pulley 26d. On the other hand, the not-pulled wire transmits the rotation of the pulleys 26d and 26c in a one-to-one relation without play. The rotation of the arm 10b is transmitted as rotation of the arm 10e around the pivot axis O10 by the parallelogrammic linkage 10. Thus, the microscope body 12 is rotated around the pivot axis O10 in the same direction at the same angular speed as the seat 22 tilts around the pivot axis O12.

As the tilting rod 25 is rotated around the pivot axis O21, the pulley 26b provided on the rotary block 21 of the second tilting arm 15 is rotated integrally therewith. Either one of the wires 27a and 27b is pulled in accordance with the rotational direction. The pulled wire has both ends fixed to the rotary fixing base 20d and the arm 2d respectively by the fixture 29b and the fixture 29a, and slides in either the outer tube 28a or the outer tube 28b whose movement in the direction along the wire is restricted so that the pulled wire rotates the pulley 26a arranged integrally with the connecting block 9 of the first tilting arm 11 in the same direction at the same angular speed as the pulley 26b. On the other hand, the not-pulled wire transmits the rotation of the pulleys 26b and 26a in a one-to-one relation without play. Thus, the microscope body 12 is rotated around the pivot axis O9 in the same direction at the same angular speed as the rotary block 21 tilts around the pivot axis O21.

In this connection, the pivot axis O23 of the tilting rod 25 is always maintained in parallel with the pivot axis O20 coaxial with the observation optical axis of the arm 10e.

In consequence, as shown in FIG. 8A, the microscope body 12 becomes rotatable around a point S1 as a center separated by a distance R2×C=RI from T1 on the pivot axis O20 coaxial with the observation optical axis. FIG. 8B shows a state in which the microscope body 12 is tilted rightward from the state shown in FIG. 8A.

When the tilting center point setting switch SW5 is pushed, an objective lens position signal from the objective lens position detecting potion 53 and a tilting rod position signal from the tilting rod position detecting portion 44 are inputted to the control portion 54. In the control portion 54, the distance Rf between T1 and the point P on the observation optical axis on the focal surface of the microscope body 12 is calculated from the objective lens position signal, and the distance R2 between T2 and S2 is calculated from the tilting rod position signal. A value R2×C=R1 (C being a similarity ratio of the triangles) and Rf are compared. A driving signal which moves the tilting rod 25 for equalizing the both values is inputted to the tilting rod driving portion 43. In the tilting rod driving portion 43, a motor (not shown) is rotated to move the slide rod 23 of the tilting rod 25 by a required distance on the pivot axis O23 in the required direction through a reduction device (not shown).

While the driving signal is being outputted to the tilting rod driving portion 43, a starting signal is outputted from the control portion 54 to the movement controlling mechanism electromagnetic brake driving circuit 56e. In this condition, the brake action of the electromagnetic brakes 37g, 37h and 37i are released but the other electromagnetic brakes 37a to 37f are fixed.

According to this operation, the surgeon or the operator causes a point, which he wants to select as a tilting center point of the microscope body 12, to coincide with the center of the observation field of vision and makes the point coincide with the focus (P in FIG. 5) by changing the focal length of the objective lens 50 by means of a switch (not shown). Thereafter, the tilting center point setting switch SW5 is pushed. Then, S1 is moved so as to coincide with P and the tilting center point of the microscope body 12 is automatically set to the required position.

(Technical effects of the embodiment)

This embodiment is constituted not by a single parallelogrammic link mechanism but by the separate first and second parallelogrammic linkages 2 and 3, one being disposed above the other one. Thus, the supported second parallelogrammic link mechanism 3 and the counterweight 39a which project when the microscope body 12 moves can be provided closer to the floor than the single parallelogrammic link mechanism as described above. In other words, the portion over the pivot axis O5 can be made compact so that a large space which is required for surgery can be obtained.

Since the counterweight 39a is disposed below, the center of gravity of the whole system is also lowered, whereby stability is increased and safety is enhanced.

Due to the fact that the projected length of the support 1 at the pivot axis O1 can be made shorter than the case in which a single parallelogrammic link mechanism is employed, the inertia moments of the moving portions can be reduced so that the moving portions operate lightly.

The first interconnecting mechanism and the second interlocking mechanism which interlock the movements of the first parallelogrammic linkage 2 and the second parallelogrammic linkage 3 are constituted by the arms 2a and 2b and the first transmitting rod 7 and by the arms 2b and 3b and the second transmitting rod 8, respectively. The mechanisms, therefore, do not exhibit play, which causes displacement of the field of vision, and have rigidity. Thus, they allow the moment of the first parallelogrammic linkage 2 to interlock with the movement of the second parallelogrammic linkage 3. Further, their structure is simple.

The movement transmitting mechanism 57 comprises the pulleys 26a to 26d, the wires 27a to 27d, the outer tubes 28a to 28d and the fixtures 29a to 29d. Thus, the movement transmitting mechanism 57 is light in weight and compact. This structure has the merits that the force (inertia) for moving the microscope body, for example, is smaller than the linkage formed by connecting links together in turn and the whole weight of the surgical microscope unit can be reduced.

Since the first tilting arm 11 is constituted by the parallelogrammic linkage 10, the angular moments around the pivot axis O9 and the pivot axis O10 produced when the microscope body 12 is connected to the first tilting arm 11 are canceled out by the arms of the first tilting arm 11. The movement transmitting member transmits mere displacement of tilting of the microscope body 12 and the tension due to the angular moments are not applied to the wire. Thus, friction between the wires and the outer tubes is small and the force for tilting the microscope body 12 is small. Even if the wires 27a to 27b are broken, no angular moment is produced in the microscope body 12. Thus, surgery can be continued in this condition.

When the deep portion of an opening whose open edge is taken as the tilting center point is observed with a stand device having an inclinable microscope body without moving the observing point as disclosed in Jpn. Pat. Appln. KOKAI Publication No. 5-168648, the microscope body 12 is moved to a position at which the tilting center point S1 separated by a distance Rp from the microscope body 12 toward the object is positioned at the center of the opening, and the focus is made to coincide with the observation point M of the deep portion.

When, however, the microscope body 12 is intended to be tilted around the observation point M of the deep portion as a center as shown in FIG. 12, the distance Rp from the microscope body 12 to the tilting center point S1 is fixed. Thus, the distance W between the microscope body 12 and the body surface is shortened and the operability for an operator with an operating tool is greatly deteriorated.

In case where the microscope body is changed from the state of FIG. 11 to the state of FIG. 12 during surgical operation, the surgeon or the operator must move the microscope body 12 in order to move the tilting center point S1 of the microscope body 12. It is very cumbersome for the surgeon to operate the microscope body 12.

On the other hand, this embodiment has a tilting rod driving portion 43 in which the intersection S2 of the pivot axes O12, O21 and O23 is movable on the pivot axis O23. Thus, the tilting center point S1 of the microscope body 12 becomes movable to an arbitrary point on the observation optical axis with respect to the microscope body 12 by moving the tilting rod driving portion 43 without changing the position of the microscope body 12. It is accordingly possible to change the tilting center point S1 of the microscope body 12 without varying the distance W between the microscope body 12 and the body surface of a patient, and the operability according to the condition of surgery is not deteriorated.

Further, this embodiment is provided with the objective lens position detecting portion 53, the tilting rod position detecting portion 44, an objective lens driving portion 52, a tilting rod driving portion 43 in which the intersection S2 of the pivot axes O12, O21 and O23 is displaceable on the pivot axis O23, and a control portion 54 to which signals are inputted from the objective lens position detecting portion 53 and the tilting rod position detecting portion 44 and from which signals for moving the tilting rod 25 by a required distance is outputted to the tilting rod driving portion 43. In this arrangement, the tilting center of the microscope body 12 is set automatically when the surgeon or the operator makes a point of the portion, which he wants to set as a center, coincide with the center of the field of vision and makes the focus coincide with the point enter. Then, he merely pushes the tilting center point setting switch SW5. In consequence, the tilting center point S1 can be set to the required position accurately and easily, and no cumbersome operation is needed. In addition, the surgical time is shortened and fatigue of the surgeon or the operator is reduced.

With the microscope unit described in Jpn. Pat. Appln. KOKAI Publication No. 5-168648, the microscope body can be tilted around a point as a center but the focus cannot be displaced horizontally without displacing the focus during surgical operation, or the microscope body cannot be moved in the axial direction quickly without displacing the field of vision during surgical operation.

The surgical microscope unit according to this embodiment which is supported by parallelogrammic linkages comprises the support 1 for rotatably supporting the first parallelogrammic linkage 2 on the vertical axis O0, the first parallelogrammic linkage 2 having the arms 2a and 2b and pivoted on the support 1 around the pivot axis O1, the electromagnetic brake 37a for controlling the rotation of the support 1, the electromagnetic brakes 37c and 37b for controlling the rotation of the arms 2a and 2b around the pivot axis O1, and the control portion 54 operated by interlocking the electromagnetic brakes 37a and 37c and operating the electromagnetic brake 37b independently. Thus, the microscope body can be not only tilted around the observation optical axis but also moved substantially horizontally and substantially vertically, whereby high versatility of surgery is attained and fatigue of the surgeon or the operator is reduced.

In the control unit described in Jpn. Pat. Appln. KOKAI Publication No. 5-215972, the movement controlling mechanism comprises a sliding unit, which can be locked electrically, and locking means. The locking means has two arms movable around the vertical axes in a horizontal plane. When the floor surface, i.e., the base legs and the whole control unit incline, the pivot axes for connecting the two arms are tilted so that the arms are automatically moved by their own weight. In this arrangement, the arms for supporting the microscope body is unbalanced and a large operating force is required in order to move the microscope body. Upon releasing the locking element, the field of vision is displaced due to the unbalance and the surgeon or the operator cannot concentrate his attention on surgery.

In the embodiment, the movement controlling mechanism 40 comprises the vertical shaft 30 rotatable around the pivot axis O25, deformable fixing parallelogrammic linkage 31 rotatably supported on the pivot axis O26 perpendicular to the vertical axis O25 and connected to the vertical shaft 30 through the swing lever 32, and the rod 33 connected to the arm 31d of the fixing parallelogrammic linkage and rotatable around the pivot axis O30 so that the angular moments around the vertical axis O25, the pivot axis O26 and the pivot axis O30 are canceled out. In this arrangement, therefore, no angular moments are produced around the pivot axes and the above-mentioned problems do not occur. In this connection, the surgeon or the operator can concentrate his attention on surgery.

Figure 13:
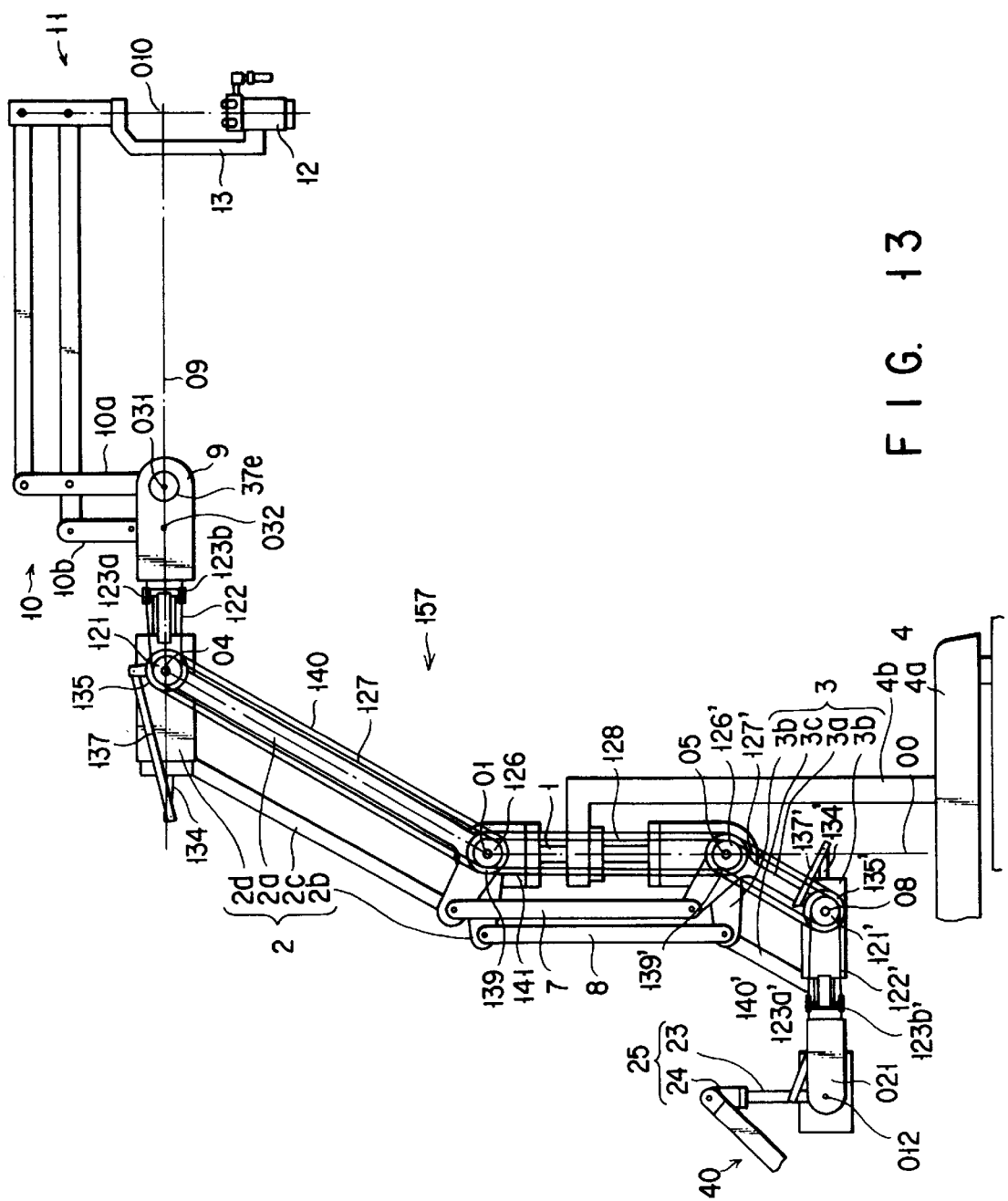
FIG. 13 is a general view of the whole of a surgical microscope unit using a movement transmitting mechanism according to another embodiment.
Figure 14:
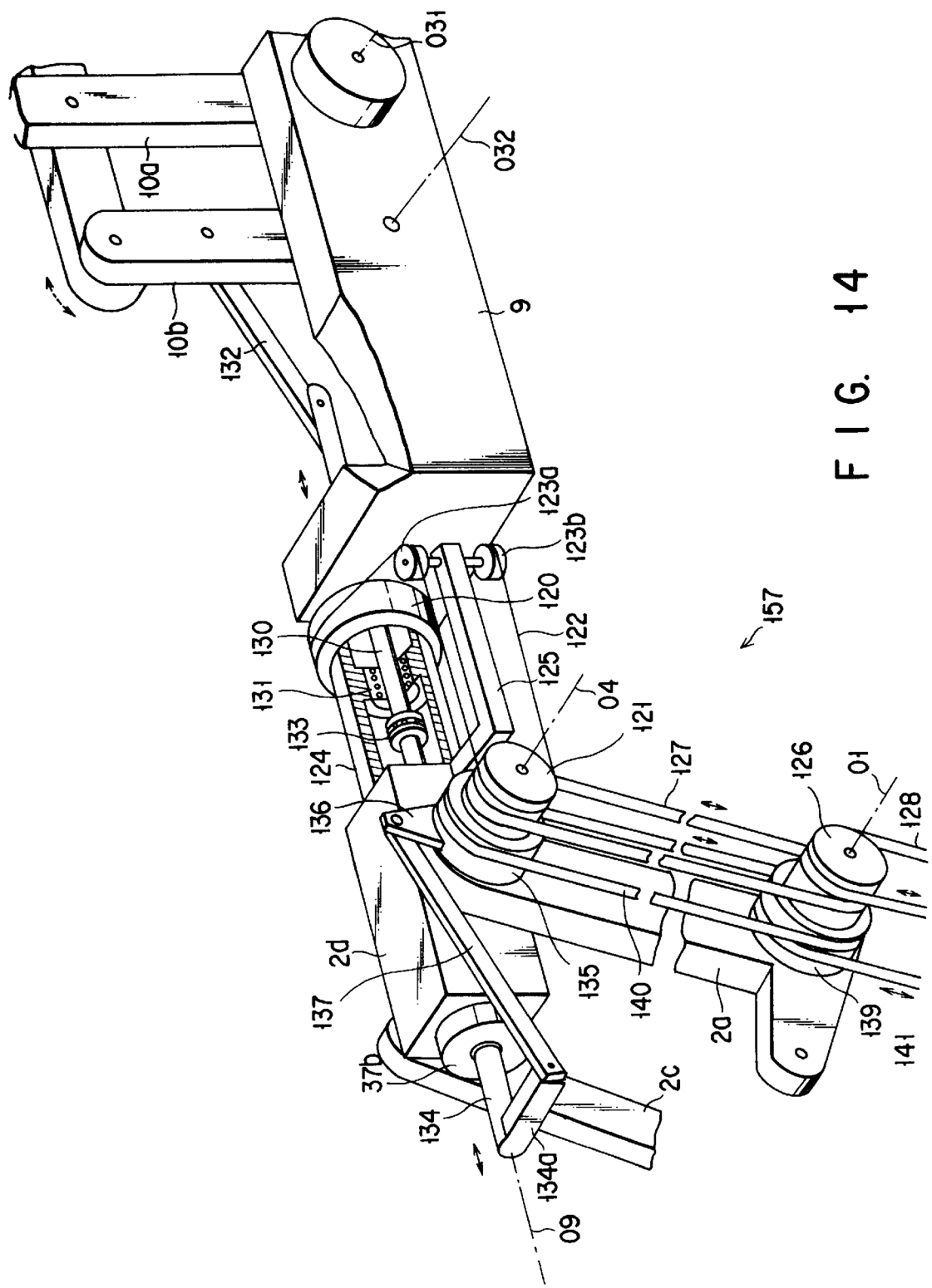
FIG. 14 is an enlarged view of the upper portion of the movement transmitting mechanism of FIG. 13.

FIGS. 13 and 14 show a movement transmitting mechanism 157 of another embodiment for transmitting the movements of the microscope body 12 around the pivot axes O9 and O10 to the tilting rod 25.

As shown in FIG. 13, the upper portion and the lower portion of the movement transmitting mechanism 157 of this embodiment are symmetrical with each other. Thus, the upper portion will be described chiefly.

As shown in FIG. 14, the movement transmitting mechanism 157 for transmitting the rotating movement of the microscope body 12 around the pivot axis O9 comprises a pulley 120 fixed to the connecting block 9 coaxially with the pivot axis O9, a pulley 121 rotatably connected to the arm 2d coaxially with the pivot axis O4 perpendicular to the pivot axis O9, a flexible wire 122 wound on the pulleys 120 and 121, and idling pulleys 123a and 123b for changing the directions of the wire 122 between the two pulleys 120 and 121 whose axes intersect perpendicularly.

The pulley 120 together with the connecting block 9 is rotatably mounted on a hollow cylindrical extension 124 projecting from the arm 2d The pulleys 123a and 123b are rotatably provided on an L-shaped bracket 125 fixed to the arm 2d and the movement of the pulley 120 is smoothly transmitted to the pulley 121 through the wire 122.

A pulley 126 is rotatably provided on the lower portion of the arm 2a coaxially with the pivot axis O1. A belt 127 is wound on the pulley 121 and 126 provided on the upper and lower end portion s of the arm 2a.

As shown in FIG. 13, the lower portion of the movement transmitting mechanism 157 has the similar structure to the upper portion thereof. The rotational movement is transmitted through a belt 128 from the pulley 126 to a pulley provided on the pivot axis O5 on the lower end portion of the support 1. In the similar way to the upper portion, the movement is transmitted from the pulley provided on the pivot axis O5 to the tilting rod 25 through a pulley provided on the pivot axis O8 and a belt. The parts of the lower portion are designated by referential signs given to the corresponding parts of the upper portion plus dashes "'", and detailed description thereof is omitted.

As the microscope body 1 is rotated around the pivot axis O9 as the center, the connecting block 9 is rotated, too. The rotational angle is transmitted from the pulley 120 to the pulley 121 through a wire 122 and then to the pulley 126 through the belt 127. The movement is transmitted from the pulley 126 to the tilting rod 25 by a belt 128 through the lower portion of the movement transmitting mechanism 157.

The movement transmitting mechanism 157 of this embodiment has a slide shaft 130 extending along the pivot axis O9 in order to transmit the rotation around the pivot axis O10 of the microscope body 12 (see FIG. 1) as the center to the tilting rod 25. The slide shaft 130 is slidably guided along the pivot axis O9 by a linear guide 131 provided in the extension 124 of the arm 22d The outer end of the slide shaft 130 is pivoted on a connecting rod 132 having one end pivoted on the arm 10b. The slide shaft 130 and the connecting rod 132 move in a plane parallel with the third parallelogrammic linkage 10. A first slider crank mechanism comprises the slider shaft 130, the arm 10b and the connecting rod 132.

As shown in FIG. 14, an end portion of the slide shaft 130 which is provided in the extension 124 is connected to a push rod 134 by a bearing 133 so as to be rotatable around the pivot axis O9. An extension 134a extends perpendicularly from the end portion of the push rod 134 projecting outward from the extension 124.

A pulley 135 is provided coaxially with the pivot axis O4 passing the pivotal portion of the arms 2a and 2d of the first parallelogrammic linkage 2. A lug 136 projects from the pulley 135. The front end portion of the lug 136 and the front end portion of the extension 134a of the push rod 134 are pivoted on a connecting rod 137. A second slider crank mechanism comprises the push rod 134, the lug 136 and the connecting rod 137 and moves in a plane parallel with the first parallelogrammic linkage 2.

To the lower end portion of the arm 2a is rotatably connected a pulley 139 coaxial with the pulley 126. A belt 140 is wound on the two pulleys 135 and 139 provided on the upper end portion and the lower end portion of the arm 2a, respectively. The movement of the pulley 139 is transmitted to the lower portion of the movement transmitting mechanism 157 through a belt 141. The parts of the lower portion are designated in FIG. 13 by referential signs given to the corresponding parts of the upper portion plus dashes "'", and detailed description thereof is omitted.

As the microscope body 12 is rotated around the pivot axis O10, the arm 10b of the third parallelogrammic linkage 10 is rotated around the pivot axis O32. The rotational movement of the arm 10b is converted into linear movements of the slide shaft 130 and the push rod 134 by the connecting rod 132. The linear movement of the push rod 134 is converted into a rotational movement of the pulley 135 by the connecting rod 137, and this rotational movement is transmitted to the lower portion of the movement transmitting mechanism 157 through a belt 140, a pulley 139 and a belt 141 so as to rotate the tilting rod 25 around the pivot axis O12.

Since the bearing 133 is provided between the slide shaft 130 and the push rod 134, the rotational movement of the connecting rod 9 is not transmitted to the push rod 134 even when the connecting block 9 is rotated around the pivot axis O9. Thus, the movement of the first slider crank mechanism comprising the arm 10b, the connecting rod 132 and the slide shaft 130 does not interfere with the movement of the second slider crank mechanism comprising the push rod 134, the connecting rod 137 and the pulley 135. The first and second slider crank mechanisms can move around the pivot axis O9 independently from each other.

A second embodiment of the present invention will be described with reference to FIGS. 15 to 18.
(Structure)

Figure 15:
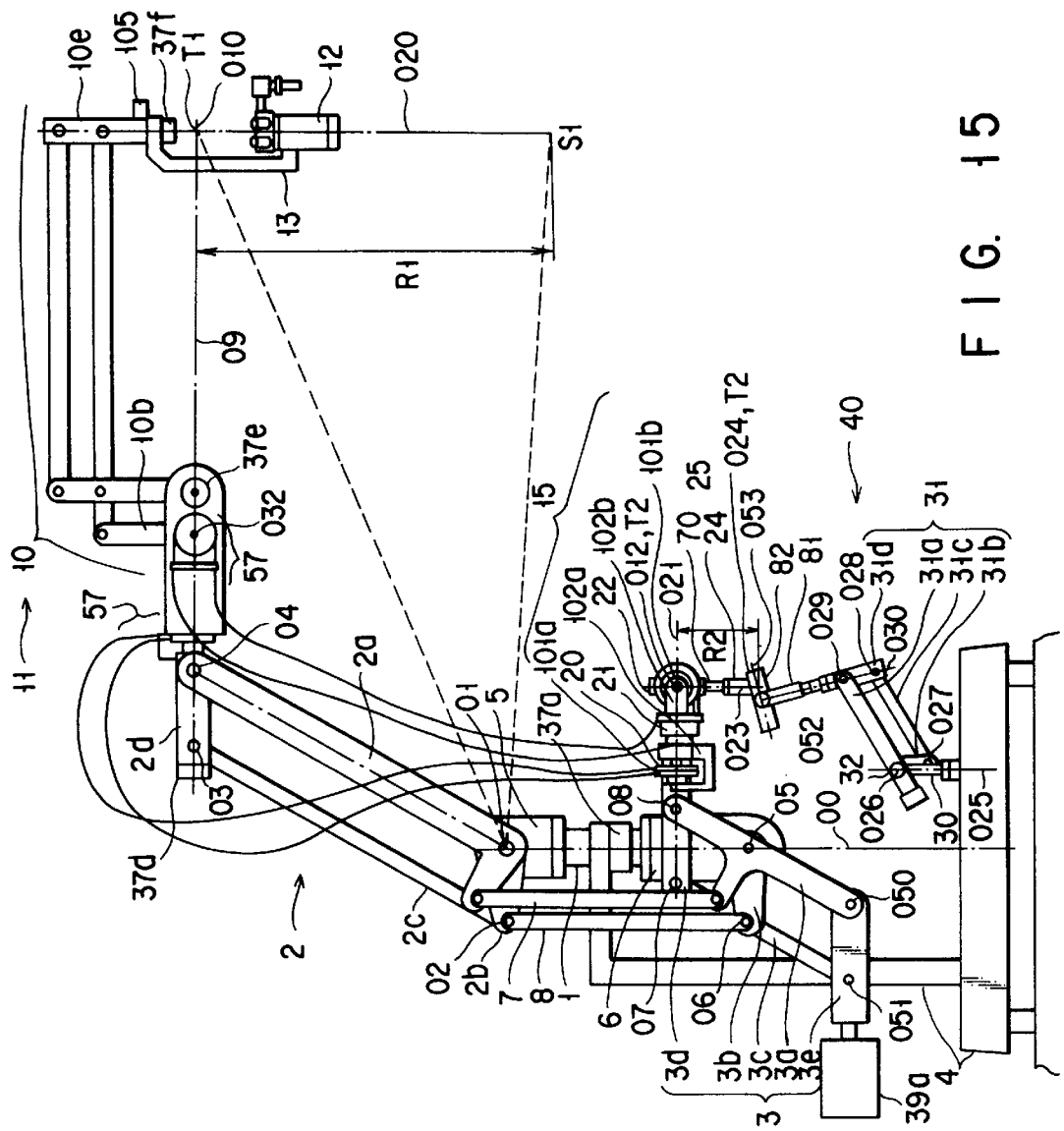
FIG. 15 is a general side view of the whole of a surgical microscope unit according to a second embodiment of the present invention.

FIG. 15 shows a general structure of the whole of the surgical microscope unit according to the second embodiment. This unit has a second parallelogrammic linkage 3, a movement controlling mechanism 40 and electrical arrangements for them which are different from those of the first embodiment.

A supporting base 4, a support 1, a first parallelogrammic linkage 2, an upper supporting member 5 and a lower supporting member 6 have the same structures as those of the first embodiment.

A second parallelogrammic linkage 3 comprises four arms 3a to 3d connected together so as to be rotatable around parallel pivot axes O5 to O8. The arm 3a extends toward the opposite side of the pivot axis O8 with respect to the pivot axis O5. The arm 3a is on the straight line passing the pivot axis O5 and the pivot axis O8. An arm 3e is connected, at a portion opposite to the pivot axis O8 with respect to the pivot axis O5, to the front end of this extended portion so as to be rotatable around a pivot axis O50 parallel with the pivot axis O5. An arm 3c extends toward the opposite side of the pivot axis O7 with respect to the pivot axis O6 and is on a straight line passing the pivot axis O6 and the pivot axis O7. The arm 3e is connected, at a portion opposite to the pivot axis O7 with respect to the pivot axis O6, to the front end of the extended portion so as to be rotatable around a pivot axis O51 parallel with the pivot axis O6. A line connecting the pivot axis O5 and the pivot axis O6 is parallel with a line connecting the pivot axis O50 and the pivot axis O51 in a plane defined by the parallelogrammic linkage which is parallel with the paper surface of the drawing. The arm 3d is disposed in a position turned by 180 degrees from the position of the arm 3d of the first embodiment. A counterweight 39a is connected to the arm 3e in a similar way to the arrangement of the first embodiment.

A first interlocking mechanism and a second interlocking mechanism of the second embodiment comprise arms 2a and 3aa first transmitting rod 7 and arms 2b and 3b and a second transmitting rod 8, respectively, similarly to the first embodiment.

A first tilting arm 11 constituted by a parallelogrammic linkage 10 and a movement transmitting mechanism 57 have the same structures as those of the first embodiment.

A second tilting arm 15 connected to the arm 3d which is turned by 180 degrees from the position of that of the first embodiment. The second tilting arm 15 has a tilt driving portion 102a provided on a fixing base 20 for electrically rotating the rotary block 21 around the pivot axis O21, and an electromagnetic clutch 101a provided on the fixing base 20 for electrically connecting the tilt driving portion 102a to or disconnecting the same from the rotary block 21 in addition to the elements of the second tilting arm of the first embodiment.

On the rotary block 21 are provided a tilt driving portion 102b electrically rotated around the pivot axis O12, and an electromagnetic clutch 101b for electrically connecting the tilt driving portion 102b to or disconnecting the same from the seat 22.

The tilting rod 25 has the same structure as that of the first embodiment.

Figure 16:
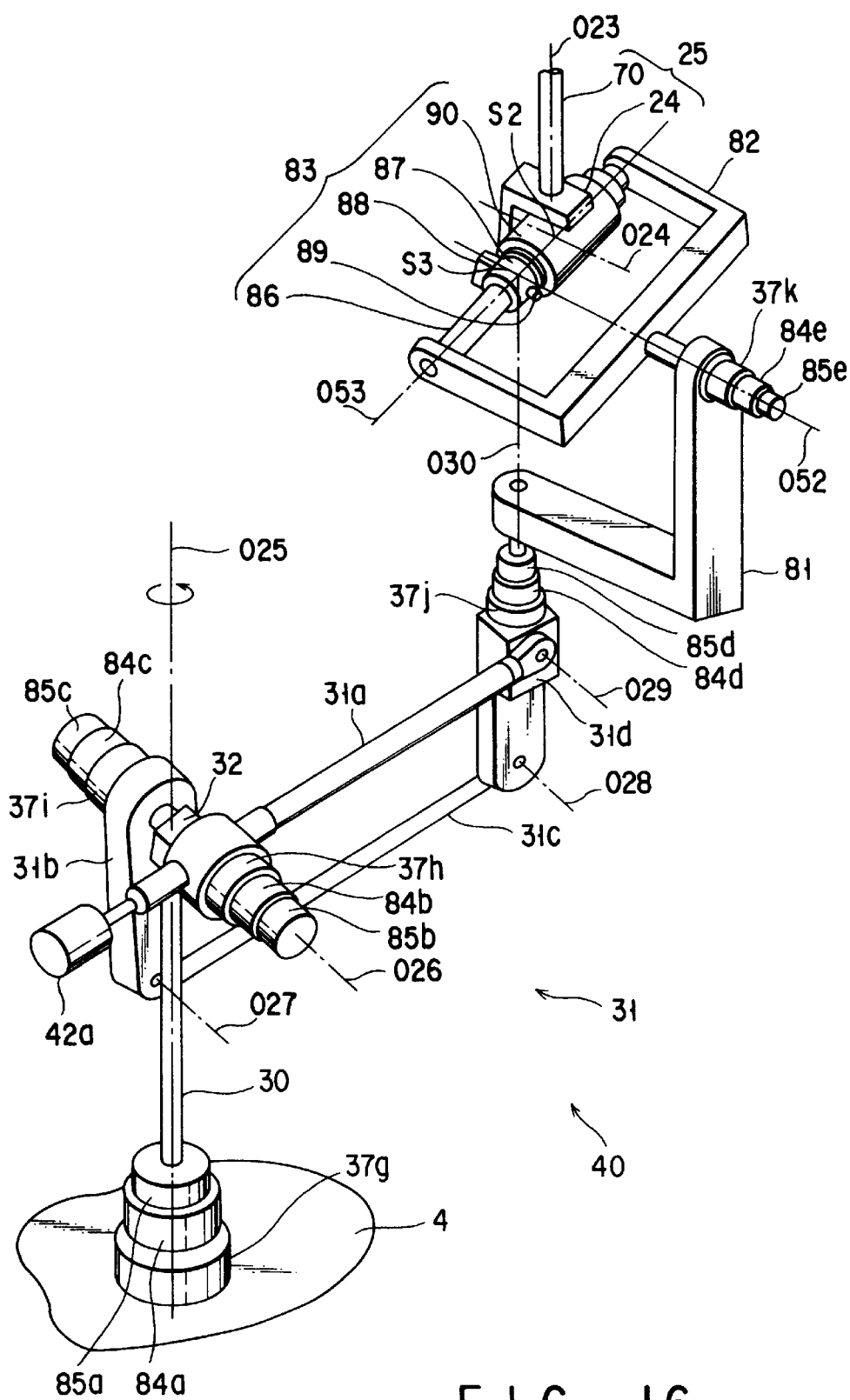
FIG. 16 is a detailed perspective view of a movement controlling mechanism of the surgical microscope unit of the second embodiment.

As shown in detail in FIG. 16, a fixing parallelogrammic linkage 31 is connected to a vertical shaft 30 supported on the supporting base 4 so as to be rotatable around the vertical axis O25. The fixing parallelogrammic linkage 31 comprises arms 31a to 31d connected together so as to be rotatable around the parallel pivot axes O26 to O29 and is connected to the vertical shaft 30 through a swing bar 32 so as to be rotatable around the pivot axis O26. The pivot axis O26 and the vertical axis O25 intersect with each other at right angles.

An L-shaped arm 81 is rotatably supported on the arm 31d around the pivot axis O30 in a plane including a vertical axis O25 and parallel with the paper surface of the drawing. A U-shaped arm 82 is supported on the L-shaped arm 81 so as to be rotatable around a pivot axis O52 intersecting at right angles with the pivot axis O30 and is also rotatable around a pivot axis O53 intersecting at right angles with the pivot axis O52. The U-shaped arm 82 is connected to the joint 24 of the tilting rod 25 through connecting means slidable along the pivot axis O53 as will be described later so as to be rotatable around the pivot axis O24.

A movement controlling mechanism 40 of the second embodiment comprises the vertical shaft 30, the fixing parallelogrammic linkage 31, a swing bar 32, a rod 33, the L-shaped arm 81, the U-shaped arm 82, connecting means which will be described later, an electromagnetic brake which will be described later, angle detecting means which will be described later and a driving portion which will be described later. The weight of the movement controlling mechanism 40 is distributed so that the angular moments around the pivot axes O25, O26, O30, O52 and O53 due to its own weight are always canceled out.

Although differently directed in this embodiment from the case in the first embodiment, the pivot axes O1, O4, O5, O8, O10 and O12 are arranged in such a manner that a triangle defined by connecting the pivot axes O1, O4 and O10 in a plane including the vertical axis O0 and parallel with the paper surface of the drawing is similar to a triangle defined by connecting the pivot axis O5, O8 and O12 on the same plane. The similarity ratio is given by:

$$(\Delta O1, O4, O10)/(\Delta O5, O8, O12)=C$$

where C is a constant.

Each part will be described in detail. In FIG. 15, references 37a, 37d, 37e and 37f are electromagnetic brakes connected in a similar way to those of the first embodiment.

An upper supporting member 5 has a similar structure to that of the first embodiment shown in FIG. 2 and is provided with an electromagnetic brake 37b for electrically controlling the rotation of the arm 2b around the pivot axis O5 with respect to a lower supporting member 6.

A lower supporting member 6 has a similar structure to that of the first embodiment shown in FIG. 3 and is provided with an electromagnetic brake 37c for electrically controlling the rotating of the arm 3a around the pivot axis O5 with respect to the lower supporting member 6.

Microscope body angle detecting means 105 such an encoder is provided on the arm 10e of the first tilting arm 11 and is used for detecting the rotational angle of a microscope body supporting arm 13 around the pivot axis O20 with respect to the arm 10e.

The movement controlling mechanism 40 will be described in detail with reference to FIG. 16.

The vertical shaft 30 is provided with an electromagnetic brake 37g for electrically controlling the rotation of the vertical shaft 30 around the pivot axis O25 with respect to the supporting base 4. A driving portion 84a for electrically driving the vertical shaft 30 around the pivot axis O25 with respect to the supporting base 4 is provided on the supporting base 4 through an electromagnetic brake 37g. 85a denotes angle detecting means 85a such as an encoder for detecting a rotational angle of the vertical shaft 30 around the pivot axis O25 with respect to the supporting base 4. The arms 31a and 31b constituting the fixing parallelogrammic linkage 31 are provided with electromagnetic brakes 37h and 37i for electrically controlling the rotation of the arms 31a and 31b around the pivot axis O26 with respect to the swing lever 32. Driving portions 84b and 84c are used for electrically driving the arms 31a and 31b around the pivot axis O26 with respect to the swing lever 32. Angle detecting means 85b and 85c such as encoders intend to detect the rotational angles of the arms 31a and 31b with respect to the swing lever 32. An auxiliary weight 42a is provided on the arm 31a.

An electromagnetic brake 37j is provided for electrically controlling the rotation of the L-shaped arm 81 around the pivot axis O30 with respect to the arm 31d, and an electromagnetic brake 37k is applied to electrically control the rotation of the U-shaped arm 82 around the pivot axis O52 with respect to the L-shaped arm 81. A driving portion 84d performs the electrical drive for rotating the L-shaped arm 81 around the pivot axis O30 with respect to the arm 31d, and a drive portion 84e acts to electrically rotate the U-shaped arm around the pivot axis O52 with respect to the L-shaped arm 81. 85d indicates angle detecting means such as an encoder for detecting the rotational angle of the L-shaped arm 81 around the pivot axis O30 with respect to the arm 31d, and 85e depicts angle detecting means such as an encoder for detecting the rotational angle of the U-shaped arm around the pivot axis O25 with respect to the L-shaped arm.

A guide shaft 86 is provided on the U-shaped arm 82 coaxial with the pivot axis O53, and a slide ring 87 is mounted on the guide shaft 86 so as to be slidable along the pivot axis O53 without accompanying rotation. To the slide ring 87 are connected fixing means 88 such as a push-pull solenoid for controlling the movement of the slide ring 87 along the pivot axis O53 with respect to the guide shaft 86, and position detecting means 89 such as a linear encoder for detecting the axial position of the slide ring 87 on the pivot axis O53 with respect to the guide shaft 86.

A rotary ring 90 is mounted on the slide ring 87 so as to be rotatable around the pivot axis O53 and is connected to a joint 23 constituting the tilting rod 25 so as to be rotatable around the pivot axis O24. The pivot axis O53 intersects at right angles with the pivot axis O24.

Here, connecting means 83 comprises the guide shaft 86, the slide ring 87, the fixing means 8, the position detecting means 89 and the rotary ring 90.

In the figure, S2 shows an intersection of the pivot axes O23, O24 and O53, and S3 indicates an intersection of the pivot axes O30, O52 and O53.

Figure 17:
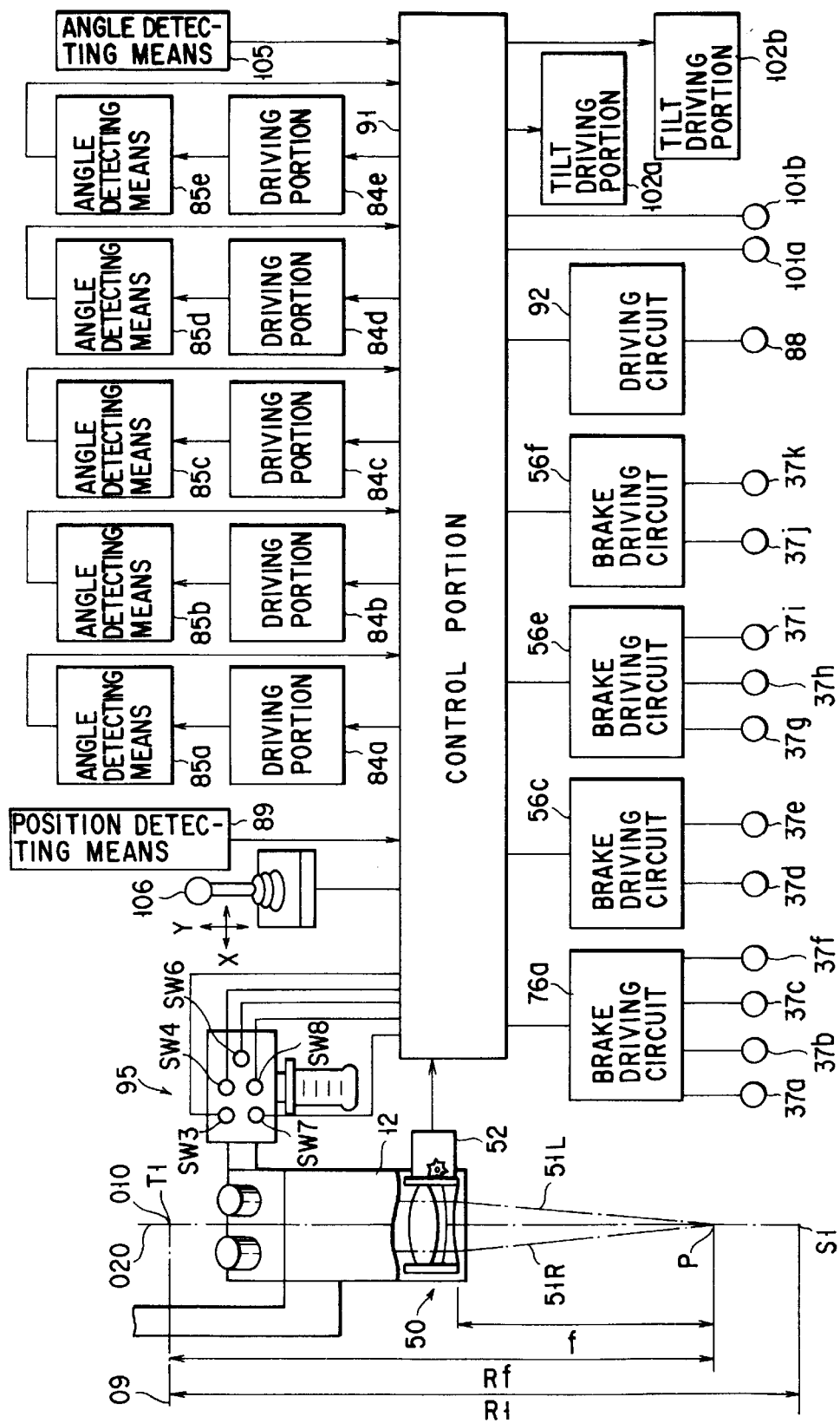
FIG. 17 is a view showing a microscope body of the microscope unit and an electric circuit of the microscope unit according to the second embodiment.
Figure 18:
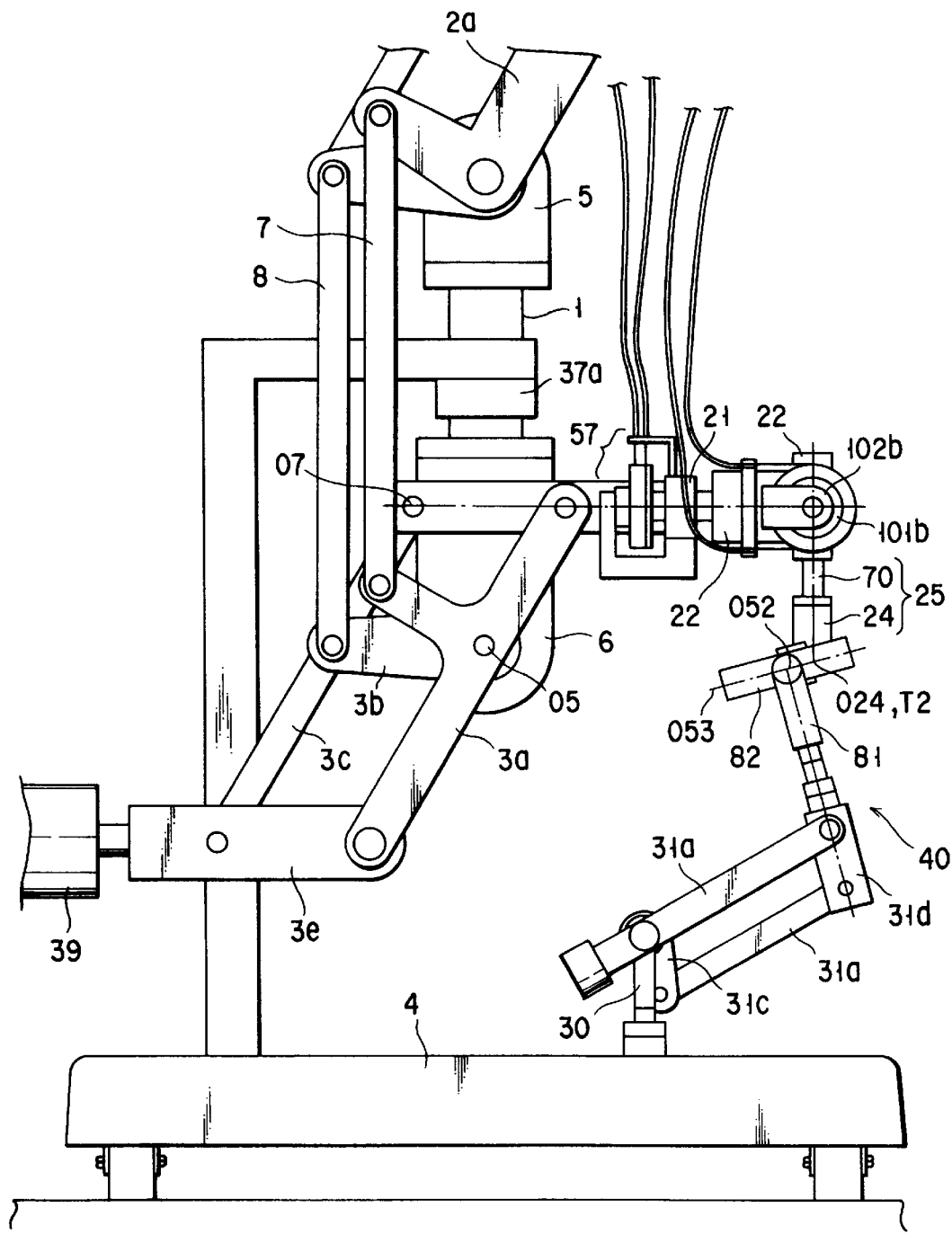
FIG. 18 is an enlarged view of a movement controlling portion of the surgical microscope unit according to the second embodiment.

FIG. 17 illustrates the structures of the microscope body 12 and an electric circuit.

An objective lens 50 similar to that of the first embodiment is mechanically connected to an objective lens driving portion 52.

The microscope body 12 can be tilted around a point S1 separated downward by a distance R1 from an intersection T1 of the pivot axes O9 and O10 on the pivot axis O20. P indicates an intersection of the pivot axis 20 and the focal surface.

A control portion 91 has a memory circuit (not shown) and is connected to the objective lens driving portion 52. A grip 95 is connected to the microscope body 12 and has an all direction free switch SW3, a microscope body tilting switch SW4, a linear moving switch SW6, a displacement locus setting switch SW7 and a focal length resetting switch SW8. All these switches are connected to the control portion 91.

Electromagnetic brakes 37a to 37c are connected to a control portion 91 through a stand electric brake driving circuit 76a. The electromagnetic brakes 37d and 37e are connected to the control portion 91 through a tilt electromagnetic brake driving circuit 56c. Electromagnetic brakes 37g to 37i are connected to the control portion 91 through a movement controlling mechanism electromagnetic brake driving circuit 56e to the control portion 91. Fixing means 88 is connected to the control portion 91 through a fixing means driving circuit 92.

Rotational angle detecting means 85a to 85e, position detecting means 89 and driving portions 84a to 84e are connected to the control portion 91.

Electromagnetic clutches 101a and 101b, tilt driving portions 102a and 102b and microscope body angle detecting means 105 are also connected to the control portion 91. The electromagnetic latches 101a and 101b are connected only when signals are inputted from the control portion 91.

A joy stick 106 for allowing for the inputs of the X and Y directions is connected to the control portion 91, too.

(Operation)

The operation of this embodiment will be described.

With this embodiment, movements of six degrees of freedom and a tilting movement around a point on the observation optical axis of the microscope body are available. In addition, the movement merely on a straight line and the displacement of the field of vision are possible.

[Movements of six degrees of freedom]

When the all direction free switch SW3 on the grip 95 is depressed, a signal is inputted to the control portion 91 and the signals are outputted to the tilt electromagnetic brake driving circuit 56c and the movement controlling mechanism electromagnetic brake 56e, whereby only the electromagnetic brakes 37a to 37i are released. In this case, the electromagnetic clutches 101a and 10b are not operated. The tilt driving portion 102a is disengaged from the rotary block 21, and the tilt driving portion 102b is disengaged from the seat 22. Thus, the rotary block 21 can be rotated around the pivot axis O21 with respect to the fixing base 20, and the seat 22 can be rotated around the pivot axis O12 with respect to the rotary block 21.

When the electromagnetic brakes 37a, 37b and 37c are released, the support 1 is made rotatable around the pivot axis O0 with respect to the supporting base 4. The arm 2b of the first parallelogrammic linkage 2 becomes rotatable about the pivot axis O4 with respect to the lower supporting member 6. The arm 3a becomes rotatable around the pivot axis O5 with respect to the lower supporting member 6. These rotations are transmitted in the same manner as those of the first embodiment, and the microscope body 12 is made movable three-dimensionally.

As the electromagnetic brakes 37d, 37e and 37f are released, the microscope body 12 is rotated around the intersection T1 of the pivot axes O9, O10 and O20 in same manner as in the first embodiment.

Transmission of the tilting movement of the first tilting arm 11 to the tilting movement of the second tilting arm 15 is the same as that of the first embodiment, and the description thereof is omitted.

Since the electromagnetic brakes 37g, 37h and 37i are all released, no elements restrict the movement of the microscope body 12 as in the first embodiment, in this condition.

The microscope body 12 can be moved at six degrees of freedom due to the three-dimensional movement and the tilting movement around the three orthogonal axes.

The operation interlocking with the six degrees of freedom of the microscope body 12 is the same as that of the first embodiment. The arm 2a and the arm 3a are moved always in parallel with the arm 2d and the arms 3d and 3e. In a plane including the vertical axis O0 and parallel with the paper surface of the drawing, a triangle defined by connecting the pivot axes O1, O4 and O10 is kept similar to a triangle defined by connecting the pivot axes O5, O8 and O12 in the same plane. In this condition, the counterweight 39a supported on the arm 3e is moved to a position at which the angular moments of the microscope body 12 are canceled out.

The microscope body 12 can be moved at six degrees of freedom due to the movement of each part of it in a state in which the angular moments are always canceled out.

[Tilting movement around a point on the observation optical axis]

When the microscope body spherical surface free switch SW4 on the grip 95 is pushed, a signal is inputted to the control portion 91, and signals are outputted to the stand electromagnetic brake driving circuit 76a and the tilt electromagnetic brake driving circuit 56c. Then, only the electromagnetic brakes 37a to 37f are released, and the electromagnetic brakes 37g and 37k and the fixing means 8 are fixed. In this state, the electromagnetic clutches 101a and 101b are not operated. Tilt driving portion 102a is separated from the rotary block 21 and the tilt driving portion 102b is separated from the seat 22. Thus, the rotary block 21 is rotatable around the pivot axis O21 with respect to the fixing base 20 and the set 22 can be rotated around the pivot axis O12 with respect to the rotary block 21.

With the tilting rod 25 as shown in FIG. 15, therefore, the movement of the intersection S2 of the pivot axis O23 and O24 is restricted and only the tilting movement around S2 is allowed in the similar way to that of the first embodiment. The point T2 moves on the spherical surface having a radius equal to the distance R2 between S2 and T2. The movement of T2 is transmitted in the similar way to that of the first embodiment, and the intersection T1 of the pivot axes O9 and O10 is moved by a distance equal to the moving distance of T2 multiplied by "C" which is the similarity ratio of triangles as described before.

The tilting movement of the tilting rod 25 is transmitted so that the tilting rod 25 is always parallel with the pivot axis O20 coaxial with the observation optical axis in the similar way to that of the first embodiment.

As a result, the microscope body 12 can be tilted around the point S1 separated from T1 on the observation optical axis by a distance of R2×C=R1.

The movement of the observation field of view merely on the straight line defined by connecting two points which is specific to this embodiment will be described.

When the portion to be surgically operated is too wide to be observed in the observation field of vision under the microscope body 12 fixed at a point or when the observation is made by reciprocating the microscope unit between two separate points, the observation field of vision is set to be moved merely on a straight line connecting the two aimed points.

In order to do so, the surgeon or the operator depresses a focal length reset switch SW8 on the grip 95 at first. Then, signals from the focal length reset switch SW8 and from objective lens position detecting means 53 are inputted to a control portion 91, and the previously memorized tilting center point SI and a P which is the current focus are compared. A driving signal is outputted to an objective lens driving portion 52 so that the two points coincide with each other by changing the focal length of an objective lens 50.

Next, an all direction free switch SW3 is pushed. After the microscope body 12 is moved so that the focus coincides with the first aimed observation point as a center of the field of vision, the all direction free switch SW3 is released. Then, a moving locus setting switch SW7 is depressed once. A signal from the moving locus setting switch SW7 is inputted to the control portion 91. Positional signals from angle detecting means 85a to 84e and position detecting means 89 are inputted to the control portion 91. Three-dimensional coordinates (X1, Y1, Z1) of the point S2 are calculated in the control portion 91. The calculated values are stored in a memory circuit (not shown) in the control portion. Next, the all direction free switch SW3 is depressed in the same way as mentioned above. After the microscope body 12 is moved so that the focus coincides with the second aimed observation point as a center of the field of vision, the moving locus setting switch SW7 is depressed again. As described above, positional signals from the angle detecting means 85a to 85e and from the position detecting means 89 are inputted to the control portion 91 and three-dimensional coordinates (X2, Y2, Z2) of the point S2 are calculated in the control portion 91. The control portion 91 calculates the middle point PM (XM, YM, ZM) between the two points and a straight line passing a point (X1, Y1, Z1) and a point (X2, Y2, Z2) in the memories and given by the following equation (1):

$$(X - X1)/(X2 - X1) = (Y - Y1)/(Y2 - Y1) \quad (1)$$
$$= (Z - Z1)/(Z2 - Z1)$$

Then, the moving direction and the moving distance of the point S3 required for causing the intersection of the pivot axes O30, O52 and O53 to coincide with the coordinates (XM, YM, ZM) of the middle point PM are calculated. Driving signals according to the calculated values are outputted to the driving portion 84a to 84c. A tilting angle and a direction required for causing the pivot axis O53 coaxial with a guide shaft 86 to coincide with the straight line calculated from the equation (1) are calculated. Driving signals according to the calculated values are outputted to the driving portions 84d and 84e. An L-shaped arm 81 is rotated around the pivot axis O30 through a required angle, and a U-shaped arm 82 is rotated around the pivot axis O52 through a required angle. As a result of these actions, the line defined by connecting the point (Xl, Yl, Zl) and the point (X2, Y2, Z2) is made to coincide with the pivot axis O53, and the point S3 is made to coincide with the middle point PM.

In the next step, a linear movement switch SW6 is depressed. Then, a signal is inputted to the control portion 91, and fixing means 88 is released from the control portion 91 through a fixing means driving circuit 92. Signals are outputted from the control portion 91 to a stand electromagnetic brake driving circuit 76a and a tilt electromagnetic brake driving circuit 56c so as to release the braking action of the electromagnetic brakes 37a to 37c. Electromagnetic clutches 101a and 10b are not actuated in this condition. The tilt driving portion 102a is disengaged from the rotary block 21, and the tilt driving portion 102b is disengaged from the seat 22. The rotary block 21 is rotatable around the pivot axis O21 with respect to the fixing base 20, and the seat 22 is rotatable around the pivot axis O12 with respect to the rotary block 21.

The slide ring 87 becomes slidable along the guide shaft 86, and S2 becomes movable merely on the straight line defined by connecting the two points (X1, Y1, Z1) and (X2, Y2, Z2) on the pivot axis O53. Thus, the center point P of the observation field of view on the focal surface of the microscope body 12 becomes movable merely on the straight line defined by connecting the two previously set points.

The electric movement of the field of view will be described.

A joy stick 106 is provided on the floor surface so that the X direction is parallel with a plane including left and right optical axes 51R and 51L of the microscope body 12 during surgical operation. When the surgeon or the operator operates the joy stick 106 with the foot during the surgical operation, a signal is outputted from the joy stick 106 to the control portion 91. An angle signal is inputted from the microscope angle detecting means 105 to the control portion 91. An angle between the arm 10e and the plane including the left and right observation optical paths 51R and 51L of the microscope body 12 is calculated. At the same time, signals are outputted from the control portion 91 to the electromagnetic clutches 101a and 101b whereby the tilt driving portion 102a is connected to the rotary block 21 and the tilt driving portion 102b is connected to the seat 22. In this state, signals are outputted from the control portion 91 to a tilt electromagnetic brake driving circuit 56c and a movement controlling mechanism electromagnetic brake driving circuit 56e, and the brake action of the electromagnetic brakes 37d, 37e, 37f, 37g to 37i is released.

The control portion 91 composes the drives of the tilt driving portions 102a and 102b in two directions due to the signal in the operating direction of the joy stick 106 and information of the angle between the arm 10e and a plane including the left and right observation optical paths 51R and 51L of the microscope body 12. Then, the control portion 91 calculates the driving speeds of the tilt driving portion 102a and 102b required for tilting the tilting rod 25 in the same direction as the operating joy stick 106 is directed. The control portion 91 provides signals required for driving the tilt driving portions 102a and 102b at the required speeds.

Since the electromagnetic brakes 37g to 37i in the moment controlling mechanism 40 are released, the tilting movement of the tilting rod 25 is not restricted. The electromagnetic rakes 37d and 37f are released with the result that the microscope body 12 can be rotated around the pivot axes O9 and O10.

As the tilt driving portion 102a is driven, the rotary rod 21 is rotated around the pivot axis O21 with respect to the fixing base 20 through the electro-magnetic clutch 101a. Similarly, as the tilt driving portion 102b is driven, the seat 22 is rotated around the pivot axis O12 with respect to the rotary block 21 through the electromagnetic clutch 101b. The rotation of the rotary block 21 and the seat 22 is transmitted by the movement transmitting mechanism 57 to the connecting block 9 as the rotation around the pivot axis O9 with respect to the arm 2d and to the arm 10b as the rotation around the pivot axis O32 with respect to the connecting block 9.

In consequence, the microscope body 12 is rotated around the pivot axes O9 and O10 in the same direction as the operating direction of the joy stick 106.

In this embodiment, the guide shaft 86 has a linear shape but may have a proper shape according to the type of surgical operation. In neurosurgery, for example, the guide shaft 86 may have an arcuated shape which is curved along the head of a patient.

In this embodiment, the electrical movement of the field of vision is performed by tilting the microscope body 12, through the movement transmitting mechanism 57, by the tilt driving portions 102a and 102b connected to the second tilting arm 15. However, the electrically operated members can be operated by a method different from this method. The electromagnetic brakes 37a to 37f connected to the stand electromagnetic brake driving circuit 76a are released for the electrical movement of the field of vision. Then, the driving portions 84a to 84c provided on the movement controlling mechanism 40 are driven to make a parallel movement of the tilting rod 25, whereby the microscope body 12 is moved in parallel by the action of the movement transmitting mechanism 57.

(Effects of this embodiment)

In the second embodiment, the second tilting arm 15 is disposed at the side of the microscope body 12 with respect to the vertical axis O0 and does not project much toward the opposite side of the microscope body 12 with respect to the vertical axis O0. Thus, this arm 15 does not interfere with other instruments or obstruct the work of the assistants.

The tilt driving potions 102a and 102b for performing the electric movement of the field of vision are not provided on the first tilting arm 11 but on the second tilting arm 15, and the movements are transmitted to the first tilting arm 11 by a movement transmitting member of the movement transmitting mechanism 57. Thus, the first tilting arm 11 is small in size and does not obstruct surgery. The first tilting arm 11 is made light in weight and the operating force (inertia) for moving the microscope body 12 is not increased.

A conventional surgical microscope unit in which a microscope body can be moved merely horizontally or vertically is disclosed in Jpn. Pat. Appln. KOKAI Publication 4-154442. This prior art intends to propose a stand device used for a microscope body largely moved vertically in surgical operation of eyes or the like or used for a microscope body largely moved horizontally in surgical operation of spinal cords or the like.

However, this device has complicated linkages and a bulky structure. This arrangement obstructs the surgical work of the surgeon or the operator and interferes with the other instruments.

The microscope body can move only on the previously set loci. Thus, the loci cannot be changed in accordance with various kinds of surgery.

An operation table, on which a patient is fixedly placed, is sometimes inclined during surgery of his spiral cord, and the spiral cord is not parallel with the horizontal direction. When the microscope body is moved horizontally in such a case, the focus is displaced greatly and the stand cannot perform an effective function.

On the contrary, the movement controlling mechanism 40 of this embodiment comprises guiding means having a guide shaft 86 and a slide ring 87 for limiting the moving loci of the microscope body 12, and moving means which moves the guiding means and has a vertical shaft 30, a fixing parallelogrammic linkage 31, an L-shaped arm 81, a U-shaped arm 82 and driving portions 84a to 84e so that the surgeon or the operator can move the field of vision merely on a straight line defined by connecting two arbitrary points during surgery. Therefore, the microscope unit of this embodiment can be used in any kind of surgery without being limited by methods of surgery, thereby shortening surgical operation time and reducing fatigue of the surgeon or the operator.

A surgical microscope unit according to a third embodiment of the present invention with reference to FIGS. 19 to 27.

(Structure)

Figure 19:
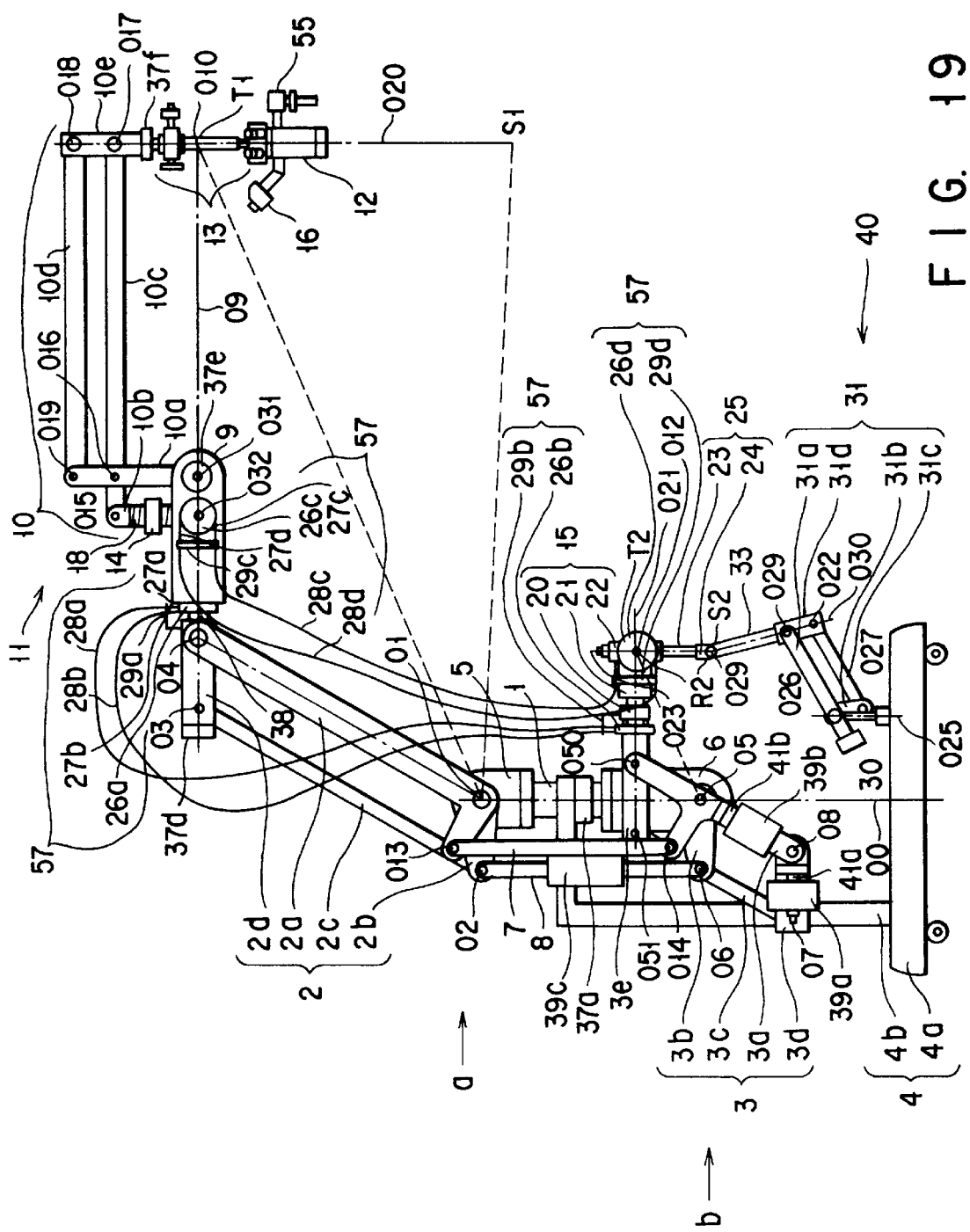
FIG. 19 is a general side view of the whole of a surgical microscope unit according to a third embodiment of the present invention.

FIG. 19 shows a general structure of the whole of the surgical microscope unit according to the third embodiment. Like the above-mentioned embodiments, a supporting device has a support 1 and a supporting base 4 for supporting the support 1. The supporting base 4 comprises a bottom plate 4a having casters on its bottom surface and a vertical stand 4b. The upper end portion of the vertical stand 4b is bent forward and horizontally. The support 1 is mounted on the bent front end of the vertical stand 4b so as to be rotatable around the vertical axis O0. A first upper parallelogrammic linkage (a displacing mechanism) 2 is connected to the upper portion of the support 1, and a second lower parallelogrammic linkage (a displacing mechanism) 3 is connected to the lower portion of the support 1.

The first parallelogrammic linkage 2 which is disposed at the upper side comprises four arms 2a to 2d connected together so as to be rotatable around parallel pivot axes O1 to O4 and forming parallelogram. The first parallelogrammic linkage 2 is connected to the upper portion of the support 1 by an upper supporting member 5 so as to be rotatable around the pivot axis O1. The pivot axis O1 and the vertical axis O0 intersect at right angles with each other.

The second parallelogrammic linkage 3 which is disposed at the lower side comprises four arms 3a to 3d connected together so as to be rotatable around parallel pivot axes O5 to O8. The second parallelogrammic linkage 3 is connected to the lower portion of the support 1 by a lower supporting member 6 so as to be rotatable around the pivot axis O5. The pivot axis O5 intersects at right angles with the vertical axis O0 and is parallel with the pivot axis O1. The first parallelogrammic linkage 2 and the second parallelogrammic linkage 3 are provided separately on the upper portion and the lower portion of the support 1, respectively. However, they are arranged in a similar relationship with each other and make interlocking deforming movement through a first connecting mechanism and a second connecting mechanism which will be described later.

The first parallelogrammic linkage 2 of the third embodiment has the same structure of those of the first and second embodiments. The second parallelogrammic linkage 3 of the third embodiment has the same structure as that of the second embodiment, in which an arm 3a assumes a T-shape having an intersection on the pivot axis O5. The lower of a first transmitting member 7 is connected to the front end portion of the short intermediate projection at its center so as to be rotatable around a pivot axis O14. A line defined by connecting the pivot axis O5 and the pivot axis O8 intersects similarly at right angles with a line defined by connecting the pivot axis O5 and the pivot axis O14 in a plane parallel with the paper surface of the drawing. The positional relationship between the two lines is not limited thereto as long as the former line is parallel with the projection bent from the arm 2a of the first parallelogrammic linkage 2.

The line defined by connecting the pivot axis O1 and the pivot axis O4 is always parallel with the line defined by connecting the pivot axis O5 and the pivot axis O8, and the lines defined by connecting the pivot axes O1, O5, O14 and O13 in turn always form a parallelogram.

In this embodiment, the arms 2a and 3aa first transmitting rod 7 for connecting them constitute a first connecting mechanism for transmitting a rotation force and interlocking the arms 2a and 3a Similarly, the pivot axis O2 of the arm 2b of the first parallelogrammic linkage 2 and the pivot axis O6 of the arm 3b of the second parallelogrammic linkage 3 are rotatably connected by a second transmitting rod 8. A line defined by connecting the pivot axis O1 and the pivot axis O2 is set to be always parallel with a line defined by connecting the pivot axis O5 and the pivot axis O6. In this embodiment, the arms 2b and 3b and the second transmitting rod 8 constitute a second connecting mechanism for transmitting rotating forces between the arms 2b and 3b and interlocking them.

On one end of the arm 2d of the first parallelogrammic linkage 2 is supported a connecting block 9 so as to be rotatable around a pivot axis O9 on the line intersecting with the vertical axis O0 and defined by connecting the pivot axis O2 and the pivot axis O4. A third parallelogrammic linkage 10 is connected to the connecting block 9. The third parallelogrammic linkage 10 comprises five arms 10a to 10e and a connecting block 9 connected together so as to be rotatable around pivot axes O15 to O19, O31 and O32 perpendicular to the paper surface of the drawing and constitutes a double parallelogrammic linkage. A first tilting arm 11 as a tilting mechanism comprises the connecting block 9 and the third parallelogrammic linkage 10 so as to be able to tilt around the pivot axes O9 and O10 perpendicular to each other.

A balance weight 14 is provided on the arm 10b of the third parallelogrammic linkage 10 so as to be slidable along a screw threaded portion 18 formed in parallel with a line connecting the pivot axis O15 and the pivot axis O32. The balance weight 14 is not limited to be provided on the arm 10b but it can be provided on one of the other arms 10a or 10e which moves in parallel with the line connecting the pivot axis O15 and the pivot axis O32.

The microscope body 12 is supported on a downward projecting end of the arm 10e by a later described microscope body supporting arm 13 provided with a balance adjusting mechanism and rotatable around the pivot axis O20 passing the line formed by connecting the pivot axis O17 and the pivot axis O18. The microscope body 12 can be rotated around the pivot axis O9, the pivot axis O20 and an imaginary pivot axis O10 passing an intersection T1 of the pivot axis O9 and the pivot axis O20 and perpendicular to the paper surface of the drawing in such a manner that the angular moments around these axes are zero. The microscope body 12 is provided with a side scope for an assistant.

The operation of the balancing action of the first and second parallelogrammic linkages 2 and 3 will be described. A screw shaft 41a is fixed to the arm 3d of the second parallelogrammic linkage 3, and a counterweight 39a is supported on the screw shaft 41a slidably in its axial directions.

Similarly, a screw shaft 41b is disposed in parallel with a line defined by connecting the pivot axis O5 and the pivot axis O8 and is fixed to the arm 3a of the second parallelogrammic linkage 3 which is adjacent to the arm 3d. A counterweight 39b is supported on the screw shaft 41b so as to be movable axially.

A counterweight 39c is fixed to the second transmitting rod 8. The weights of the counterweights 39a, 39b and 39c are distributed and their positions are arranged so that the angular moments around the pivot axes O0 and O1 are always zero.

An auxiliary counterweight comprises the counterweights 39b and 39c.

The T-shaped arm 3a constituting the second parallelogrammic linkage 3 extends toward the opposite side of the pivot axis O8 with respect to the pivot axis O5. The arm 3a is on the line passing the pivot axis O5 and the pivot axis O8. An arm 3e is connected to the forward end of the extended portion of the arm 3a so as to be rotatable around a pivot axis O50 which is opposite to the pivot axis O8 with respect to the pivot axis O5 and parallel with the pivot axis O5. An arm 3c extends toward the opposite side of the pivot axis O7 with respect to the pivot axis O6, and an arm 3e is connected to the front end of the extension which is on a line passing the pivot axis O6 and O7 at the position opposite to the pivot axis O7 with respect to the pivot axis O6 so as to be rotatable around a pivot axis O51 parallel with the pivot axis O6. A line connecting the pivot axis O5 and the pivot axis O6 is parallel with a line connecting the pivot axis O51 and a pivot axis O52, in a plane of the parallelogrammic linkage parallel with the paper surface of the drawing.

To the fixing base 20 fixed to the arm 3e is connected a rotary block 21 which is in a plane parallel with the paper surface of the drawing, intersects with the vertical axis O0 and is rotatable around the pivot axis O21. The rotary block 21 is provided with a seat 22 rotatable around the pivot axis O12 parallel with the pivot axis O10 and perpendicular to the pivot axis O21. The fixing base 20, the rotary block 21 and the seat 22 constitute a second tilting arm 15 as a tilting mechanism.

One end of a slide rod 23 is connected to the seat 22. To the other end of the slide rod 23 is connected a joint 24 so as to be rotatable around a pivot axis O23 perpendicular to the pivot axis O12 in a plane including a pivot axis O20 and parallel with the paper surface of the drawing. In this embodiment, the slide rod 23 and the joint 24 constitute a tilting rod 25 as a tilting mechanism. The weights are distributed so that the angular moments due to their own weights around the pivot axis O21, the pivot axis O12 and the pivot axis O23 are always zero.

A movement transmitting mechanism 57 which is the same as those of the first and second embodiments is provided in order to transmit the tilting movements of the microscope body 12 around the pivot axes O9 and O10 directly to the tilting rod 25 as the tilting movements around the pivot axes O21 and O12 at the same ratio. The elements of the movement transmitting mechanism 57 are shown by the same referential signs in the figure as used for the corresponding elements of the first and second embodiments, and detailed description thereof is omitted.

The base portion 4a of the supporting base 4 is provided with a vertical shaft 30 rotatable around a pivot axis O25. A fixing parallelogrammic linkage 31 comprising arms 31a to 31d pivotally connected together around parallel pivot axes O26 to O29 is connected to the vertical shaft 30 so as to be rotatable around the pivot axis O26. The pivot axis O26 is perpendicular to the vertical axis O25, and the vertical shaft 30 is provided with an electromagnetic brake for controlling (braking) the rotation around the pivot axis O25. An electromagnetic brake for controlling the rotation around the pivot axis O26 which will be described later is provided on the arm 31a and the arm 31b.

One end of a rod 33 is connected to the lower end of the joint 24 of the tilting rod 25. The other end of the rod 33 is connected to one end of the arm 31d of the fixing parallelogrammic linkage 31. The tilting rod 25 is in a plane including the pivot axis O25 and parallel with the paper surface of the drawing and is pivotally connected to each portion on a line connecting the pivot axis O28 and O29.

One end of the rod 33 is connected to the joint 24 of the tilting rod 25 so as to be rotatable around the pivot axis O24 perpendicular to the pivot axis O23. The vertical shaft 30, the fixing parallelogrammic linkage 31, the swing bar 32, the rod 33 and an electromagnetic brake which will be described later constitute a movement controlling mechanism 40. The weight of the movement controlling mechanism 40 is distributed so that the angular moments due to its own weight around the pivot axes O25, O26 and O30 are always zero.

As shown in FIG. 19, the pivot axes O1, O4, O5, O10, O12 and O50 are arranged so that a triangle formed by connecting the pivot axes O1, O4 and O10 is similar to a triangle defined by connecting the pivot axes O5, O50 and O12 in the same plane. The similarity ratio is:

$$(\Delta O1,\ O4,\ O10)/(\Delta O5,\ O50,\ O12)=C$$

where C is a constant.

The structure will be described in detail. In FIG. 19, the supporting base 4 is provided with an electromagnetic brake 37a for electrically controlling the rotation of the support 1 with respect to the support 4.

The connecting portion of the first tilting arm 11 with the arm 2d of the first parallelogrammic linkage 2 is provided with a first rotary rod 38 projecting from the connecting block 9 of the first tilting arm 11. The first rotary rod 38 is mounted on a bearing provided in the arm 2d and is rotatable around the pivot axis O9. The arm 2d is provided with an electromagnetic brake 37d for electrically controlling the rotation of the first rotary rod 38 with respect to the arm 2d The connecting rod 9 is provided with an electromagnetic brake 37e for electrically braking the rotation of the arm 10a with respect to the connecting block 9.

The arm 10e is also provided with an electromagnetic brake 37f for controlling the rotation of the microscope supporting arm 13 around the pivot axis O20 with respect to the arm 10e.

The upper supporting member 5 pivotally supporting the first parallelogrammic linkage 2 on the support 1 and the lower supporting member 6 pivotally supporting the second parallelogrammic linkage 3 on the support 1 have the same structures as those of the first embodiment as shown in FIGS. 2 and 3.

Figure 20:
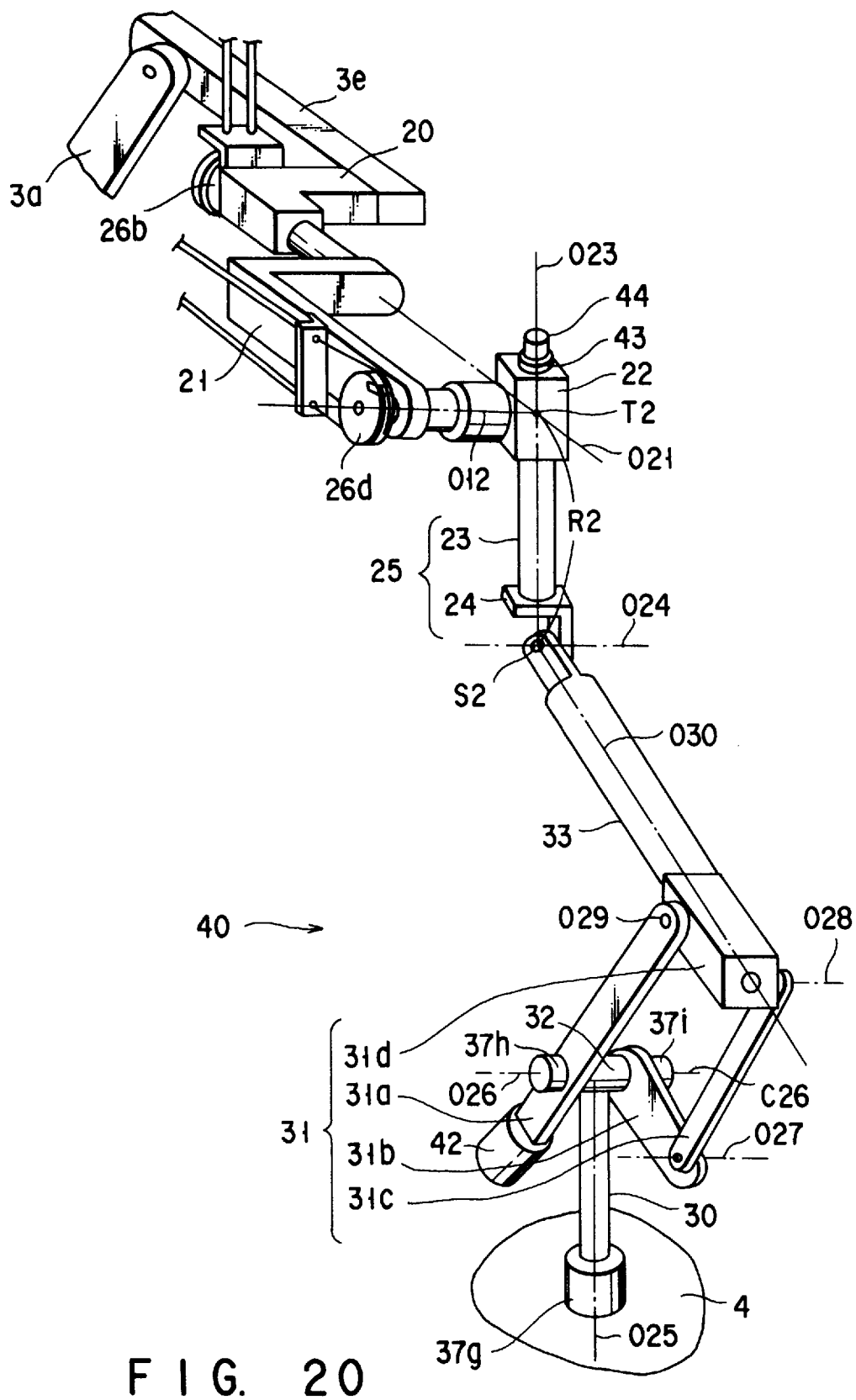
FIG. 20 is a perspective view of a movement controlling mechanism of the surgical microscope unit of the third embodiment.

FIG. 20 shows the detailed structures of the second parallelogrammic linkage 3, the second tilting arm 15, the tilting rod 25 and the movement controlling mechanism 40.

In FIG. 20 are shown an intersection T2 of the pivot axis O12 and the pivot axis O21 and an intersection S2 of the pivot axis O23, the pivot axis O23 and the pivot axis O30.

Similarly to the first embodiment, a tilting rod driving portion 43 is provided on the seat 22 and can electrically move the slide rod 23 of the tilting rod 25 along the pivot axis O23. A tilting rod position detecting portion 44 detects the driving amount of the tilting rod driving portion 43 and calculates the linear distance between T2a and S2.

An electromagnetic brake 37g can control the rotation of the vertical shaft 30 around the pivot axis O25 with respect to the supporting base 4. The arms 31a and 31b constituting the fixing parallelogrammic linkage 31 are provided with electromagnetic brakes 37h and 37i for electrically controlling the rotation of the arms 31a and 31b around the pivot axis O26 with respect to the swing lever 32.

An auxiliary weight 42 is fixed to the arm 31a and the swing lever 32 so that the angular moments of the arms 31a and the swing lever 32 around the pivot axes O26 and O25 are canceled out.

The structures of the microscope body 12 and the electric circuit will be described with reference to FIG. 21.

Figure 21:
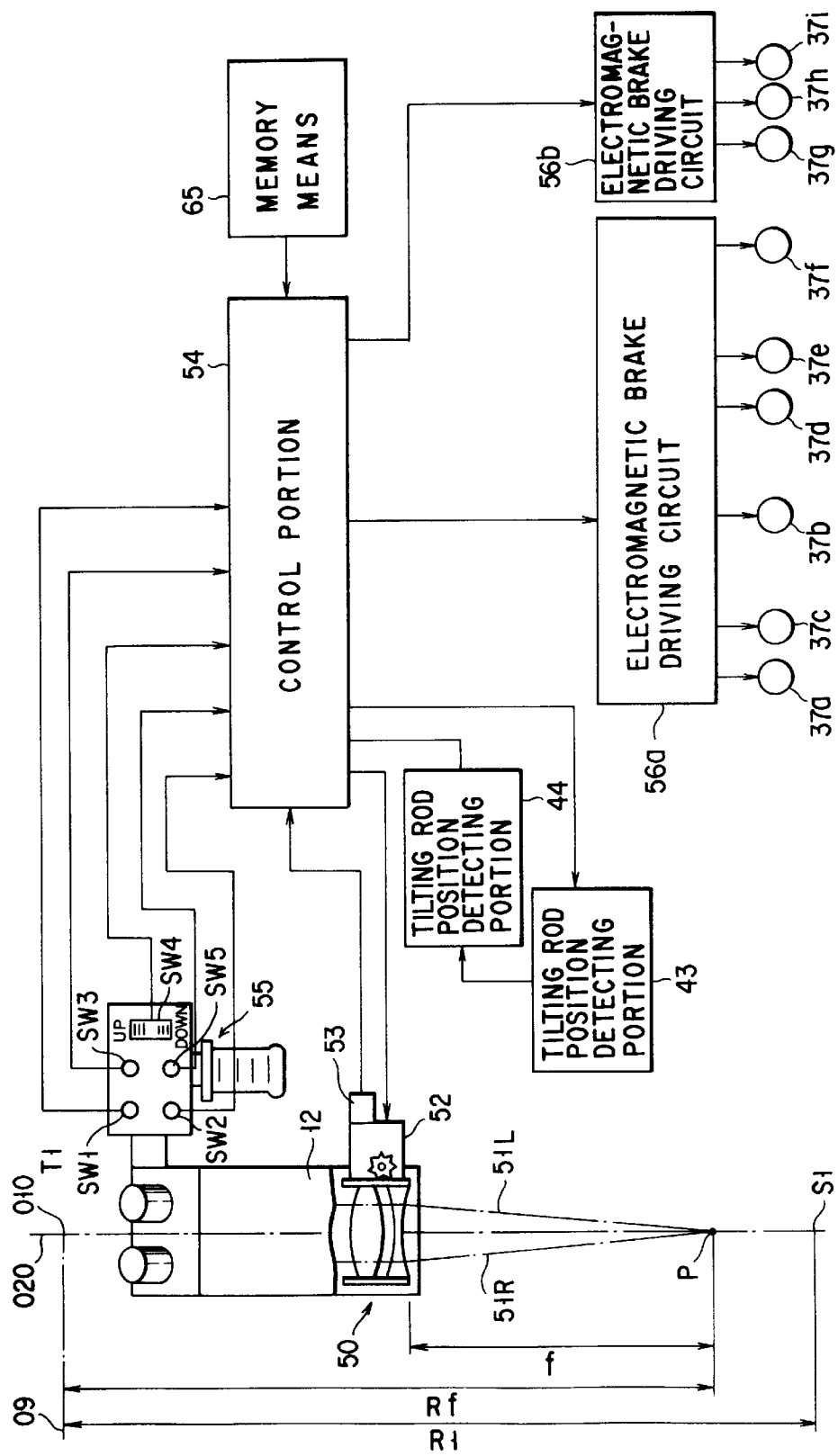
FIG. 21 is a view of a microscope body of the surgical microscope unit and an electric circuit of the microscope according to the third embodiment.

As shown in FIG. 21, an objective lens 50 is disposed on left and right observation optical paths 51L and 51R comprising a zoom lens, a focusing lens and an ocular which are not shown. The focal length of the object side can be changed by varying the distances between the lenses in the observation optical paths. The objective lens 50 is mechanically connected to an objective lens driving portion 52 to adjust the focal length. Objective lens position detecting means 53 such as an encoder is mechanically connected to the objective lens 50. In the figure, T1 designates an intersection of the pivot axis O9, the pivot axis O10 and the pivot axis O20, a point P shows an intersection of the observation optical axis, i.e., the pivot axis O20 and the focal surface of the microscope body 12, Rf indicates a linear distance between T1 and the point P, and illustrates the focal distance of the objective lens 50.

The objective lens driving portion 52 and the objective lens position detecting means 53 are connected to a control portion 54. The microscope body 12 has a grip 55 which is provided with an all direction free switch SW1, a microscope body spherical surface tilting switch SW2, a tilting center setting switch SW3, a focal length changing switch SW4, a focal length setting switch SW5 and the like. These switches are connected to the control portion 54. Memory means 65, the tilting rod driving portion 43 and the tilting rod position detecting portion 44 are also connected to the control portion 44.

The electromagnetic brakes 37a to 37f are connected to the control portion 54 through a supporting arm electromagnetic brake driving circuit 56a. Likewise, the electromagnetic brakes 37g, 37h and 37i are connected to the control portion 54 through a movement controlling mechanism electromagnetic brake driving circuit 56b.

Figure 22:
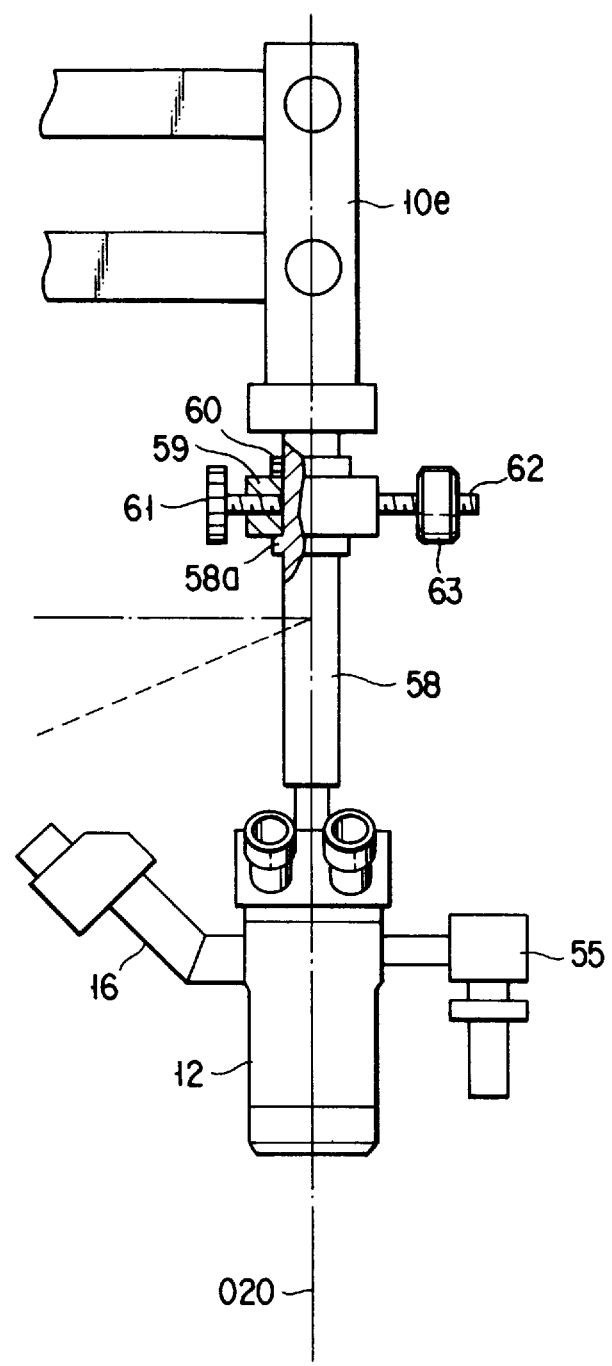
FIG. 22 is an illustrative view of a balance adjusting mechanism of a microscope supporting arm of the surgical microscope unit according to the third embodiment.
Figure 25:
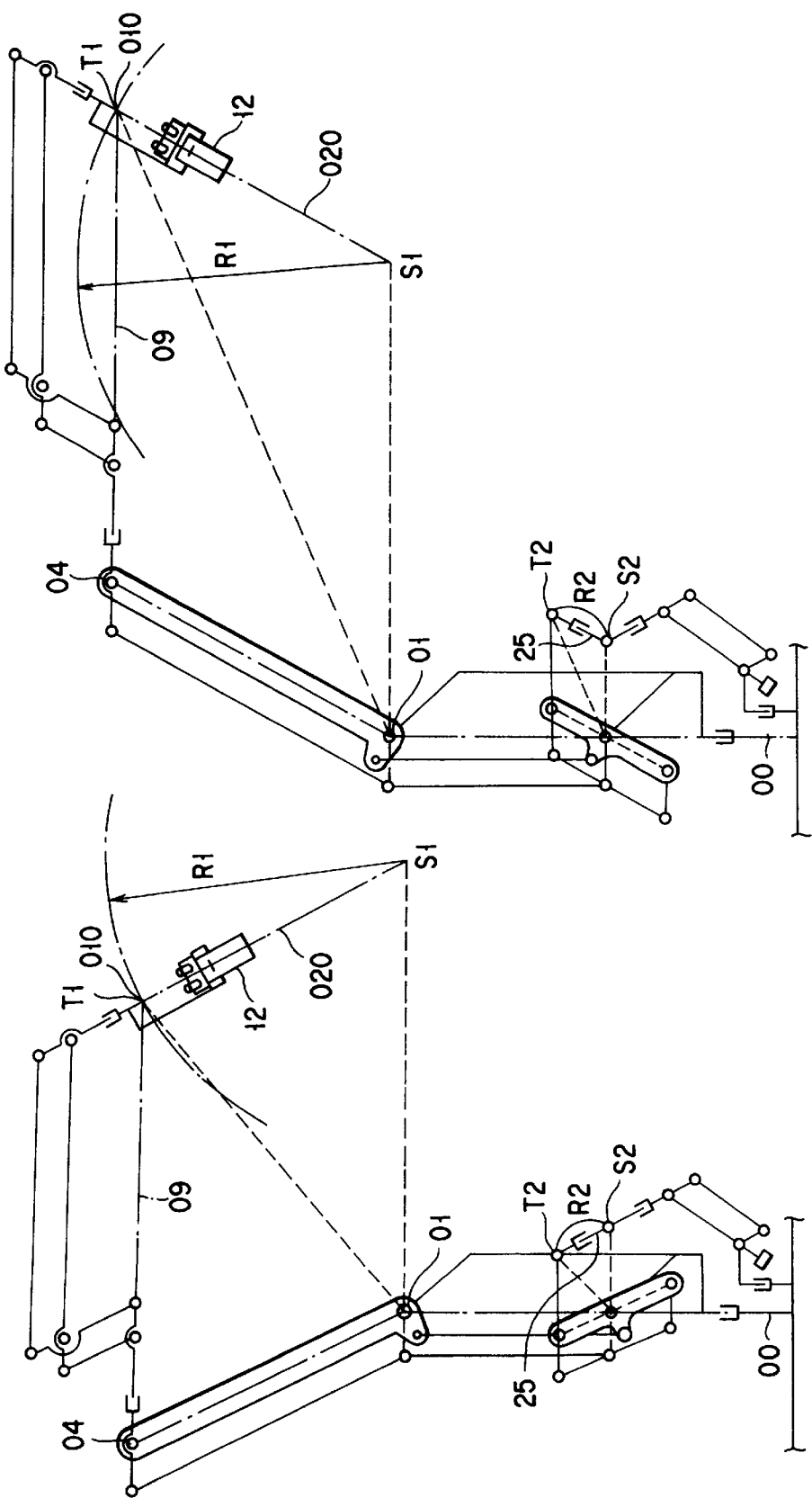
FIGS. 25A and 25B are views illustrating tilting movements of the microscope body of the surgical microscope unit according to the third embodiment around a point on an observation axis.

The balance adjusting mechanism of the microscope body supporting arm 13 will be described with reference to FIG. 22.

A connecting rod 58 is rotatably connected to the arm 10e around the pivot axis O20 with respect to the arm 10e and supports the microscope body 12 at its lower end.

A rotary ring 59 is mounted on the outer periphery of the connecting rod 5, and its axial movement along the pivot axis O20 is restricted by a projection 58a and a retaining ring 60. The rotary ring 59 is rotatable around the pivot axis O20 but can be fixed by a knob 61. A balance weight 63 is mounted on a screw shaft 62 connected to the connecting rod 58 so as to be projectingly movable in a radial direction with the pivot axis O20 as a center.

(Operation)

The operation of the surgical microscope unit according to the third embodiment will be described. With this surgical microscope unit, the tree-dimensional movements and the tilting movements around the three orthogonal axes (the movements of six degrees of freedom) and a tilting movement around a point on the observation axis can be selected according the types of surgery. The operation of them will be described.

[Movements of six degrees of freedom]

First, the all direction free switch SW1 of the grip 55 is depressed. Then, signals are inputted to the control portion 54 and corresponding signals are outputted to the supporting arm electromagnetic brake driving circuit 56a and the movement controlling mechanism electromagnetic brake driving circuit 56b. The brake action of all brakes 37a, 37b, 37c, 37d, 37e , 37f, 37g, 37h and 37i is released.

Upon release of the brake action of the electromagnetic brake 37a, the support 1 is made rotatable around the vertical axis O0 with respect to the supporting base 4, and thus the microscope body 12 is made rotatable around the vertical axis O0 with respect to the supporting base 4.

As the electromagnetic brake 37b (see FIG. 2), the arm 2b becomes rotatable around the pivot axis O1 with respect to the upper supporting member 5, and the arm 2d becomes rotatable around the pivot axis O4 with respect to the arm 2a through the arm 2c in a state in which the arm 2c is maintained in parallel with the arm 2bThus, the microscope body 12 is made rotatable around the pivot axis O4 with respect to the arm 2a through the first tilting arm 11.

Release of the electromagnetic brake 37c (see FIG. 3) allows for rotation of the arm 3a around the pivot axis O5p with respect to the lower supporting member 6, and the arm 2a connected to the arm 3a through the first transmitting rod 7 is also made rotatable around the pivot axis O1 with respect to the upper supporting member 5. Thus, the microscope body 12 becomes rotatable, as a whole, around the pivot axis O1 with respect to the upper supporting member 5 through the first tilting arm 11.

In this way, the microscope body 12 becomes rotatable three-dimensionally due to combination of the three-dimensional movements of the microscope body 12.

When, on the other hand, the electromagnetic brake 37d is released, the first tilting arm 11 is made rotatable around the pivot axis O9 with respect to the arm 22d As the electromagnetic brake 3e is released, the arm 10a of the parallelogrammic linkage 10 is made rotatable around the pivot axis O31 with respect to the connecting block 9, and the arm 10e connected by the arms 10b to 10d is made to be tilted around the pivot axis O10 by keeping parallelism with the arm 10a. Upon release of the electromagnetic brake 37f, the microscope body 12 is made rotatable around the pivot axis 20 of the arm 10e through the microscope body supporting member 13. In other words, the microscope body 12 can be rotated around an intersection T1 of the pivot axis O9 and the pivot axis O10 as a center.

Since the brake action of all brakes 39g, 37h and 37i of the movement controlling mechanism 40 is released, the vertical shaft 30 can be rotated around the pivot axis O25 with respect to the supporting base 4 and similarly the arms 31a and 31b of the fixing parallelogrammic linkage 31 can be rotated around the pivot axis O26 with respect to the swing bar 32. The rotation of the arm 31b around the pivot axis O26 with respect to the swing lever 32 is converted by the arm 31c into the rotation of the arm 31d around the pivot axis O29 with respect to the arm 31a. As a result, the rod 33 can be also rotated around the pivot axis O29 with respect to the arm 31a and around the pivot axis O30 with respect to the arm 31d. In this state, therefore, no elements restrict the movement of the microscope body 12.

In other words, the microscope body 12 can make movements of six degrees of freedom due to the three-dimensional movements and the tilting movements around the three orthogonal axes.

The movements of the microscope body 12 interlocking with the movements of six degree of freedom will be described. The arm 3b connected to the second transmitting rod 8 is rotated around the pivot axis O5 with respect to the lower supporting member 6 always in parallel with the arm 2b by the rotation of the arm 2b around the pivot axis O1 with respect to the upper supporting member 5, and the arm 3d connected in parallel with the arm 3b by the arm 3c is rotated around the pivot O8 with respect to the arm 3a In this state, the arm 3d is always maintained in parallel with the arm 2d By the rotation of arm 3a around the pivot axis O5 with respect to the lower supporting member 6, the arm 3d is rotated around the pivot axis O5 with respect to the lower supporting member 6. The tilting rod 25 is moved together with the arm 3d through the second tilting arm 15.

The arms 2a and 3a and arms 2d and 3d are moved always in parallel with each other, and a triangle formed by connecting the pivot axes O1, O4 and O10 is always similar to a triangle formed by connecting the pivot axes O5, O50 and O12 in a plane including the vertical axis O0 and parallel with the paper surface of the drawing.

FIG. 23 is a modeled view how to explain the balancing of the first parallelogrammic linkage 2 and the second parallelogrammic linkage 3.

A point P is the compound center of gravity of the elements disposed between the first tilting arm 11 on the pivot axis O9 and the microscope body 12 and including the microscope body 12. The weight exerted on the point P is W1, and the distance between the pivot axis O4 and the point P is expressed by L1.

The weight of the counterweight 39a is Wa, the distance between the pivot axis O8 and the center of the counterweight 39a is L2, the weight of the counterweight 39b is Wb, the distance between the pivot axis O5 and the center of the counterweight 39b is r2, the weight of the counterweight 39c is Wc, the distance between the pivot axis O1 and the pivot axis O2 is r1, the distance between the pivot axis O5 and the pivot axis O8 is r3, and the distance between the pivot axis O1 and the pivot axis O2 is L3.

The counterweights 39a to 39c are set at such positions as the following two equations are satisfied:

$$W1 \times L1 = Wa \times L2 + Wc \times L3,$$

and $$W1 \times r1 = Wa \times r3 + Wb \times r2.$$

It is understood that the angular moments of the first parallelogrammic links 2 and the second parallelogrammic linkage 3 are kept zero with respect to the three-dimensional movement of the microscope body 12.

FIG. 24 shows a modeled view illustrating how to balance the tilting movements of the microscope body 12. When the center of gravity of the members including the microscope body 12 which rotate around the pivot axis O20 is moved from a point Ga, at which the angular moments around the pivot axes O9, O10 and O20 are zero, to a point Gb as a result of moving a side scope connected to the microscope body 12 during surgical operation, for example, the balance weight 63 is rotated with respect to the screw shaft 62 so as to be moved in the direction of an arrow 1. Then, the center of gravity is moved from Gb to Gc and coincides with the pivot axis O20. Where the position of the center of gravity is displaced in a perpendicular direction to the paper surface of the drawing, it is preferred that the knob 61 is loosened and fixed again after the balance weight 63 together with the rotary ring 59 has be turned around the pivot axis O20 to the proper position.

Since, however, Gc is moved to the position over Ga in this case, angular moments are produced around the pivot axis O9 and the pivot axis O10. In order to cancel out these angular moments, it is preferred that the balance weight 14 provided on the arm 10e of the first tilting arm 11 is rotated with respect to the screw portion 18 so as to be moved along a line formed by connecting the pivot axis O15 and the pivot axis O32 so that the center of gravity of the elements disposed between the first tilting arm 11 and the microscope body 12 and including the microscope body 12 coincides with Ga.

In the process of these actions, the microscope body 12 can be moved at six degrees of freedom in a state in which the angular moments are always zero.

It is necessary to set the focal length to an optimum value in order to maintain a suitable space between the microscope body 12 and the portion of the patient to be surgically operated during surgery. This is attained by selecting the direction required for lengthening or shortening the focal distance and depressing the focal length changing switch SW4. A signal is inputted to the control potion 54 according to the direction of lengthening and shortening the focal length. The objective lens driving portion 52 moves the objective lens 50 in the direction which the surgeon or the operator wants according to the signal from the control portion 54.

Upon depressing the focal distance setting switch SW5, objective lens position information representing the current position of the objective lens is supplied from objective lens position detecting means 53 to memory means 65 through the control portion 54 and is memorized in the memory means 65. In this way, the focal length suited for the required surgical operation is memorized.

The portion to be observed must be focused accurately during surgery. In order to do so, the focal length is extended or shortened by pushing the focal length changing switch SW4. In other words, the actual position of the objective lens is displaced from the reference position of the objective lens.

Next, the all direction free switch SW1 is depressed to move the microscope body 12 to the aimed position. According to the signal from the switch SWI, the control portion 54 compares the objective lens position information representing the current position of the objective lens inputted from the objective lens position detecting means 53 with the objective lens reference position information memorized in the memory means 65. Then, the control portion 54 drives the objective lens driving means 52 so as to cause the current position of the objective lens to coincide with the objective lens reference position information.

Even if the focal length of the objective lens was changed from the predetermined value in order to effecting focusing during surgery, the focal length of the objective lens is corrected to the predetermined reference value.

[Tilting movement around a point on the observation optical axis]

In this case, the microscope body spherical surface tilting switch SW2 is depressed. Then, a signal from the switch SW2 is inputted to the control portion 54, and a signal is outputted to the arm supporting electromagnetic driving circuit 56a to release the brake action of merely the electromagnetic brakes 37a, 37b, 37c, 37d, 37e and 37f. In this state, only the electromagnetic brakes 38g, 37h and 37i are fixed in view of the movements of the six degrees of freedom as mentioned above.

In Fig, 25A, the tilting rod can be only tilted around the fixed point S2. The point T2 moves on the surface of a sphere having a radius equal to the distance R2 between S2 and T2. The movement of T2 is transmitted in the similar way to the movement of the above-mentioned arm so that an intersection T1 of the pivot axis O9 and the pivot axis O10 of the first tilting arm 11 moves in the opposite direction by a distance equal to the movement of the intersection T2 multiplied by C which is a constant of the similarity ratio between the similar triangles.

The tilting movement of the tilting rod 25 is transmitted to the microscope body 12 by the movement transmitting mechanism 57 using flexible wires 27a to 27d into a similar movement of the microscope 12. The operation will be described with reference to FIGS. 19 and 20.

As the tilting rod 25 is rotated around the pivot axis O12, a pulley 26d integrally provided with the seat 22 of the second tilting arm 15 is also rotated integrally. As a result, either one of wires 27c and 27d is pulled according to the rotational direction of the pulley 26d. The both end of the pulled wire is fixed to the rotary block 21d and the connecting block 9 and slide through an outer tubes 28c or an outer tube 28d whose movement along the corresponding wires is restricted, whereby the pulley 26c integrally provided with the arm 10b of the first tilting arm 11 is rotated at the same angle in the same direction of the pulley 26d. The not-pulled wire transmits the movements of the pulleys 26d and 26c in a one-to-one relation without play. The rotation of the arm 10b is transmitted into rotation of the arm 10e around the pivot axis O10 by the parallelogrammic link mechanism 10, and thus the microscope body 12 is rotated around the pivot axis O10 at the same tilting and in the same direction as the seat 22 rotating around the pivot axis O12.

When the tilting rod 25 is rotated around the pivot axis O12, the pulley 2b provided on the rotary block 21 is also rotated integrally. Either one of the wires 27a and 27b is pulled according to the rotation of the pulley 26b, the both ends of the pulled wire are fixed to the fixing base 20d and the arm 2d by fixtures 29b and 29a and slide through an outer tube 28a or an outer tube 29a whose movement along the wire is restricted. The pulley 26a integrally provided with the connecting block 9 of the tilting arm 11 is rotated at the same angle in the same direction as the pulley 26b. The not-pulled wire transmits the rotation of the pulleys 26b and 26a in a one-to-one relation without play. Thus, the microscope body 12 rotated around the pivot axis O9 at the same angle in the same direction as the rotary block 21 tilting around the pivot axis O21.

In this arrangement, the pivot axis O23 of the tilting rod 25 is maintained parallel with the pivot axis O20 of the parallelogrammic linkage 10 coaxial with the observation optical axis of the arm 10e.

As shown in FIG. 25A, the microscope body 12 can be tilted around the point S1 separated from T1 on the pivot axis O20 coaxial with the observation optical axis by a distance R2×C=R1. FIG. 25B shows a state of the microscope body 12 which is tilted rightward from its state in FIG. 25A.

Upon depressing the tilting center point setting switch SW3 of the grip 55, an objective lens position signal is inputted from the objective lens position detecting portion 53 to the control portion 54, and a tilting rod position signal is inputted from the tilting rod position detecting portion 44 to the control portion 54. From the objective lens signal, the control portion 54 calculates a distance Rf between T1 and the point P on the observation axis on the focal surface of the microscope body 12. The control portion 54 also calculates a distance between T2 and S2 from the tilting rod position signal. The value R2×C=R1 which is the distance R2 multiplied by a constant of the similarity ratio of triangles is compared with Rf. A driving signal for equalizing Rf with R1 is outputted to the tilting rod driving portion 43 to drive the tilting rod 25. On the tilting rod driving portion 43, a motor (not shown) is rotated and moves the slide rod 23 of the tilting rod 25 on the pivot axis O23 by a required length in the required direction.

While the driving signal is being supplied to the tilting rod driving portion 43, a starting signal is outputted from the control portion 54 to a movement controlling mechanism electromagnetic brake circuit 56b. The braking action of the electromagnetic brakes 37g, 37h and 37i are released with the other electromagnetic brakes 37a to 37f fixed.

In this operation, the point which the surgeon or the operator wants to set as the tilting center point of the microscope body 12 is made to coincide with the observation center point. The focusing is made, by means of the focal length changing switch SW4, on the point (the point P shown in FIG. 21) by changing the focal length of the objective lens 50 by means of the focal length changing switch SW4. Upon depression of the tilting center point setting switch SW5 of the grip 55. S1 is moved so as to coincide with P, and the tilting center point of the microscope body 12 is automatically set to the required point.

When the microscope body spherical surface tilting switch SW2 for tilting around a point on the observation optical axis is depressed, the reset functions for the six degrees of freedom do not work.

This embodiment has the objective lens driving portion 52, the objective lens position detecting portion 53, the tilting rod driving portion 43 and the tilting rod position detecting portion 44. When the focal distance setting switch SW5 is depressed by the surgeon or the operator according to the calculation in the control portion, the tilting center point S1 of the microscope body 12 can be controlled so as to coincide with the focus of the current microscope body 12.

(Effects)

The first and second moving mechanisms interlocking with the first and second parallelogrammic linkages 2 and 3 comprise the arms 2a and 3a and the first transmitting rod 7, and the arm 2b and 3b and the second transmitting rod 8, respectively. These mechanisms have no play making the cause of displacement of the field of vision of the microscope body 12 and they are rigid. Thus, the first parallelogrammic linkage 2 can be accurately interlocked with the second parallelogrammic linkage 3. And their structures are simple. A counterweight 39b as an auxiliary counterweight is provided on the arm 3a and does not extend rearward due to the movement of the microscope body 12. A counterweight 39c as an auxiliary counterweight is provided on the second transmitting rod 8 and little extends due to the movement of the microscope body 12.

The rotational balance of the arm 2a around the pivot axis O1 and the rotational balance of the arm 2b can be easily adjusted independently by the counterweights 39b and 39a, and their adjustment is easy.

The balance adjusting mechanism of the microscope body supporting arm 13 employs a moving balance weight 63, leading to a simple shape. Since the position of the microscope body 12 with respect to the pivot axis O20 is not changed, the tilting center point is not displaced from the observation focus and is operated easily although the surgical microscope unit is provided with a tilting mechanism rotatable around the observation focus.

As the all direction free switch SW1 is depressed to move the microscope 12, the focal length of the objective lens is moved to a reference position which has been set previously. Thus, a proper working area can be always obtained without greatly enlarging or reducing it by changing the focal length and repeating the movements of the microscope body 12. Because this function does not work when the microscope body 12 is tilted around the observation point upon depression of the microscope body spherical surface tilting switch SW2, the focus of the observation point does not change, and operativeness is not deteriorated.

A surgical microscope unit according to a fourth embodiment of the present invention will be described with reference to FIGS. 26 to 30.

(Structure)

Figure 26:
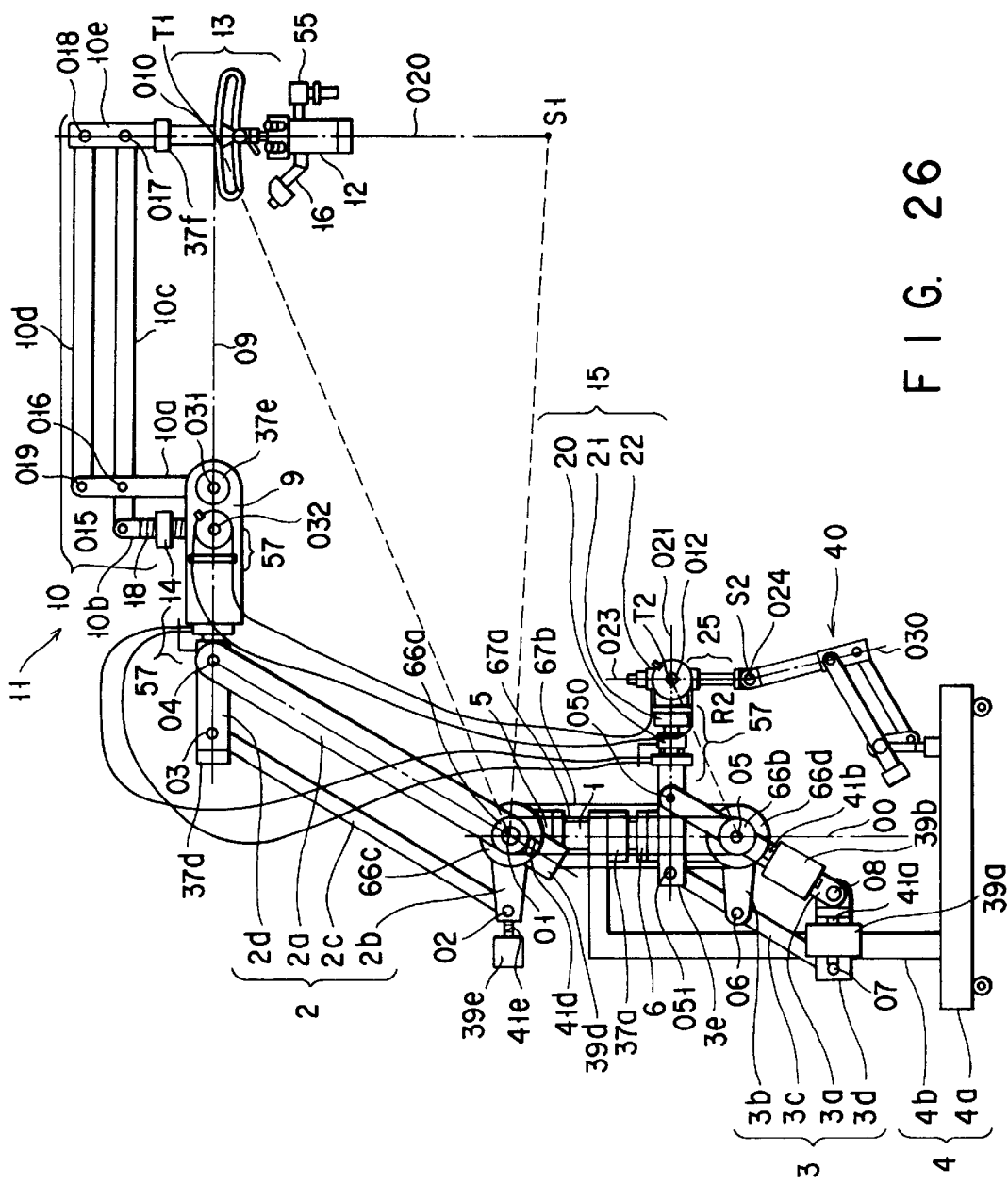
FIG. 26 is an illustrative view showing the general structure of the whole of a surgical microscope unit according to a fourth embodiment of the present invention.

FIG. 26 shows a general structure of the whole of the surgical microscope unit according to the fourth embodiment. A supporting base 4 is provided on the floor, and a support 1 is pivotally supported on the supporting base 4 around a vertical axis O0. A first parallelogrammic linkage 2 formed by connecting arms 2a to 2d so as to be rotatable around parallel pivot axes O1 to O4 in turn. The first parallelogrammic linkage 2 has the same structure as that of the first embodiment and is connected to the support 1 by an upper supporting member 5 provided on the lower portion of the support 1 so as to be rotatable around the pivot axis O1 perpendicular to the vertical axis O0.

As in the case of the third embodiment, a second parallelogrammic linkage 3 comprises arms 3a to 3d connected together around parallel pivot axes O5 to O8 in turn and is rotatably connected to the support 1 around the pivot axis O5 by means of a lower supporting member 6 provided on the upper portion of the support 1. The pivot axis O5 is perpendicular to the vertical axis O0 and parallel with the pivot axis O1.

The arm 2a of the first parallelogrammic linkage 2 is provided with a sprocket 66a on an axis coaxial with the pivot axis O1. The arm 3a is provided on an axis coaxial with the pivot axis O5 with a sprocket 66b having the same diameter as the sprocket 66a. The sprockets 66a and 66b are connected together by a chain 76a wound on them. In this state, a line connecting the pivot axis O1 and the pivot axis O4 is made always parallel with a line connecting the pivot axis O5 and the pivot axis O8. In this embodiment, a first interlocking mechanism comprises the arms 2a and 3athe sprockets 66a and 66b and the chain 67a.

An arm 2b of the first parallelogrammic linkage 2 is also provided with a sprocket 66c on an axis coaxial with the pivot axis O1, and an arm 3b is provided on an axis coaxial with the pivot axis O5 with another sprocket 66d having the same diameter of the sprocket 66c. The sprockets 66c and 66d are connected together by a chain 67b wound on them. In this case, a line connecting the pivot axis O1 and the pivot axis O2 in a plane parallel with the paper surface of the drawing is made always parallel with a line connecting the pivot axis O5 and a pivot axis O6 in a plane parallel with the paper surface of the drawing. In the fourth embodiment, a second interlocking mechanism comprises the arms 2b and 3bthe sprockets 66c and 66d and the chain 67b.

A first tilting arm 11 includes a third parallelogrammic linkage 10 which comprises arms 10a to 10e and a connecting block 9 connected together around parallel pivot axes O15 to O19, O31 and O32 like the third embodiment. An arm 10b of the third parallelogrammic linkage 10 is provided with a balance weight 14.

A microscope body 12 is supported on a downward projecting end portion of the arm 10e of the third parallelogrammic linkage 10 by a microscope supporting arm 13 having a later-described balance adjusting mechanism movable around a pivot axis O20 passing the pivot axis O17 and the pivot axis O18.

As in the case of the third embodiment, the microscope body 12 is rotatable around an imaginary pivot axis O10 passing the pivot axis O9, the pivot axis O20 and an intersection of the pivot axis O9 and the pivot axis O20 and perpendicular to the paper surface of the drawing in the state in which angular moments around the corresponding axes are zero.

The microscope body 12 is provided with a side scope for an assistant.

The balancing mechanism for the first and second parallelogrammic linkages 2 and 3 will be described.

As in the third embodiment, a counterweight 39a is supported by a screw shaft 41a on the arm 3d of the second parallelogrammic linkage 3 so as to be movable axially thereof.

In the same way as in the case of the first embodiment, a counterweight 39b is supported by a screw shaft 41b on the arm 3a so as to be movable thereof.

A counterweight 39d is supported on the arm 2a of the first parallelogrammic linkage 2 by a screw shaft 41d connected to a part of the arm 2a opposite to the pivot axis O4 with respect to the pivot axis O1 so as to be movable axially of the screw shaft 41d.

A counterweight 39e is supported on the arm 2b by a screw shaft 41e connected to a part of the arm 2b opposite to the pivot axis O1 with respect to the pivot axis O2 so as to be movable axially of the screw shaft 41e.

The weights of the counterweights 39a, 39b, 39d and 39e are distributed and these counterweights are arranged so that the angular moments around the pivot axis O0 and the pivot axis O1 are always zero when the first parallelogrammic linkage 2 and the second parallelogrammic linkage 3 are interlockingly operated.

In this embodiment, an auxiliary counterweight comprises the counterweights 39b, 39d and 39e.

A second tilting arm 15 having the same structure as that of the third embodiment and connected to the second parallelogrammic linkage 3 comprises a fixing base 20, a rotary block 21 and a seat 22 and supports a tilting rod 25 in a state in which the angular moments are zero as in the case of the third embodiment.

A movement controlling mechanism 40 has the same structure as that of the third embodiment, and the description thereof is omitted.

A movement transmitting mechanism 57 has pulleys, wires, outer tubes, fixtures and the like as in the third embodiment.

As in the third embodiment, T2 indicates an intersection of a pivot axis O12 and a pivot axis O21, S2 shows an intersection of a pivot axis O23, a pivot axis O24 and a pivot axis O30, and R2 represents a linear distance between T2 and S2.

In the same way as the third embodiment, the pivot axes O1, O4, O5, O10, O12 and O50 in a plane parallel with the paper surface of the drawing are arranged so that a triangle formed by connecting the axes O1, O4 and O10 is similar to a triangle formed by connecting the pivot axes O5, O50 and O12. The similarity ratio is:

(ΔO1, O4, O10)/(ΔO5, O50, O12)=C where C is a constant.

Electromagnetic brakes 37a to 37i for controlling the rotation of the pivot axes are provided in the same portions as those of the third embodiment. The electromagnetic brakes 37a to 37i of the movement controlling mechanism 40 are shown in FIG. 20 which also illustrates the third embodiment.

The structure of an electrical circuit of this embodiment is the same as that of the third embodiment as illustrated in FIG. 21, and its description is omitted.

Figure 27:
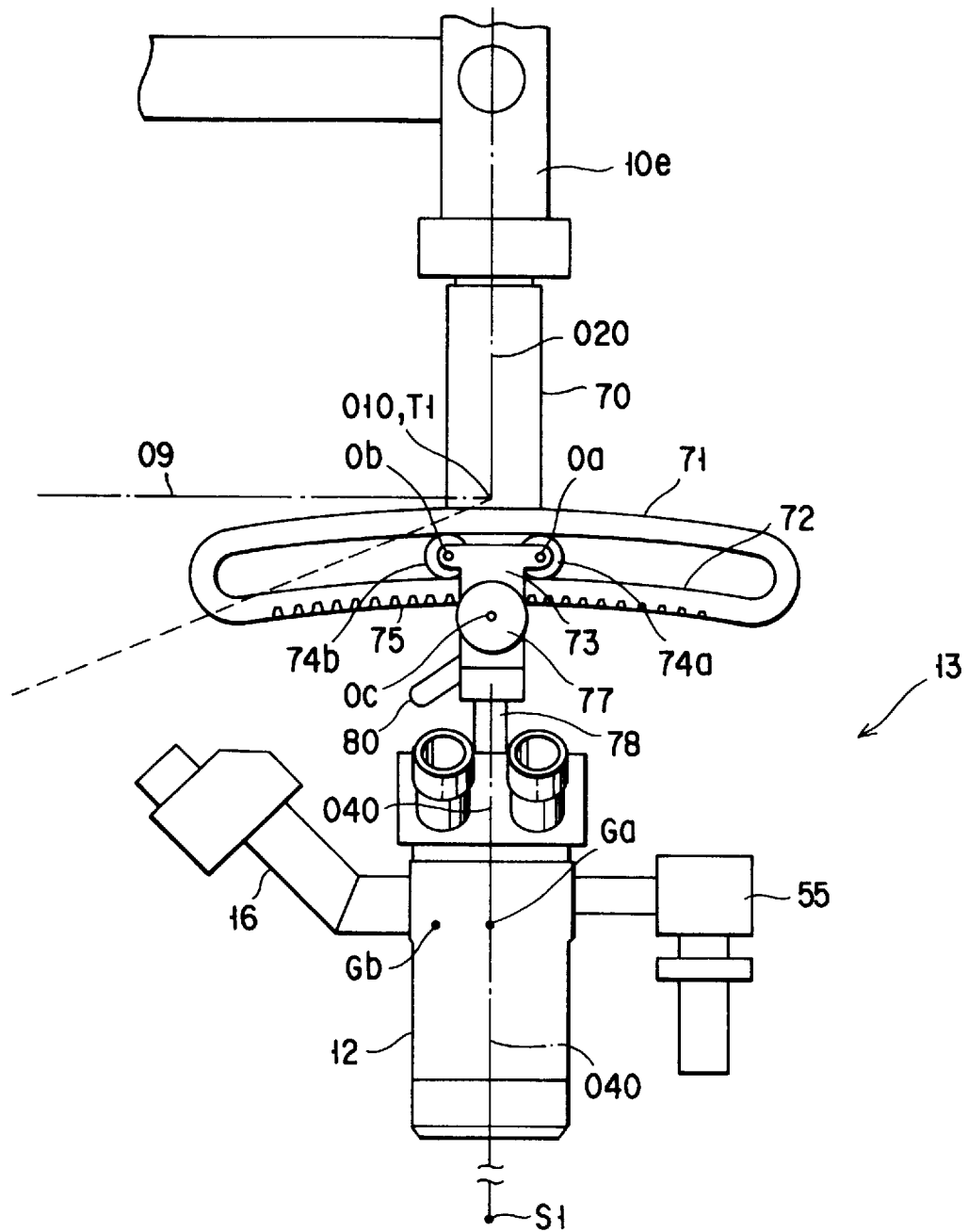
FIG. 27 is a general front view of a balance adjusting mechanism of a microscope supporting arm according to the fourth embodiment.
Figure 28:
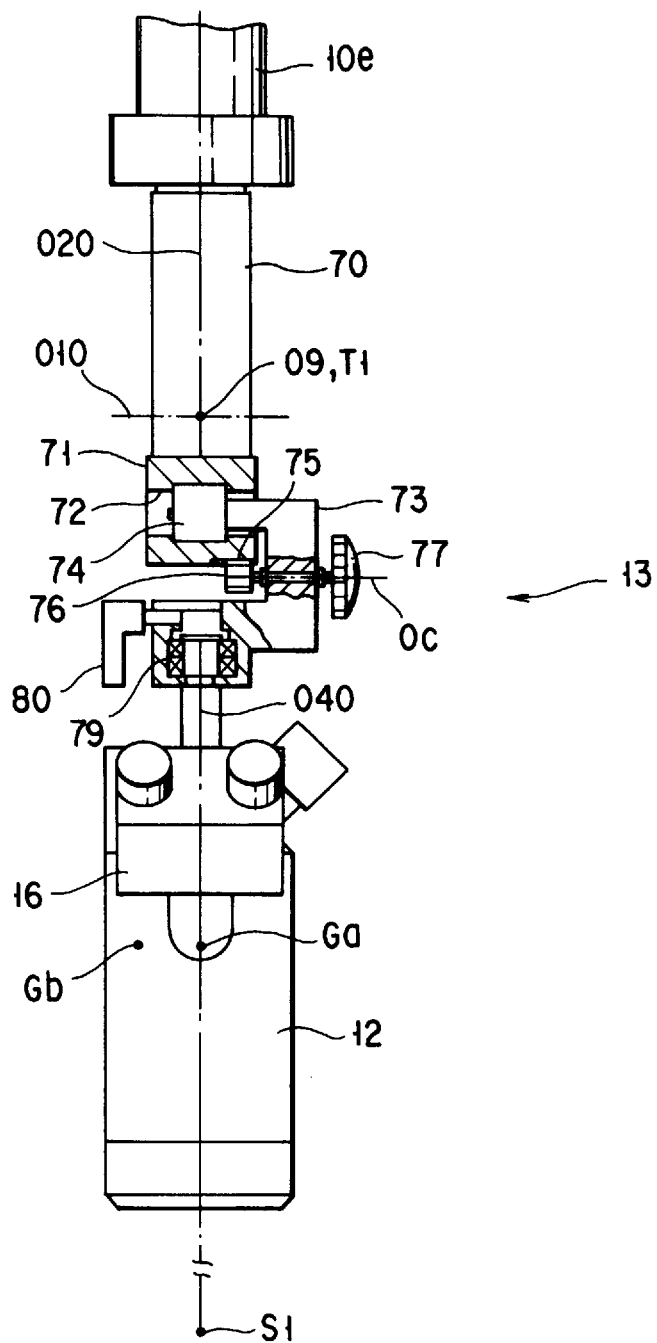
FIG. 28 is a general side view of the balance adjusting mechanism of the microscope supporting arm of the surgical microscope unit.

A balance adjusting mechanism of the microscope body supporting arm 13 will be described. FIG. 27 is a front view of the microscope supporting arm 13 and FIG. 28 is a side view thereof.

A connecting rod 70 is rotatably connected to an arm 10e around a pivot axis O20, and an arcuated guide member 71 is fixed to the lower portion of the connecting rod 70.

The arcuated guide member 71 is formed with a guide groove 72 which extends toward the both lateral sides of the a point S1 on the pivot axis O20 as a center of the tilting movement of a microscope 12 and has a constant width. Two rollers 74a and 74b rotatably connected to a moving body 73 around pivot axes Oa and Ob are inserted in the guide groove 72 so as to movable therealong.

A rack 75 is formed on the undersurface of the arcuated guide member 71. A pinion gear 76 engages the rack 75 and is rotatable around a pivot axis Oc together with a knob 77 provided on the moving member 73.

A supporting arm 78 fixed to the microscope body 12 is connected through a bearing 79 to the lower portion of the moving body 73 so as to be rotatable around a pivot axis O40 coaxial with the observation axis of the microscope optical axis 12 and is fixed to the moving body 73 by a lever 80 screwed into the moving body 73. In the state shown in the figure, the pivot axis O20 and the pivot axis O40 are coaxial with each other.

(Operation)

The surgical microscope of this embodiment makes the same movements of six degrees of freedom and tilting movement around a point on the observation axis as that of the third embodiment. These movements will be described.

[Movements of six degrees of freedom]

As an all direction free switch SW1 of a grip 55 is depressed, a signal is inputted to the control potion 54. Signals are outputted to a supporting arm electromagnetic brake driving circuit 56a and a movement controlling mechanism electromagnetic brake driving circuit 56b, and all electromagnetic brakes 37a to 37i are released.

Upon release of the electromagnetic brake 37a, the support 1 is made rotatable around the vertical axis O0, and the microscope body 12 is made rotatable around the pivot axis O0 with respect to the supporting base 4 through the first parallelogrammic linkage 2 and the first tilting arm 11.

When the electromagnetic brake 37b is released (see FIG. 2), the arm 2b becomes rotatable around the pivot axis O1 with respect to the upper supporting member 5, and the arm 2d becomes rotatable around the pivot axis O4 with respect to the arm 2a through the arm 2c in a state in which the arm 2d is parallel with the arm 2bThus, the microscope body 12 becomes rotatable around the pivot axis O4 with respect to the arm 2a through the first tilting arm 11.

As the electromagnetic brake 37c is released (see FIG. 3), the arm 3a becomes rotatable around the pivot axis O5 with respect to the lower supporting member 6, and the sprocket 66b provided on the arm 3a is made rotatable. The rotation of the sprocket 66b is transmitted to the sprocket 66a provided on the arm 2a by the chain 67a, and the arm 2a is made rotatable around the pivot axis O1 with respect to the upper supporting member 5. Thus, the microscope body 12 is made rotatable around the pivot axis O1 with respect to the upper supporting member 5 through the first tilting arm 11. In this state, the arm 3a is always maintained parallel with the arm 2a.

As in the case of the third embodiment, the microscope 12 is made to be moved three-dimensionally according to these three movements.

The operation of the electromagnetic brakes 37d to 37f when they are released is the same as that of the third embodiment, and the microscope body 12 is made rotatable around an intersection T1 of the three pivot axes O9, O10 and O20.

Since all electromagnetic brakes 37g, 37h and 37i of the movement controlling mechanism 40 are released, no elements restrict the movements of the microscope body 12 as in the case of the third embodiment.

In other words, the microscope body 12 can be moved at six degrees of freedom according to the three-dimensional movements and the tilting movements around the three orthogonal axes.

The operation interlocking with the movements of the six degrees of freedom will be described.

A s the arm 2b is rotated around the pivot axis O1 with respect to the upper supporting member 5, the sprocket 66c provided on the arm 2b is made rotatable. The rotation of the sprocket 66c is transmitted to the sprocket 66d provided on the arm 3b by a chain 67b, and the arm 3b is rotated around the pivot axis O5 with respect to the lower supporting member 6 in a state in which the arm 3b is always maintained parallel with the arm 2b. The arm 3d connected to the arm 3b in a parallel manner y the arm 3c is also rotated around the pivot axis O8 with respect to the arm 3aIn this case, the arm 3d is always maintained parallel with the arm 2d.

As the arm 3a is rotated around the pivot axis O5 with respect to the lower supporting member 6, the arm 3b is rotated around the pivot axis O5 with respect to the lower supporting member 6.

The tilting rod 25 is moved together with the arm 3d through the second tilting arm 15.

In this state, the group of the arms 2a and the arm 2b and the group of the arm 2d and the arm 3d are moved in parallel with each other, and a triangle formed by connecting the pivot axes O1, O4 and O10 is always maintained similar to a triangle formed by connecting the pivot axes O5, O50 and O12 in a plane parallel with the paper surface of the drawing.

FIG. 29 is a modeled view illustrating how to balance the first parallelogrammic linkage 2 and the second parallelogrammic linkage 3.

The compound center of gravity of the members between the first tilting arm 11 and the microscope body 12 is designated by G1. Its weight is represented by W1 and the distance between the pivot axis O4 and the center of gravity is shown by L1.

Wa is the weight of the counterweight 39a, L2 is the distance between the pivot axis O8 and the center of gravity of the counterweight 39a, Wb is the weight of the weight of the counterweight 39b, r2 is the distance between the pivot axis O1 and the center of gravity of the counterweight 39b, Wd is the weight of the counterweight 39d, r4 is the distance between the pivot axis O1 and the center of the gravity of the counterweight 39d, We is the weight of the counter-weight 39e, L4 is the distance between the pivot axis O1 and the center of gravity of the counterweight 39e, r1 is the distance between the pivot axes O1 and O4, and r3 is the distance between the pivot O5 and O8.

The counterweights 39a, 39b, 39d and 39e are disposed in such positions as satisfy the following two equations:

$$W1 \times L1 = Wa \times L2 + We \times L4,$$

and $$W1 \times r1 = Wa \times r2 + Wb \times r2 + Wd \times r4.$$

When the microscope body 12 is moved three-dimensionally, the angular moments of the first parallelogrammic linkage 2 and the second parallelogrammic linkage 3 are maintained zero.

The balance of the microscope body 12 when it is tilted will be described. When, a shown in FIGS. 27 and 28, the compound center of gravity of the members including the microscope body 12 rotating around the pivot axis O20 is displaced from the point Ga at which the angular moments around the pivot axes O9, O10 and O20 to Gb due to the change of the position of the side scope 16 connected to the microscope body 12 or due to the like cause, the lever 80 is loosened, and the microscope body 12 is rotated around the pivot axis O40 coaxial with the observation optical axis of the microscope body 12 through the supporting arm 78 to make the center of gravity Gb to lie in a plane including Ga and parallel with the paper surface of FIG. 13. Then, the lever 80 is tightened.

Figure 30:
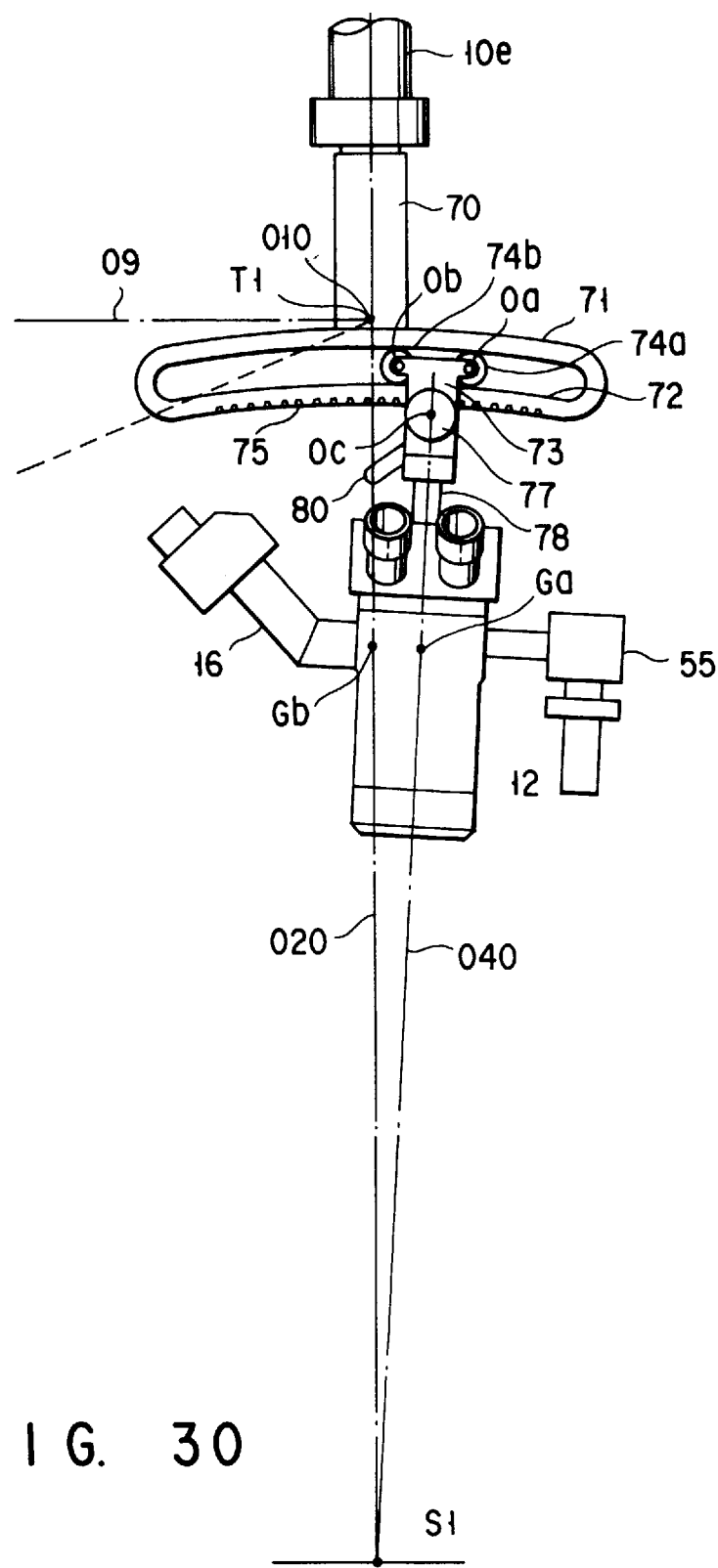
FIG. 30 is a general front view of the balance adjusting mechanism of the microscope supporting arm of the surgical microscope unit.

As the knob 77 is rotated, the pinion gear 76 coaxial therewith engages the rack 75 formed on the arcuated guide member 71. As shown in FIG. 30, the rollers 74a and 74b slidably moves in the guide groove 72 and the moving member 73 is moved on an arc having S1 as its center which is the tilting center of the microscope body 12.

It is, therefore, preferred that the microscope body 12 together with the moving member 73 is tilted around S2 by turning the knob 77 to cause the center of gravity Gb to coincide with the pivot axis O20.

When the angular moments around the pivot axis O9 and the pivot axis O10 are produce by the vertical movement of the center of gravity Gb, it is preferred that the balance weight 14 provided on the arm 10b is rotated with respect to the screw portion 18 and is moved along the line connecting the pivot axis O15 and the pivot axis 32, as shown in FIG. 24 illustrating the third embodiment, in order to cancel out the angular moments.

In this way, the microscope body 12 can be moved at the six degrees of freedom in a state in which the angular moments are zero.

[Tilting movement around a point on the observation optical axis]

Upon depression of the microscope spherical surface tilting switch SW2 of the grip 55, a signal is inputted to the control portion 54. Signals are outputted only to the supporting arm electromagnetic brake driving circuit 56a and the braking action of the electromagnetic brakes 37a to 37f is released. In this state, only the electromagnetic brakes 37g to 37i are fixed.

In the same way as the third embodiment, the movement of the intersection S2 of the pivot axes O23, O24 and O30 are restricted and the tilting rod 25 can be tilted only around S2. The point T2 moves on the spherical surface having a radius equal to the distance R2 between S2 and T2. The movement of T2 is transmitted in the same way as the aforementioned arm, and the intersection T1 of the pivot axis O9 and the pivot axis O10 of the first tilting arm is moved in the opposite direction by a distance equal to the moving distance of T2 multiplied by C which is the ratio of the above-mentioned similar triangles.

The movement of the first tilting arm 11 is transmitted according to the movement of the movement transmitting mechanism 57 in the same way as the third embodiment.

The microscope body 12 can be tilted around the point S1 separated by a distance $R2 \times C = R1$ from T1 on the pivot axis O20 coaxial with the observation optical axis.

(Effects)

Since the first and second interlocking mechanisms of the fourth embodiment comprise a group of the arms 2a and 3athe sprockets 66c and 66d and the chain 67b and a group of the arms 2b and 3bthe sprockets 66c and 66d and the chain 67b, these mechanisms do not project from the line connecting the pivot axis O1 and the pivot axis O5 and thus can be made small in size.

The counterweights 39d and 39e as auxiliary counterweights are provided on the arms 2a and 2b rotatable around the pivot axis O1, and they are disposed close to the waist of the surgeon or the operator. Thus, the surgeon or the operator can adjust the balance of the counterweights 39d and 39e at a comfortable posture as compared with the case in which the balance adjustment is made by moving the counterweights 39a and 39b.

The counterweights 39a and 39b are provided below, the counterweights 39d and 39e can naturally made small, and they do not obstruct the work of the surgeon or the operator and the assistants and can be adjusted easily.

When the balance adjusting mechanism of the microscope body 12 is used, the microscope body 12 is rotated around the tilting center point S1 of the microscope body 12 by the arcuated guide member 71. Even if a tilting mechanism which is tilted around the observation focus is provided, the surgical microscope unit can be operated easily because its tilting center is not displaced from the observation focus.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A surgical microscope unit having a moving mechanism which supports a microscope body and which can move said microscope body three-dimensionally so that said microscope body is capable of tilting around three axes, said moving mechanism comprising:

a support having a vertical axis;

a first parallelogrammic linkage rotatably mounted on said support so as to be rotatable around said vertical axis, said first parallelogrammic linkage having first, second, third and fourth parallel pivot axes intersecting with a plane including said vertical axis, and said first parallelogrammic linkage having first, second, third and fourth arms pivoted together by said first, second, third and fourth pivot axes and rotatably supported on said support at said first pivot axis;

a second parallelogrammic linkage rotatably supported on said support so as to be rotatable around said vertical axis, said second parallelogrammic linkage being arranged opposite said first parallelogrammic linkage with respect to said vertical axis, said second parallelogrammic linkage having first, second, third and fourth parallel pivot axes intersecting a plane including said vertical axis, and said second parallelogrammic linkage having first, second, third and fourth arms pivoted together by said first, second, third and fourth pivot axes of said second parallelogrammic linkage and rotatably supported on said support at said first pivot axis of said second parallelogrammic linkage;

a first interlocking mechanism for interlocking rotation of said first arm of said first parallelogrammic linkage around said first pivot axis of said first parallelogrammic linkage with rotation of said first arm of said second parallelogrammic linkage around said first pivot axis of said second parallelogrammic linkage so that a line formed by connecting said first pivot axis and said second pivot axis adjacent thereto of said first parallelogrammic linkage is always parallel with a line formed by connecting said first pivot axis and said second pivot axis adjacent thereto of said second parallelogrammic linkage;

a second interlocking mechanism for interlocking rotation of said second arm of said first parallelogrammic linkage around said first pivot axis of said first parallelogrammic linkage with rotation of said second arm of said second parallelogrammic linkage around said first pivot axis of said second parallelogrammic linkage so that a line formed by connecting said first pivot axis and said third pivot axis adjacent thereto of said first parallelogrammic linkage is always parallel with a line formed by connecting said first pivot axis and said third pivot axis of said second parallelogrammic linkage, said microscope body being supported by said third arm of said first parallelogrammic linkage including said second pivot axis of said first parallelogrammic linkage which is adjacent to said first pivot axis thereof and said fourth pivot axis thereof which is diagonally disposed; and a counterweight for reacting an unbalanced force exerting on said first parallelogrammic linkage and said microscope body, said counterweight being provided on said second parallelogrammic linkage.

2. The surgical microscope unit according to claim 1, further comprising:

a first tilting arm connected to said third arm of said first parallelogrammic linkage, said first tilting arm having a front end portion connected to said microscope body and a first pivot axis and a second pivot axis perpendicular to each other and allowing said microscope unit to be tilted therearound;

a second tilting arm connected to said third arm disposed opposite to said second arm of said second parallelogrammic linkage, said second tilting arm having a tilting rod connected to a front end thereof and a first pivot axis and a second pivot axis perpendicular to each other and around which said tilting rod is tilted, said first and second pivot axes of said second tilting arm being parallel with respect to said first and second pivot axes of said first tilting arm, respectively;

a movement transmitting mechanism for transmitting tilting movement of said microscope body around said first and second pivot axes of said first tilting arm to said tilting rod as tilting movement of said tilting rod around said first and second pivot axes of said second tilting arm; and a movement controlling mechanism for limiting a moving locus of said tilting rod to a corresponding location at which said microscope unit is set;

wherein a triangle formed by connecting said first and second pivot axes of said first parallelogrammic linkage and said first pivot axis of said first tilting arm is similar to a triangle formed by connecting said first and second pivot axes of said second parallelogrammic linkage and said first pivot axis of said second tilting arm.

3. The surgical microscope unit according to claim 2, wherein said movement controlling mechanism includes a linear guide for moving said tilting rod so that a given point on said tilting rod corresponding to a point on an axis extending from an optical axis of said microscope body moves linearly.

4. The surgical microscope unit according to claim 3, wherein said movement controlling mechanism includes a connecting portion which connects said given point on said tilting rod to electrical driving means for driving said connecting portion.

5. The surgical microscope unit according to claim 2, wherein said movement transmitting mechanism includes flexible transmitting members for connecting said first tilting arm to said second tilting arm and for performing transmission of rotation between said first and second tilting arms forming said triangles around said first pivot axes of said first and second tilting arms.

6. The surgical microscope unit according to claim 2, wherein said movement transmitting mechanism includes slider crank mechanisms for connecting said first tilting arm to said second tilting arm and for performing transmission of rotation between said first and second tilting arms around said second pivot axes of said first and second tilting arms, and belt transmitting devices.

7. The surgical microscope unit according to claim 1, further comprising an interlocking member for moving at least one of said first interlocking mechanism and said second interlocking mechanism, and an auxiliary counterweight provided on said interlocking member.

8. A surgical microscope unit having a moving mechanism which supports a microscope body and which can move the microscope body three-dimensionally on a limited locus, said moving mechanism comprising:

a support having a vertical axis;

two parallelogrammic linkages rotatably mounted on said support so as to be rotatable around said vertical axis at positions separated upward and downward, respectively, from said vertical axis, said two parallelogrammic linkages each having four parallel pivot axes intersecting with a plane including said vertical axis and four arms pivoted together by said four pivot axes, said two parallelogrammic linkages being pivoted on said support at first pivot axes of said four pivot axes, and two arms of said four arms of each of said two parallelogrammic linkages extending substantially horizontally;

two tilting arms connected to said substantially horizontally extending two arms of said first parallelogrammic linkage which include second pivot axes of said four pivot axes adjacent to said first pivot axes of said two parallelogrammic linkages and third pivot axes of said four axes disposed diagonally of said first pivot axes, one of said tilting arms having a forward end connected to said microscope body which is rotatable around two orthogonal pivot axes;

a tilting rod pivotally connected to a front end of the other one of said two tilting arms around pivot axes of said two tilting arms and parallel with said orthogonal pivot axes and around which said microscope body is rotatable;

interlocking mechanisms for interlocking said two parallelogrammic linkages so that a triangle formed by said first and second pivot axes of one of said parallelogrammic linkages and the pivot axis of said one of said tilting arms is similar to a triangle formed by said first and second pivot axes of the other one of said parallelogrammic linkage and the pivot axis of the other one of said tilting arms;

a movement transmitting mechanism for transmitting tilting movement of said microscope body around said pivot axes of said tilting arms to said tilting rod as tilting movement around said pivot axes of said two tilting arms at a same ratio; and a movement controlling mechanism for limiting a moving locus of said tilting rod to a corresponding location at which said microscope unit is set.

9. The surgical microscope unit according to claim 8, wherein said movement controlling mechanism comprises a pivotal portion pivoted on a given point on said tilting rod, and fixing means for fixing three-dimensional movements of said pivotal portion.

10. The surgical microscope unit according to claim 9, wherein said given point corresponds to a predetermined point on an optical axis of an objective lens of said microscope body.

11. The surgical microscope unit according to claim 2, wherein said movement controlling mechanism includes a linear guide for moving said tilting rod so that a given point on said tilting rod corresponding to a point on an axis extending from an optical axis of said microscope body moves linearly.

12. The surgical microscope unit according to claim 11, wherein said movement controlling mechanism includes a connecting portion which connects said given point on said tilting rod to electrical driving means for driving said connecting portion.

\* \* \* \* \*